(12) United States Patent
Chan et al.

(10) Patent No.: US 11,192,888 B2
(45) Date of Patent: Dec. 7, 2021

(54) ANTIBACTERIAL COMPOUNDS

(71) Applicant: THE UNIVERSITY OF NOTTINGHAM, Nottinghamshire (GB)

(72) Inventors: Weng Choon Chan, Nottinghamshire (GB); Sivaneswary Genapathy, Hatfield (GB); Lei Yang, Shanghai (CN)

(73) Assignee: The University of Nottingham, Nottingham (GB)

( * ) Notice: Subject to any disclaimer, the term of this patent is extended or adjusted under 35 U.S.C. 154(b) by 0 days.

(21) Appl. No.: 16/493,870

(22) PCT Filed: Mar. 16, 2018

(86) PCT No.: PCT/GB2018/050685
§ 371 (c)(1),
(2) Date: Sep. 13, 2019

(87) PCT Pub. No.: WO2018/167506
PCT Pub. Date: Sep. 20, 2018

(65) Prior Publication Data
US 2020/0199118 A1 Jun. 25, 2020

(30) Foreign Application Priority Data
Mar. 16, 2017 (GB) ..................... 1704166

(51) Int. Cl.
*C07D 417/14* (2006.01)
*A61P 31/04* (2006.01)
*A61K 45/06* (2006.01)

(52) U.S. Cl.
CPC ............ *C07D 417/14* (2013.01); *A61P 31/04* (2018.01); *A61K 45/06* (2013.01)

(58) Field of Classification Search
CPC .................................................. C07D 417/14
See application file for complete search history.

(56) References Cited

PUBLICATIONS

Chou-Hsiung Chen et al. (Organic & Biomolecular Chemistry, 12, 2014—Supplemental info.*
Chen et al. "A facile approach to tryptophan derivatives for the total synthesis of argyrin analogues." Organic & Biomolecular Chemistry 12(48): 9764-9768 (2014).

* cited by examiner

*Primary Examiner* — Brian E McDowell
(74) *Attorney, Agent, or Firm* — Nixon Peabody LLP; Mark J. FitzGerald; Ravinderjit Braich

(57) ABSTRACT

Novel compounds having antimicrobial activity, in particular against *Pseudomonas aeruginosa*, *Burkholderia cepacia* and/or *Clostridium difficile*, and a pharmaceutical composition containing the novel compound.

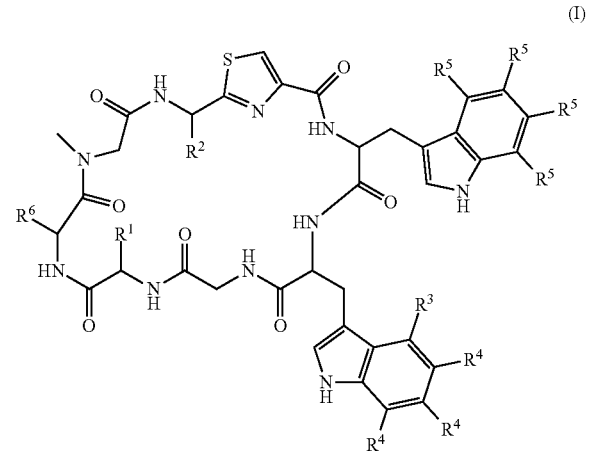

(I)

19 Claims, 4 Drawing Sheets

ANTIBACTERIAL COMPOUNDS

CROSS-REFERENCE TO RELATED APPLICATIONS

This application is a 35 U.S.C. § 371 National Phase Entry Application of International Application No. PCT/GB2018/050685 filed Mar. 16, 2018, which designates the U.S. and claims benefit of priority to EP 1704166.6 filed Mar. 16, 2017, the contents of each of which are incorporated herein by reference in their entireties.

FIELD OF THE INVENTION

This application relates to peptide-based compounds. These compounds may find particular use in the treatment of microbial infections, especially of the human gut. In particular, these compounds are useful in the treatment of infection by *Pseudomonas aeruginosa, Burkholderia cepacia* and/or *Clostridium difficile*.

BACKGROUND OF THE INVENTION

A significant medical challenge that faces the 21st century is the rise of antibiotic-resistant bacteria. The European Medicines Agency (EMEA) has estimated that antibiotic-resistant bacteria cause around 25,000 deaths in the Europe and 5,000 deaths in the UK each year. The additional health care cost along with the productivity losses is estimated to cost the EU nations at least €1.5 billion a year (J. Brandt, *Am. J. Gastroenterol.*, 2013, 108, 177-185). A review summarised by Butler et al. pointed out that between the year 2000 and 2013, only five new classes of antibiotics have been introduced to the market, and none of the new agents have indication for the treatment of multidrug-resistant Gram-negative bacteria (M. S. Butler, M. A. Blaskovich and M. A. Cooper, *J. Antibiot.*, 2013, 66, 571-591).

*Clostridium difficile*

*C. difficile* is a motile bacterium prevalent in soil, and may become established in the human gut (K. J. Ryan, *Sherris medical microbiology*, 3rd ed. edn., Appleton & Lange, Norwalk, Conn., 1994.) Individuals colonised with the pathogenic strains could remain either asymptomatic or manifest symptoms ranging from self-limiting diarrhoea to the potentially fatal pseudomembranous colitis (E. J. Kuijper, B. Coignard and P. Tüll, *Clin. microbiol. Infect*, 2006, 12, 2-18.)

*C. difficile*-associated disease (CDAD) has emerged as the primary cause of diarrhoea associated with the use of antibiotics. However, the established treatment options are very limited for the management of CDAD. For the past 25 years, the treatment of CDAD has largely relied on metronidazole as the first-line of therapy and vancomycin in severe disease presentations.

*Pseudomonas aeruginosa*

The Gram-negative aerobic *Pseudomonas aeruginosa* is the most common hospital and community-acquired Gram-negative organism. It is the major pathogen responsible for respiratory tract infection in patients suffering from cystic fibrosis (J. C. Davies, *Paediatr. Respir. Rev.*, 3, 128-134).

The European Centre for Disease Prevention and Control has indicated that a high percentage of *P. aeruginosa* strains are resistant to carbapenems, piperacillin/tazobactam, aminoglycosides, ceftazidime and fluoroquinolones, especially in Eastern European countries. Most alarmingly, 5% of the isolates reported were resistant to all five classes of the antibiotics listed above (F. Graham, H. Frantiska, Q. Chantal and A. Catalin, *Annual epidemiological report: Reporting on* 2010 *surveillance data and* 2011 *epidemic intelligence data* 2012).

*Burkholderia cepacia* Complex

*Burkholderia cepacia* complex (Bcc) is a group of Gram-negative, non-spore-forming, motile aerobic bacilli.

Like *P. aeruginosa*, Bcc bacteria are innately resistant to many antibiotics, including aminoglycosides, β-lactams and polymyxins, as well as disinfectants, including povidone iodine and chlorhexidine (D. K. Matthaiou, E. Chasou, S. Atmatzidis and P. Tsolkas, *Resp. Med.*, 2011, 4, 144-145). Their enhanced ability to withstand many antibacterial and disinfectants has made them one of the toughest organisms in clinical and laboratory settings.

Treatment options for Bcc infection remain limited and generally involve careful selection and combination of a handful of antibiotics, such as ceftazidime, meropenem, tobramycin, minocycline and co-trimoxazole (*Clinical and Laboratory Standards Institute: Performance standards for antimicrobial susceptibility testing;* 17*th informational supplement,* 2007).

Therefore, there is an urgent unmet need for new and effective antibiotics to treat infections associated with multidrug resistant bacteria, particularly those caused by *Clostridium difficile Pseudomonas aeruginosa* and/or *Burkholderia cepasia* complex.

SUMMARY OF THE INVENTION

The present invention provides, in a first aspect, a compound of formula (I):

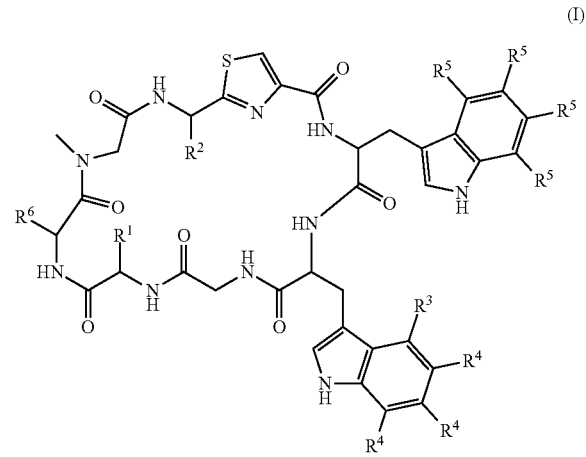

including tautomeric or stereochemically isomeric forms thereof, wherein:

$R^1$ and $R^2$ each independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;

$R^3$ represents halogen;

each $R^4$ and each $R^5$ independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;

$R^6$ represents =$CR^7R^8$, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;

$R^7$ and $R^8$ independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;

each $R^X$ independently represents cyano, halogen, —$B(OR^Y)_2$, —$C(O)R^Y$, —$C(O)OR^Y$, —$OC(O)R^Y$, —$C(O)NHR^Y$, —$NHC(O)R^Y$, —$NHC(O)NHR^Y$, —$NHC(O)OR^Y$, $OC(O)NHR^Y$, $OS(O)_2R^Y$, —$S(O)_2NHR^Y$, —$NHS(O)_2R^Y$, —$NR^Y_2$ or —$OR^Y$; and each $R^Y$ independently represents hydrogen, $C_1$-$C_5$ alkyl, $C_6$-$C_{10}$ aryl, $C_4$-$C_{10}$ heterocyclyl or $C_2$-$C_8$ alkenyl;

or a N-oxide thereof or a pharmaceutically acceptable salt thereof or a pharmaceutically acceptable solvate thereof.

The present inventors have determined that the compounds of the first aspect have particular use in the prevention and treatment of microbial infections. As such, the compounds of the first aspect may be used as antimicrobials, in particular as antibiotics.

In particular, the compounds of the invention are particularly useful in the treatment of an infection caused by *Clostridium difficile*, *Pseudomonas aeruginosa* and/or *Burkholderia cepasia* complex.

In 2002, Sasse et al. reported the discovery and isolation of a family of eight natural cyclic octapeptides (argyrin A-H) as secondary metabolites of a marine myxobacterium, known as *Archnagium gephyra* strain Ar 8082. (F. Sasse, H. Steinmetz, T. Schupp, F. Petersen, K. Memmert, H. Hofmann, C. Heusser, V. Brinkmann, V. Matt P, G. Höfle and H. Reichenbach, *J. Antibiot. (Tokyo).* 2002, 55, 543-551). All argyrins had slight antibiotic activity, especially against *Pseudomonas* sp., and inhibited growth of mammalian cell cultures. The growth inhibition was often incomplete and varied highly with different cell lines The compounds of the first aspect are novel and non-naturally occurring derivatives of these argyrins.

A surprising structure-activity relationship has been determined by the present inventors, which makes the compounds of the first aspect highly selective antibacterial agents, in particular against *Clostridium difficile*, *Pseudomonas aeruginosa* and/or *Burkholderia cepasia* complex. This structure-activity relationship causes the present compounds to not adversely inhibit bacteria commonly associated with healthy gut flora. Such characteristics are particularly beneficial in the treatment of bacterial infections of the gut, as they encourage the formation of a healthy and resilient gut ecosystem during and after treatment. The compounds of the present invention have a halogen group, such as a chloro or bromo group, at the R3 position. This is not present in the naturally occurring argyrins.

The compounds of the present invention have been shown to cause a significant decrease in growth for the *P. aeruginosa*, even for antibiotic resistant strains. The compounds of the present invention have been shown to have an increased activity against *P. aeruginosa* when compared to Argyrin A.

The compounds of the present invention have likewise been shown to be highly active against Bcc organisms.

The compounds of the present invention have further been shown to be narrow spectrum antimicrobials which can selectively inhibit *C. difficile* organisms in vivo. Therefore, the compounds of the invention can be used to treat CDAD in a patient without causing disturbances of the normal dynamics or integrity of gut microbiota.

The compounds of the invention have been shown to have poor gut absorption, meaning that orally administered compounds of the invention will most likely reach high local concentration in the lower intestine, where action against *C. difficile* can be most effective.

Therefore the present invention addresses the need for new antibiotics by providing novel non-natural cyclic peptides for the treatment or prevention of bacterial infections, in particular those caused by a range of Gram-positive and Gram-negative bacteria including strains of *Clostridium difficile* (*C. difficile*), *Pseudomonas aeruginosa* (*P. aeruginosa*) and/or *Burkholderia multivorans* (*B. multivorans*).

Benefits of the compounds of the present invention include one or more of: good efficacy against a range of Gram-positive and Gram-negative bacteria including strains of *Clostridium difficile* (*C. difficile*), *Pseudomonas aeruginosa* (*P. aeruginosa*) and/or *Burkholderia multivorans* (*B. multivorans*); selective activity against bacteria that cause infection as compared to bacteria commonly associated with healthy gut flora; acceptable or good $IC_{50}$ values; good chemical stability in the gastrointestinal tract.

A combination of several beneficial characteristics can make compounds of the present invention highly advantageous candidates for antibiotic use.

According to a second aspect, the invention provides pharmaceutical compositions comprising the compound of the first aspect and a pharmaceutically acceptable carrier or diluent. Optionally the pharmaceutical composition may further comprise, as a further active agent, one or more additional antibiotics.

According to a third aspect, the invention provides compounds according to the first aspect or pharmaceutical compositions according to the second aspect for use in therapy.

According to a fourth aspect, the invention provides compounds according to the first aspect or pharmaceutical compositions according to the second aspect for use as an antibiotic agent. In particular, the use may be as an antibiotic agent against *Clostridium difficile* (*C. difficile*), *Pseudomonas aeruginosa* (*P. aeruginosa*) and/or *Burkholderia multivorans* (*B. multivorans*). The use may be in the treatment or prevention of bacterial infections, in particular those caused by a range of Gram-positive and Gram-negative bacteria including strains of *Clostridium difficile* (*C. difficile*), *Pseudomonas aeruginosa* (*P. aeruginosa*) and/or *Burkholderia multivorans* (*B. multivorans*).

According to a fifth aspect, the invention provides a method of making a pharmaceutical composition according to the second aspect, comprising the step of mixing a compound according to the first aspect with a pharmaceutically acceptable carrier or diluent.

According to a sixth aspect, the invention provides a method of treating individuals suffering from bacterial infection, the method comprising administering an effective amount of a compound according to the first aspect or a pharmaceutical composition according to the second aspect.

According to a seventh aspect, the invention provides a method of treating individuals suffering from bacterial infection comprising i) administering an effective amount of a compound according to the first aspect or a pharmaceutical composition according to the second aspect and ii) simultaneously, sequentially or separately treating the patient with faecal microbiota transplantation.

According to an eighth aspect, the invention provides a method of preventing *Clostridium sordellii* infection in a child-bearing patient, which comprises administering to the patient, for example orally and/or vaginally, an effective dose of according to the first aspect or a pharmaceutical composition according to the second aspect, wherein said administration occurs before, during or after childbirth.

According to a ninth aspect, the invention provides a method of treating individuals suffering from microbial infection comprising i) administering an effective amount of a compound according to the first aspect or a pharmaceutical composition according to the second aspect and ii) simultaneously, sequentially or separately treating the patient with, as further active ingredient, one or more antibiotics which are not compounds of the first aspect.

According to a tenth aspect, the invention provides a pharmaceutical kit comprising (a) the compound of the first aspect and (b) one or more antibiotic which is not a compound of the first aspect, wherein the compound of the first aspect and the one or more antibiotic are for simultaneous, sequential or separate administration to a patient.

BRIEF DESCRIPTION OF THE DRAWINGS

The attached drawings assist with understanding of the invention.

DETAILED DESCRIPTION OF THE INVENTION

Figure 1A:
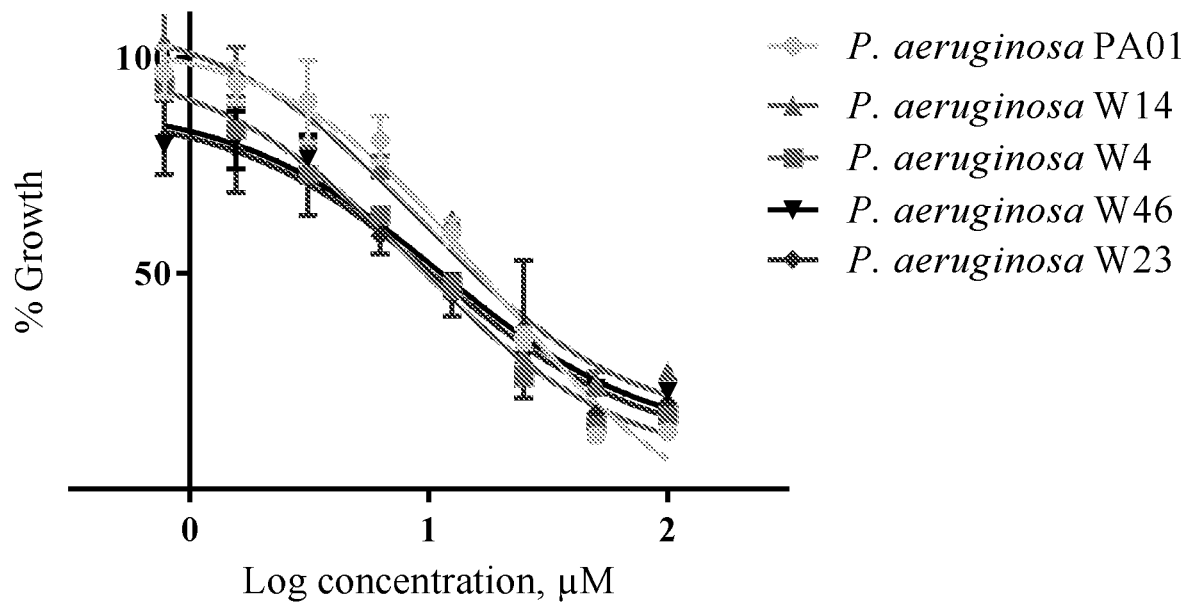
FIGS. 1a and 1b are graphs showing the effects of varying concentrations of compounds 2 and 3 according to the invention on the growth of different strains of *P. aeruginosa* in Müller-Hinton (MH) media, after 13 hours.

Compounds of the present invention have been determined to be useful candidates for antibiotics. In this regard, they may include one or more of: good efficacy against a range of Gram-positive and Gram-negative bacteria including strains of *Clostridium difficile* (*C. Pseudomonas aeruginosa* (*P. aeruginosa*) and/or *Burkholderia multivorans* (*B. multivorans*); selective activity against bacteria that cause infection as compared to bacteria commonly associated with healthy gut flora; acceptable or good $IC_{50}$ values; good chemical stability in the gastrointestinal tract.

Compounds of the invention may be beneficial because they are active against adverse bacteria, such as *C. difficile* and/or *Burkholderia cepacia*, but have low or no activity against normal gut flora. Thus the compounds of the invention are selective antibacterial agents.

In one embodiment the compounds of the invention do not exhibit bacteriostatic and/or bacteriocidal activity against one or more representative(s) of the normal gut flora selected from, but not limited to, *Enterococcus faecalis, Bifidobacterium bifidum, Bifidobacterium breve, Bacteroides fragilis, Corynebacterium urealyticum, Lactobacillus rhamnosus, Staphylococcus aureus, Escherichia coli, Enterococcus faecium, Enterobacter cloacae, Corynebacterium striatium, Actinomyces viscosus, Propionibacterium* and *Corynebacterium jeikeium*.

Compounds of the invention may be active against *Clostridium difficile*, such that they exhibit bacteriostatic and/or bacteriocidal activity against one or more strains of *C. difficile*.

In some embodiments the compounds exhibit bacteriostatic and/or bacteriocidal activity against one or more strains of *C. difficile*, but do not exhibit bacteriostatic and/or bacteriocidal activity (MIC>64 µg/mL) against one or more of the aforementioned representative(s) of the normal gut flora. Thus they are selectively active against *C. difficile*.

The compounds of the invention, which show selective activity against *C. difficile*, are therefore suitable agents to treat *C. difficile*-associated disease (CDAD) to a clinically significant extent, with minimal effects on normal gut faecal microbiota that is essential for maintaining gastrointestinal health. Hence, such agents could be used to treat antibiotic-associated disease caused by *C. difficile*.

Compounds of the invention may be active against *Pseudomonas* spp. Thus the compounds may exhibit bacteriostatic and/or bacteriocidal activity against one or more strains of *Pseudomonas aeruginosa* with minimum inhibitory concentration (MIC) <100 µM or <128 µg/mL.

Compounds of the invention may be active against one or more of *Burkholderia cepacia* complex organisms. Thus the compounds may exhibit bacteriostatic and/or bacteriocidal activity against one or more organism of the Bcc with MIC<100 µM or <128 µg/mL.

The compounds of the invention are of formula (I), including tautomeric or stereochemically isomeric forms thereof, and may be provided in the form of an N-oxide, a pharmaceutically acceptable salt or a pharmaceutically acceptable solvate.

The prefix "$C_{x-y}$" (where x and y are integers) as used herein refers to the number of carbon atoms in a given group. For example, a $C_{1-6}$ alkyl group contains from 1 to 6 carbon atoms, and a $C_{3-6}$ alkyl group contains from 3 to 6 carbon atoms.

The term "alkyl" refers to linear and branched saturated hydrocarbon groups. Examples of such groups include methyl, ethyl, n-propyl, isopropyl, n-butyl, isobutyl, sec-butyl, tert-butyl, n-pentyl, isopentyl, neopentyl or hexyl and the like.

The term "cycloalkyl" refers to cyclic hydrocarbon groups. Examples of such groups include cyclopropyl, cyclobutyl, cyclopentyl, or cyclohexyl and the like.

The term "alkenyl" as used herein refers to a linear or branched hydrocarbon group containing one or more carbon-carbon double bond. Examples of such groups include vinyl, allyl, prenyl, isoprenyl and the like.

The term "aryl" as used herein refers to carbocyclic aromatic groups including phenyl, naphthyl, indenyl, and tetrahydronaphthyl groups.

The term "heterocyclyl" as used herein shall, unless the context indicates otherwise, include both aromatic (i.e. heteroaryl) and non-aromatic ring systems. Thus, for example, the term "heterocyclyl group" includes within its scope aromatic, non-aromatic, unsaturated, partially saturated and fully saturated heterocyclyl ring systems. In general, unless the context indicates otherwise, such groups may be monocyclic or bicyclic and may contain, for example, 4 to 10 ring members, more usually 5 to 10 ring members.

Examples of monocyclic groups are groups containing 4, 5, 6, 7 and 8 ring members, more usually 4 to 7, and preferably 5, 6 or 7 ring members, more preferably 5 or 6 ring members. Examples of bicyclic groups are those containing 8, 9 and 10 ring members. Typical examples of saturated heterocyclic groups include aziridines, oxiranes, pyrrolidines, piperidines, piperazines and decahydroisoquinolines.

The heterocyclyl groups can be heteroaryl groups having from 5 to 10 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

The heteroaryl group can be, for example, a five membered or six membered monocyclic ring or a bicyclic structure formed from fused five and six membered rings or two fused six membered rings. Each ring may contain up to five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. Examples of heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole, pyridine, pyrazine, pyridazine, pyrimidine and triazine groups.

In the compounds of formula (I):
  $R^1$ and $R^2$ each independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;
  $R^3$ represents halogen;
  each $R^4$ and each $R^5$ independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;
  $R^6$ represents $=CR^7R^8$, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;
  $R^7$ and $R^8$ independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$;
  each $R^X$ independently represents cyano, halogen, $-B(OR^Y)_2$, $-C(O)R^Y$, $-C(O)OR^Y$, $-OC(O)R^Y$, $-C(O)NHR^Y$, $-NHC(O)R^Y$, $-NHC(O)NHR^Y$, $-NHC(O)OR^Y$, $OC(O)NHR^Y$, $OS(O)_2R^Y$, $-S(O)_2NHR^Y$, $-NHS(O)_2R^Y$, $-NR^Y_2$ or $-OR^Y$; and
  each $R^Y$ independently represents hydrogen, $C_1$-$C_8$ alkyl, $C_6$-$C_{10}$ aryl, $C_4$-$C_{10}$ heterocyclyl or $C_2$-$C_8$ alkenyl.

The alkyl, alkenyl, aryl and/or heterocyclyl groups of the compounds of the invention may be substituted by one or more $R^X$ groups, as defined herein. For example, the alkyl, alkenyl, aryl and/or heterocyclyl groups of the compounds of the invention may be substituted by two or more, or three or more $R^X$ groups. The alkyl, alkenyl, aryl and/or heterocyclyl groups of the compounds of the invention may be substituted by four or less, such as three or less, for example two or less $R^X$ groups, i.e. only one or two $R^X$ groups. In one embodiment, the alkyl, alkenyl, aryl and/or heterocyclyl groups of the compounds of the invention are not substituted by any $R^X$ groups. Thus the alkyl, alkenyl, aryl and/or heterocyclyl groups are unsubstituted.

The terms "halo" and "halogen" as used herein refers to a fluorine, chlorine, bromine or iodine atom. In one embodiment, the halogen group is fluorine, chlorine or bromine. In another embodiment, it is chlorine or bromine.

In the compounds of the invention, $R^1$ represents hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$.

Preferably the $R^1$ group has a total of eight or fewer carbon atoms, such as from 1 to 6 carbon atoms or from 1 to 4 carbon atoms.

In one embodiment, $R^1$ represents hydrogen, $C_1$-$C_8$ alkyl optionally substituted by one or more $R^X$ groups (e.g. substituted with $-OR^Y$, such as $-OH$ or $-OMe$ or $-OEt$), $C_3$-$C_8$ cycloalkyl optionally substituted by one or more $R^X$ groups (e.g. substituted with $-OR^Y$, such as $-OH$ or $-OMe$ or $-OEt$), $C_2$-$C_8$ alkenyl optionally substituted by one or more $R^X$ groups (e.g. substituted with $-OR^Y$, such as $-OH$ or $-OMe$ or $-OEt$), or $R^X$ (where $R^X$ may, for example be $-OMe$ or halogen, e.g. chloride or bromide).

In one embodiment, $R^1$ represents hydrogen, $C_1$-$C_6$ alkyl optionally substituted by one or more $R^X$ groups (e.g. substituted with $-OR^Y$, such as $-OH$ or $-OMe$ or $-OEt$), or $C_2$-$C_6$ alkenyl optionally substituted by one or more $R^X$ groups (e.g. substituted with $-OR^Y$, such as $-OH$ or $-OMe$ or $-OEt$).

In one embodiment, $R^1$ represents hydrogen, $C_1$-$C_4$ alkyl optionally substituted by one or more $R^X$ groups (e.g. unsubstituted or substituted by one or two $R^X$ groups) or $C_2$-$C_4$ alkenyl optionally substituted by one or more $R^X$ groups (e.g. unsubstituted or substituted by one or two $R^X$ groups), where the $R^X$ groups may be $-OR^Y$, such as $-OH$ or $-OMe$ or $-OEt$.

For example, in one embodiment $R^1$ represents hydrogen or $C_1$-$C_4$ alkyl. In one embodiment, $R^1$ represents hydrogen or methyl or ethyl, e.g. hydrogen or methyl.

$R^2$ represents hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$.

Preferably the $R^2$ group has a total of eight or fewer carbon atoms, such as from 1 to 6 carbon atoms or from 1 to 4 carbon atoms.

In one embodiment, $R^2$ represents hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, or $R^X$ (where $R^X$ may, for example be —OMe or halogen, e.g. chloride or bromide).

In one embodiment, $R^2$ represents hydrogen, $C_1$-$C_6$ alkyl optionally substituted by one or more $R^X$ groups (e.g. substituted with —$OR^Y$, such as —OH or —OMe or —OEt), or $C_2$-$C_6$ alkenyl optionally substituted by one or more $R^X$ groups (e.g. substituted with —$OR^Y$, such as —OH or —OMe or —OEt).

In one embodiment, $R^2$ represents hydrogen, $C_1$-$C_4$ alkyl optionally substituted by one or more $R^X$ groups (e.g. unsubstituted or substituted by one or two $R^X$ groups) or $C_2$-$C_4$ alkenyl optionally substituted by one or more $R^X$ groups (e.g. unsubstituted or substituted by one or two $R^X$ groups). The $R^X$ group or groups may suitably be —$OR^Y$, such as —OH or —OMe or —OEt.

For example, in one preferred embodiment $R^2$ represents $C_1$-$C_4$ alkyl optionally substituted by one or more $R^X$ groups, or $C_2$-$C_4$ alkenyl optionally substituted by one or more $R^X$ groups, wherein the $R^X$ group or groups may suitably be —$OR^Y$, such as —OH or —OMe or —OEt.

In one embodiment, $R^2$ represents $C_1$-$C_3$ alkyl optionally substituted by one $R^X$ group, or $C_2$-$C_4$ alkenyl optionally substituted by one $R^X$ group, wherein the $R^X$ group is —$OR^Y$, such as —OH or —OMe or —OEt.

In one embodiment, $R^2$ is methyl or hydroxymethyl or methoxymethyl.

$R^3$ represents a halogen group. Therefore $R^3$ may be fluoride, chloride, bromide or iodide. In one embodiment, it is fluoride, chloride or bromide.

In one embodiment, $R^3$ represents bromide or chloride.

Each $R^4$ independently represents hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$.

It will be understood that all $R^4$ groups have been grouped together for conciseness and that, if required, one or more instances of $R^4$ may be limited independently of other $R^4$ groups. In this case the independent limited groups will be known as $R^{4-1}$, $R^{4-2}$ and so on.

Preferably each $R^4$ group has a total of eight or fewer carbon atoms, such as from 0 to 6 carbon atoms or from 0 to 4 carbon atoms.

It will be noted that there are a total of three $R^4$ groups. In one embodiment at least one $R^4$ group is hydrogen. In one embodiment at least two $R^4$ groups are hydrogen, for example exactly two $R^4$ groups are hydrogen and one is not hydrogen.

It may be that all three $R^4$ groups are hydrogen.

In one embodiment, each $R^4$ independently represents hydrogen, $C_1$-$C_8$ alkyl optionally substituted by one or more $R^X$ groups, $C_3$-$C_8$ cycloalkyl optionally substituted by one or more $R^X$ groups, or $R^X$. In one embodiment, each $R^4$ independently represents hydrogen, $C_1$-$C_6$ alkyl optionally substituted by one or more $R^X$ groups (e.g. unsubstituted or substituted by one or two $R^X$ groups), $C_3$-$C_6$ cycloalkyl optionally substituted by one or more $R^X$ groups (e.g. unsubstituted or substituted by one or two $R^X$ groups), or $R^X$.

In a preferred embodiment, each $R^4$ independently represents hydrogen or $C_1$-$C_4$ alkyl or $R^X$. In one preferred embodiment, each $R^4$ independently represents hydrogen or $R^X$. In another preferred embodiment, each $R^4$ independently represents hydrogen or $C_1$-$C_4$ alkyl or halogen or —$OR^Y$. In another preferred embodiment, each $R^4$ independently represents hydrogen or methyl or —OMe or halogen (e.g. chloride or bromide).

In one embodiment, two $R^4$ groups are hydrogen and one is methyl or —OMe or halogen (e.g. chloride or bromide).

Each $R^5$ independently represents hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$.

It will be understood that all $R^5$ groups have been grouped together for conciseness and that, if required, one or more instances of $R^5$ may be limited independently of other $R^5$ groups. In this case the independent limited groups will be known as $R^{5-1}$, $R^{5-2}$ and so on.

Preferably each $R^5$ group has a total of eight or fewer carbon atoms, such as from 0 to 6 carbon atoms or from 0 to 4 carbon atoms.

It will be noted that there are a total of four $R^5$ groups. In one embodiment at least one $R^5$ group is hydrogen. In one embodiment at least two $R^5$ groups are hydrogen, for example exactly two $R^5$ groups are hydrogen and two are not hydrogen. In one embodiment at least three $R^5$ groups are hydrogen, for example exactly three $R^5$ groups are hydrogen and one is not hydrogen.

It may be that all four $R^5$ groups are hydrogen.

In one embodiment, each $R^5$ independently represents hydrogen, $C_1$-$C_8$ alkyl optionally substituted by one or more $R^X$ groups, $C_3$-$C_8$ cycloalkyl optionally substituted by one or more $R^X$ groups, or $R^X$. In one embodiment, each $R^5$ independently represents hydrogen, $C_1$-$C_6$ alkyl optionally substituted by one or more $R^X$ groups (e.g. unsubstituted or substituted by one or two $R^X$ groups), $C_3$-$C_6$ cycloalkyl optionally substituted by one or more $R^X$ groups (e.g. unsubstituted or substituted by one or two $R^X$ groups), or $R^X$.

In a preferred embodiment, each $R^5$ independently represents hydrogen or $C_1$-$C_4$ alkyl or $R^X$. In one preferred embodiment, each $R^5$ independently represents hydrogen or $R^X$. In another preferred embodiment, each $R^5$ independently represents hydrogen or $C_1$-$C_4$ alkyl or halogen or —$OR^Y$. In another preferred embodiment, each $R^5$ independently represents hydrogen or methyl or —OMe or halogen (e.g. chloride or bromide).

In one embodiment, three $R^5$ groups are hydrogen and one is methyl or —OMe or halogen (e.g. chloride or bromide).

$R^6$ represents =$CR^7R^8$, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$.

Preferably the $R^6$ group has a total of ten or fewer carbon atoms, such as from 1 to 8 carbon atoms or from 1 to 6 carbon atoms or from 1 to 4 carbon atoms.

It will be understood that when $R^6$ is "=$CR^7R^8$", there will be a double bond between the carbon of the core of the molecule that the $R^6$ group is bonded to and the =$CR^7R^8$ group itself. This produces the alkene shown at the $R^6$ position in compounds 1-8 and 10-14 of Table 1. The cis and trans isomers of this alkene are both covered by formula (I). In one embodiment, the cis isomer is preferred. In one embodiment, the trans isomer is preferred.

In one embodiment, $R^6$ represents $=CR_7R_8$, $C_2$-$C_6$ alkenyl optionally substituted by one or more $R^X$ groups, $C_6$-$C_8$ aryl optionally substituted by one or more $R^X$ groups, $C_4$-$C_8$ heterocyclyl optionally substituted by one or more $R^X$ groups, or $R^X$.

In one embodiment, $R^6$ represents $=CR_7R_8$, $C_2$-$C_6$ alkenyl optionally substituted by one or more $R^X$ groups (e.g. unsubstituted or substituted by one or two $R^X$ groups), or $C_6$-$C_8$ aryl optionally substituted by one or more $R^X$ groups (e.g. unsubstituted or substituted by one or two $R^X$ groups).

In a preferred embodiment, $R^6$ represents $=CR^7R^8$.

$R^7$ and $R^8$ independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, $C_4$-$C_{10}$ heterocyclyl optionally substituted by one or more $R^X$ groups, or $R^X$.

It may be that one alkyl, cycloalkyl, alkenyl or heterocyclyl group is shared between the $R^7$ and $R^8$ groups. In this case a ring would be formed with an exocyclic double bond. The skilled person will understand that $R^7$ and $R^8$ are interchangeable but may each have independent functionality.

Preferably the $R^7$ and the $R^8$ group each independently have a total of eight or fewer carbon atoms, such as from 0 to 6 carbon atoms or from 0 to 4 carbon atoms. Preferably the $R^7$ and the $R^8$ group together in total have a total of eight or fewer carbon atoms, such as from 0 to 6 carbon atoms or from 0 to 4 carbon atoms.

In one embodiment $R^7$ and $R^8$ each independently represent hydrogen, $C_1$-$C_8$ alkyl optionally substituted by one or more $R^X$ groups, $C_3$-$C_8$ cycloalkyl optionally substituted by one or more $R^X$ groups, $C_2$-$C_8$ alkenyl optionally substituted by one or more $R^X$ groups, $C_6$-$C_{10}$ aryl optionally substituted by one or more $R^X$ groups, or $C_4$-$C_{10}$ heterocyclyl optionally substituted by one or more $R^X$ groups.

In one embodiment $R^7$ and $R^8$ independently represent hydrogen, $C_1$-$C_6$ alkyl optionally substituted by one or more $R^X$ groups (e.g. unsubstituted or substituted by one or two $R^X$ groups), $C_2$-$C_6$ alkenyl optionally substituted by one or more $R^X$ groups (e.g. unsubstituted or substituted by one or two $R^X$ groups), or $C_3$-$C_6$ cycloalkyl optionally substituted by one or more $R^X$ groups (e.g. unsubstituted or substituted by one or two $R^X$ groups).

It may be that $R^7$ and $R^8$ independently represent hydrogen, $C_1$-$C_6$ alkyl optionally substituted by one or more $R^X$ groups (e.g. unsubstituted or substituted by one or two $R^X$ groups), or $C_2$-$C_6$ alkenyl optionally substituted by one or more $R^X$ groups (e.g. unsubstituted or substituted by one or two $R^X$ groups).

In one embodiment $R^7$ and $R^8$ independently represent hydrogen or $C_1$-$C_6$ alkyl optionally substituted by one or more $R^X$ groups (e.g. unsubstituted or substituted by one or two $R^X$ groups), e.g. they may each independently represent hydrogen or methyl or ethyl.

In one embodiment $R^7$ represents hydrogen and $R^8$ represents hydrogen, $C_1$-$C_6$ alkyl optionally substituted by one or more $R^X$ groups (e.g. unsubstituted or substituted by one or two $R^X$ groups), $C_2$-$C_6$ alkenyl optionally substituted by one or more $R^X$ groups (e.g. unsubstituted or substituted by one or two $R^X$ groups), or $C_3$-$C_6$ cycloalkyl optionally substituted by one or more $R^X$ groups (e.g. unsubstituted or substituted by one or two $R^X$ groups). In one preferred embodiment $R^7$ represents hydrogen and $R^8$ represents hydrogen or $C_1$-$C_6$ alkyl optionally substituted by one or more $R^X$ groups (e.g. unsubstituted or substituted by one or two $R^X$ groups), e.g. $R^8$ may represent hydrogen or methyl or ethyl.

Each $R^X$ independently represents cyano, halogen, $-B(OR^Y)_2$, $-C(O)R^Y$, $-C(O)OR^Y$, $-OC(O)R^Y$, $-C(O)NHR^Y$, $-NHC(O)R^Y$, $-NHC(O)NHR^Y$, $-NHC(O)OR^Y$, $OC(O)NHR^Y$, $OS(O)_2R^Y$, $-S(O)_2NHR^Y$, $-NHS(O)_2R^Y$, $-NR^Y_2$ or $-OR^Y$.

It will be understood that all $R^X$ groups have been grouped together for conciseness and that, if required, one or more instances of $R^X$ may be limited independently of other $R^X$ groups. In this case the independent limited groups will be known as $R^{X1}$, $R^{X2}$ and so on.

In one embodiment each $R^X$ independently represents cyano, halogen (e.g. chloride or bromide), $-C(O)R^Y$, $-C(O)OR^Y$, $-OC(O)R^Y$, $-C(O)NHR^Y$, $-NHC(O)R^Y$, $-NR^Y_2$ or $-OR^Y$.

In one embodiment each $R^X$ independently represents cyano, halogen (e.g. chloride or bromide), $-NR^Y_2$ or $-OR^Y$.

In one embodiment each $R^X$ independently represents cyano, chloride or bromide, $-NH_2$, $-NMe_2$ or $-OH$ or OMe.

Each $R^Y$ independently represents hydrogen, $C_1$-$C_8$ alkyl, $C_6$-$C_{10}$ aryl, $C_4$-$C_{10}$ heterocyclyl or $C_2$-$C_8$ alkenyl. It will be understood that where two $R^Y$ groups are bonded to the same carbon atom or heteroatom, one $R^Y$ group may link both groups. In this case, a ring will be formed.

It will be understood that all $R^Y$ groups have been grouped together for conciseness and that, if required, one or more instances of $R^Y$ may be limited independently of other $R^Y$ groups. In this case the independent limited groups will be known as $R^{Y1}$, $R^{Y2}$ and so on.

In one embodiment, each $R^Y$ independently represents hydrogen, $C_1$-$C_6$ alkyl, $C_6$-$C_{10}$ aryl, $C_4$-$C_7$ heterocyclyl or $C_2$-$C_6$ alkenyl.

In one embodiment, each $R^Y$ independently represents hydrogen or $C_1$-$C_6$ alkyl, e.g. hydrogen, methyl or ethyl.

In one preferred embodiment:
  $R^1$ represents hydrogen or $C_1$-$C_4$ alkyl;
  $R^2$ represents $C_1$-$C_4$ alkyl optionally substituted by one or more $R^X$ groups, or $C_2$-$C_4$ alkenyl optionally substituted by one or more $R^X$ groups, wherein the $R^X$ group or groups may suitably be $-OR^Y$, such as $-OH$ or $-OMe$ or $-OEt$;

$R^3$ represents bromide or chloride or fluoride (e.g. chloride or bromide);

each $R^4$ independently represents hydrogen or methyl or —OMe or halogen (e.g. chloride or bromide);

each $R^5$ independently represents hydrogen or methyl or —OMe or halogen (e.g. chloride or bromide);

$R^6$ represents $=CR^7R^8$, where $R^7$ and $R^8$ independently represent hydrogen, $C_1$-$C_6$ alkyl optionally substituted by one or more $R^X$ groups (e.g. unsubstituted or substituted by one or two $R^X$ groups), $C_2$-$C_6$ alkenyl optionally substituted by one or more $R^X$ groups (e.g. unsubstituted or substituted by one or two $R^X$ groups).

In one preferred embodiment:

$R^1$ represents hydrogen or $C_1$-$C_4$ alkyl;

$R^2$ represents $C_1$-$C_3$ alkyl optionally substituted by one $R^X$ group, or $C_2$-$C_4$ alkenyl optionally substituted by one $R^X$ group, wherein the $R^X$ group is —$OR^Y$, such as —OH or —OMe or —OEt;

$R^3$ represents bromide or chloride;

each $R^4$ independently represents hydrogen or methyl or —OMe or chloride or bromide;

each $R^5$ independently represents hydrogen or methyl or —OMe or halogen or chloride or bromide;

$R^6$ represents $=CR^7R^8$, where $R^7$ and $R^8$ independently represent hydrogen, or $C_1$-$C_4$ alkyl or $C_2$-$C_4$ alkenyl.

In one embodiment, the compound is of formula (IA):

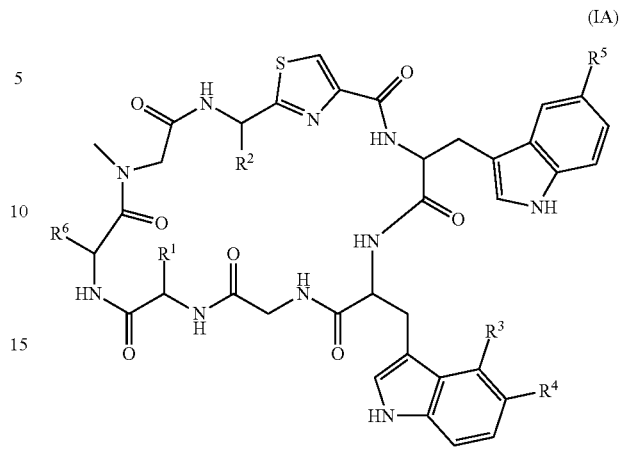

(IA)

where the definitions of the substituent groups are as stated above.

Some preferred compounds of Formula (I) are listed in Table 1. While stereochemical information relating to these compounds is shown, Formula (I) is not limited to any particular stereoisomer and alternative stereoisomer configurations to those shown in Table 1 are hereby disclosed and contemplated for use.

However, in one embodiment, the stereoisomer configurations as shown in Table 1 are used.

TABLE 1

| Name | Structure |
|---|---|
| Compound 1 | Cyclo[D-Ser(OMe)-Thz-Trp-Trp(4-Br)-Gly-D-Ala-Dha-Sar] |
| Compound 2 | Cyclo[D-Ala-Thz-Trp-Trp(4-Cl)-Gly-D-Ala-Dha-Sar ] |

TABLE 1-continued

| Name | | Structure |
|---|---|---|
| Compound 3 | Cyclo[D-Ala-Thz-Trp-Trp(4-Br)-Gly-D-Ala-Dha-Sar] | 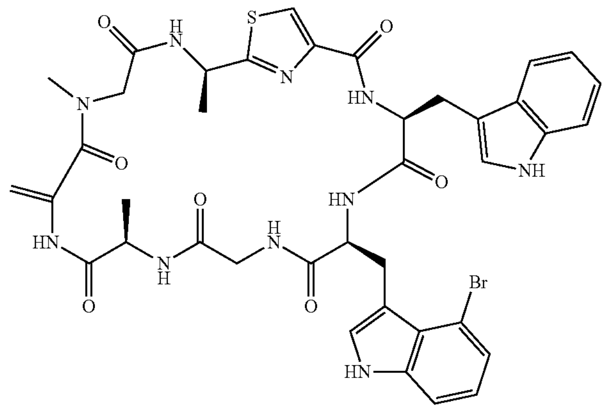 [SMILES: C=C1NC(=O)[C@@H](C)NC(=O)CNC(=O)[C@H](Cc2c[nH]c3cccc(Br)c23)NC(=O)[C@H](Cc2c[nH]c3ccccc23)NC(=O)c2csc(n2)[C@@H](C)NC(=O)CN(C)C1=O] |
| Compound 4 | Cyclo[D-Ala-Thz-Trp-Trp(4-F)-Gly-D-Ala-Dha-Sar] | 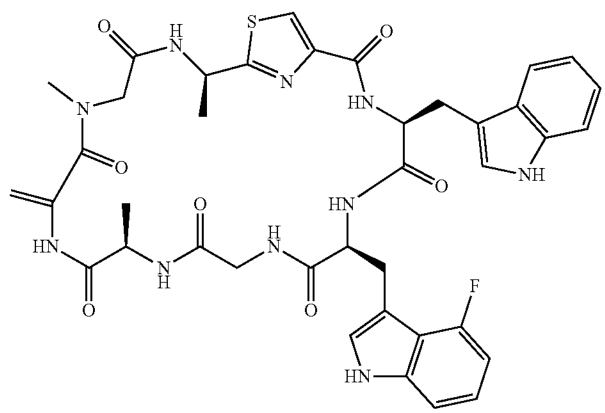 [SMILES: C=C1NC(=O)[C@@H](C)NC(=O)CNC(=O)[C@H](Cc2c[nH]c3cccc(F)c23)NC(=O)[C@H](Cc2c[nH]c3ccccc23)NC(=O)c2csc(n2)[C@@H](C)NC(=O)CN(C)C1=O] |
| Compound 5 | Cyclo[D-Ala-Thz-Trp-Trp(4-CF$_3$)-Gly-D-Ala-Dha-Sar] | 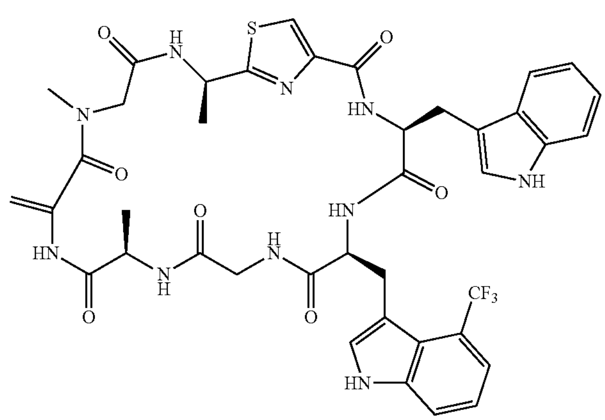 |

TABLE 1-continued

| Name | | Structure |
|---|---|---|
| Compound 6 | Cyclo[D-Ala-Thz-Trp-Trp(4,5-Cl)-Gly-D-Ala-Dha-Sar] | 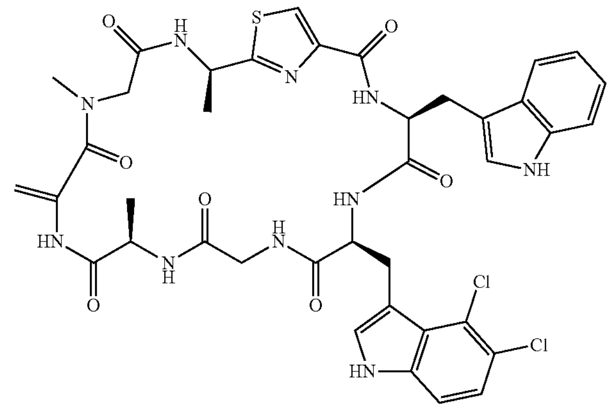 [SMILES: C=C1NC(=O)[C@@H](C)NC(=O)CNC(=O)[C@H](Cc2c[nH]c3ccc(Cl)c(Cl)c23)NC(=O)[C@H](Cc2c[nH]c3ccccc23)NC(=O)c2csc(n2)[C@@H](C)NC(=O)CN(C)C1=O] |
| Compound 7 | Cyclo[D-Ala-Thz-Trp-Trp(4-Cl)-Gly-D-Ala-Thr-Sar] | 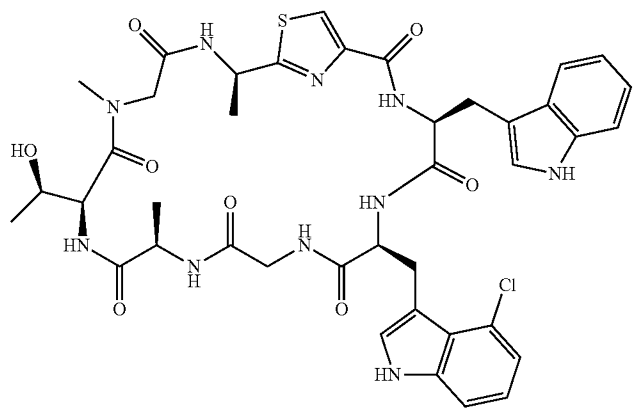 [SMILES: C[C@H]1NC(=O)CNC(=O)[C@H](Cc2c[nH]c3cccc(Cl)c23)NC(=O)[C@H](Cc2c[nH]c3ccccc23)NC(=O)c2csc(n2)[C@@H](C)NC(=O)CN(C)C(=O)[C@H]([C@@H](C)O)NC1=O] |
| Compound 8 | Cyclo[D-Ser-Thz-Trp-Trp(4-Cl)-Gly-D-Ala-Dha-Sar] | 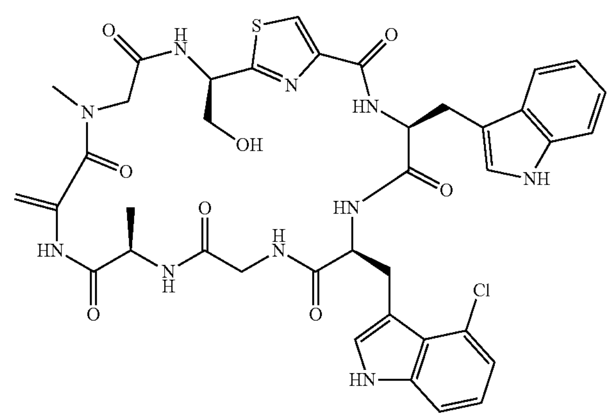 [SMILES: C=C1NC(=O)[C@@H](C)NC(=O)CNC(=O)[C@H](Cc2c[nH]c3cccc(Cl)c23)NC(=O)[C@H](Cc2c[nH]c3ccccc23)NC(=O)c2csc(n2)[C@@H](CO)NC(=O)CN(C)C1=O] |

TABLE 1-continued

| Name | | Structure |
|---|---|---|
| Compound 9 | Cyclo[D-Ala-Thz-Trp-Trp(4-Cl)-Gly-D-Ala-Dhb-Sar] | 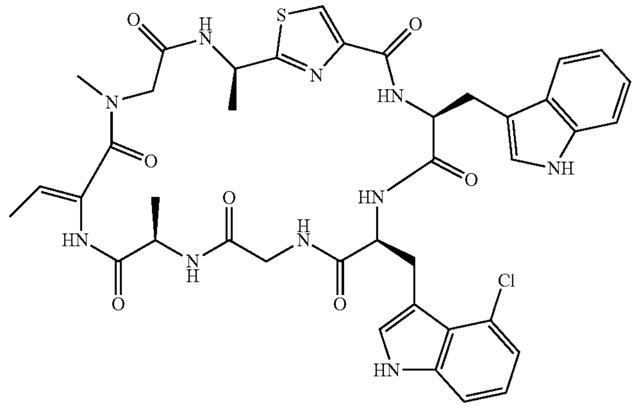 |
| Compound 10 | Cyclo[D-Ala-Thz-Trp-Trp(4-Br)-Gly-D-Ala-Dhb-Sar] | 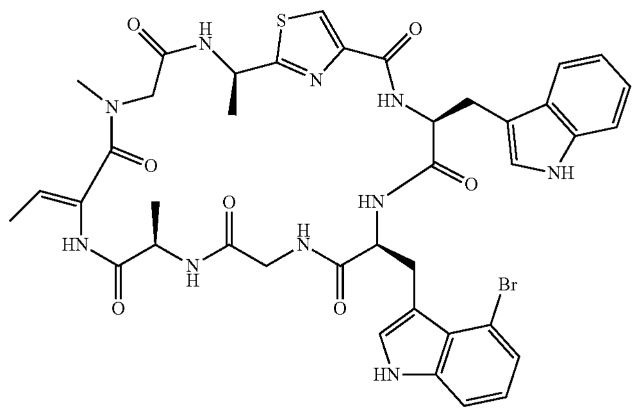 [SMILES: C/C=C1\NC(=O)[C@@H](C)NC(=O)CNC(=O)[C@H](Cc2c[nH]c3cccc(Cl)c23)NC(=O)[C@H](Cc2c[nH]c3ccccc23)NC(=O)c2csc(n2)[C@@H](C)NC(=O)CN(C)C1=O] |
| Compound 11 | Cyclo[D-Ser(OMe)-Thz-Trp-Trp(4-Br)-Gly-D-Ala-Dhb-Sar] | 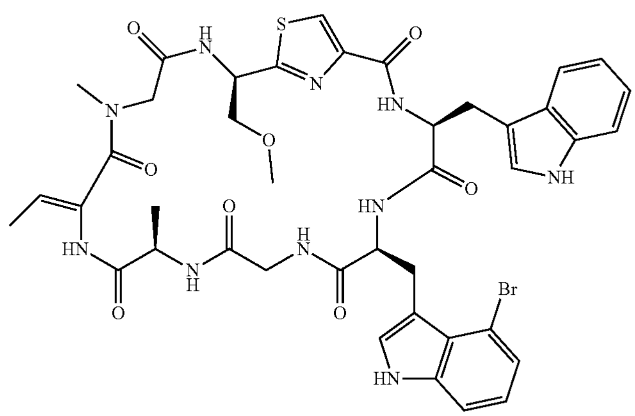 [SMILES: C/C=C1\NC(=O)[C@@H](C)NC(=O)CNC(=O)[C@H](Cc2c[nH]c3cccc(Br)c23)NC(=O)[C@H](Cc2c[nH]c3ccccc23)NC(=O)c2csc(n2)[C@@H](COC)NC(=O)CN(C)C1=O] |
| Compound 12 | Cyclo[D-Ala-Thz-Trp-Trp(4-Br)-Gly-D-Ala-Dhp-Sar] | 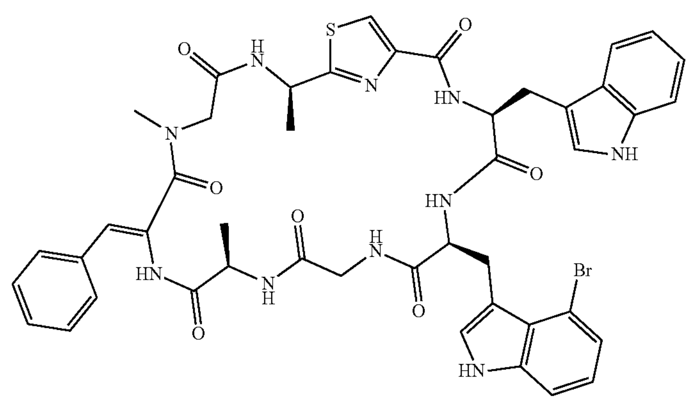 [SMILES: C[C@H]1NC(=O)CNC(=O)[C@H](Cc2c[nH]c3cccc(Br)c23)NC(=O)[C@H](Cc2c[nH]c3ccccc23)NC(=O)c2csc(n2)[C@@H](C)NC(=O)CN(C)C(=O)/C(=C/c2ccccc2)NC1=O] |

TABLE 1-continued

| Name | Structure |
|---|---|
| Compound 13  Cyclo[D-Ala-Thz-Trp-Trp(4-Br)-Gly-D-Ala-Dhv-Sar ] | |
| Compound 14  Cyclo[D-Ala-Thz-Trp-Trp(4-Br)-Gly-D-Ala-Dhl-Sar] | |

Use of Compounds of the Invention in Combination Therapy

The compound according to the present invention may be used together with one or more other medicinal agents.

For example, as noted above, the present invention relates to a method of treatment involving use, as a first active ingredient, of a compound according to the invention and, as further active ingredient, one or more additional antibiotics. These may be used as a combined preparation for simultaneous, sequential or separate use in the treatment of patients with microbial infections.

As such, the compounds of the invention could be used in combination therapy, e.g. to treat *C. difficile* infection.

Any antibiotic may be used in such a combination therapy, such as one or more glycopeptides (c.a. vancomycin, oritavancin, telavancin), lipoglycopeptides (e.g. daptomycin or related antibiotics), nitroaromatic antibiotics (e.g. metronidazole, nitazoxanide or antibiotics classified as nitrofurans or nitroimidazoles), macrolides (e.g. fidaxomicin), fusidic acid or rifamycins (e.g. rifaxiniin, rifalazil) or lantibiotics (e.g. actagardine).

Combination treatments may be necessary or appropriate where a compound of the invention is used as a prophylaxis to suppress *C. difficile* infection and a broad spectrum antibiotic is used to treat a systematic infection.

Fecal microbiota transplantation (FMT) is a treatment involving the transplantation of fecal material from the gut of a healthy individual into the gut of a patient. Studies have shown good results in the treatment of recurrent *C. difficile* in adults using FMT. Administration of donor fecal microbiota typically occurs externally, for example orally or anally, through enema, endoscopy or through a nasogastric or nasoduodenal tube.

It is envisaged that the compounds of the present invention may be used in combination with biotherapeutics, such as probiotics, FMT or specific microbiome organisms such as, but not limited to, *Clostridium scindens, Pseudoflavonifractor capillosus, Blautia hansenii* and *Barnesiella intestihominis*, and/or with toxin binding polymers (e.g. tolevamer).

The one or more other medicinal agents and the compound according to the present invention may be administered simultaneously (e.g. in separate compositions or via a single composition) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular condition being treated and the particular patient being treated. The optimum method and order of administration and the dosage amounts and regime can be readily determined by those skilled in the art using conventional methods and in view of the information set out herein.

Pharmaceutical Compositions

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration.

These pharmaceutical compositions may be suitable for administration orally; rectally, for example, by enema, suppository or catheter; or nasally, for example, endoscopically through a nasogastric or nasoduodenal tube.

For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is to be administered in an amount sufficient to exert its antimicrobial, in particular, antibiotic activity.

The compounds according to the invention may be administered to a human or to an animal, which may be a mammal, e.g. it may be a farm animal or an animal kept as a pet, such as a dog, cat or horse.

The present invention further relates to the use of a compound according to the invention in the manufacture of a pharmaceutical composition. The pharmaceutical composition may, for example, be for use an antimicrobial, in particular an antibiotic, i.e. for inhibiting the growth of bacteria.

Preparation of Compounds

It should be understood that the following syntheses could be readily adopted and modified by the skilled person in order to synthesise other compounds of the present invention.

Unlike the solution-phase convergent macrocycle-assembly strategy reported so far (S. V. Ley, A. Priour and C. Heusser, *Org. Lett.*, 2002, 4, 711-714; W. Wu, Z. Li, G. Zhou and S. Jiang, *Tetrahedron Lett.*, 2011, 52, 2488-2491; L. Büllow, I. Nickeleit, A.-K. Girbig, T. Brodmann, A. Rentsch, U. Eggert, F. Sasse, H. Steinmetz, R. Frank, T. Carlomagno, N. P. Malek and M. Kalesse, *ChemMedChem*, 2010, 5, 832-836) this invention utilised the Fmoc/tBu solid-phase peptide synthesis (SPPS) for the stepwise assembly of the linear peptide acid precursor, followed by solution-phase macrocyclisation to achieve the macrocyclic compounds.

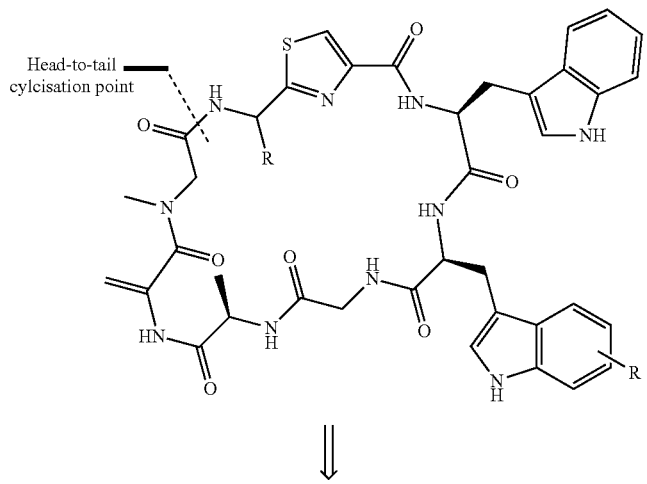

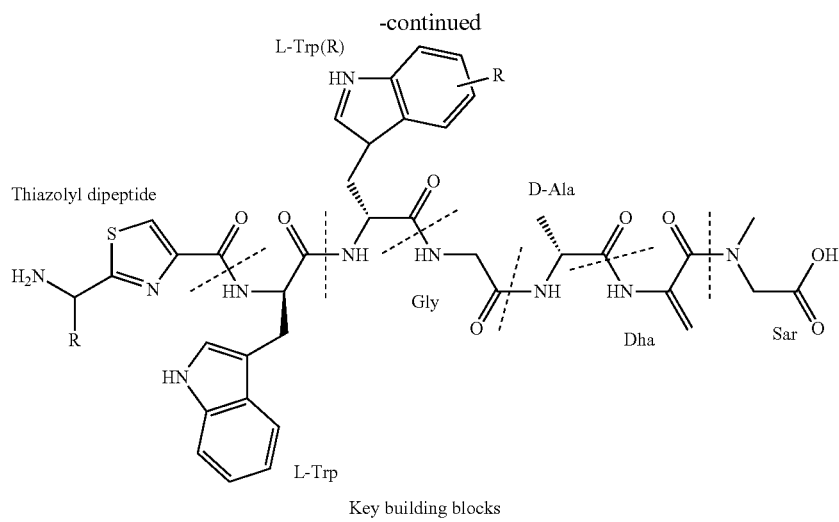

Key building blocks

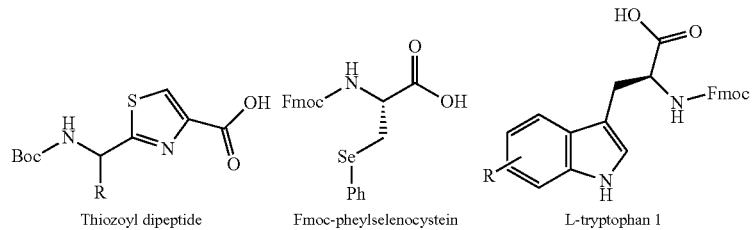

The amino acid residues of natural argyrins A-H are sarcosine (Sar), dehydroalanine (Dha), dehydroaminobutyric acid (Dhb), D-Ala, Gly, L-Trp and a thiazolyl dipeptide. Of these, the thiazolyl dipeptide, Dha, Dhb and the L-Trp(R) residues are uncommon and/or commercially unavailable.

Therefore, the thiazolyl dipeptide was prepared by manipulation of Schmidt's modified Hantzsch thiazole synthesis, as depicted in Scheme 1 (E. Aguilar and A. I. Meyers, *Tetrahedron. Lett.*, 1994, 35, 2473-2476).

For the synthesis of methyl- and hydroxymethyl-containing thiazolyl dipeptides, N-Boc-D-Ala and N-Boc-O-tert-butyl-D-Ser were used as the starting materials.

The synthesis of D-allylglycine (Alg)-containing dipeptides was prepared from N-Boc-D-allylglycine.

Scheme 1: Schmidt's modified Hantzsch thiazole synthesis.

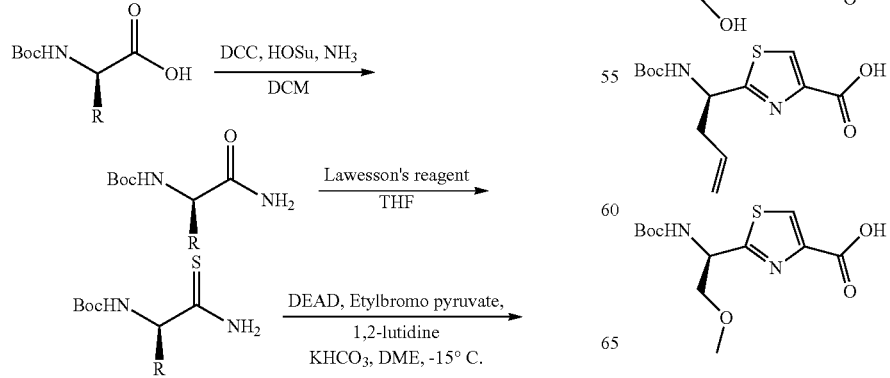

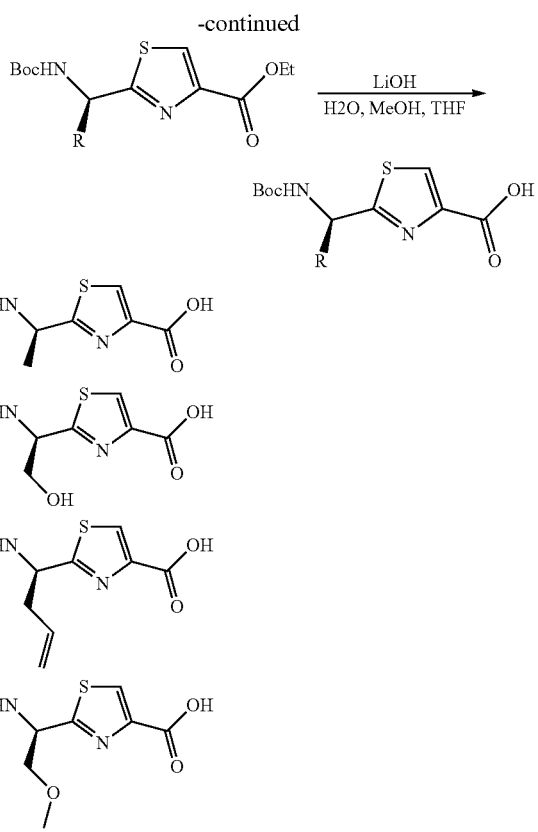

The Dha moiety is predicted to be unstable under the standard conditions of Fmoc/tBu SPPS strategy. Therefore, phenylselenocysteine (Sec(Ph)) was used as a suitable precursor which was effectively eliminated to produce the exo-methylene moiety at a later stage in the synthesis.

The Sec(Ph) was prepared (Scheme 2) following previously reported method by Okeley et al (N. M. Okeley, Y. Zhu and W. A. van der Donk, *Org. Lett.*, 2000, 2, 3603-3606).

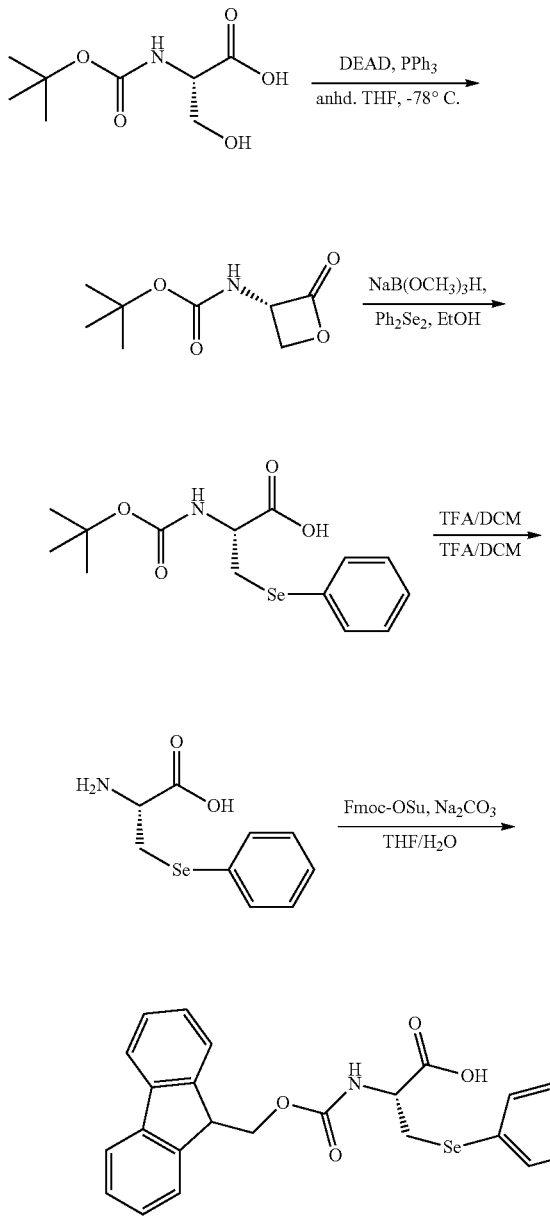

Preparation of L-Tryptophan Analogues 1

Although many useful methods are available for the synthesis of optically pure tryptophan derivatives, they generally lack versatility or efficiency. Hence, a more robust, modular and efficient method is established, which comprises stereoselective homologation of intermediate 5 with a chiral auxiliary. The intermediate 5 can be synthesised in very good yield as outlined in Scheme 3.

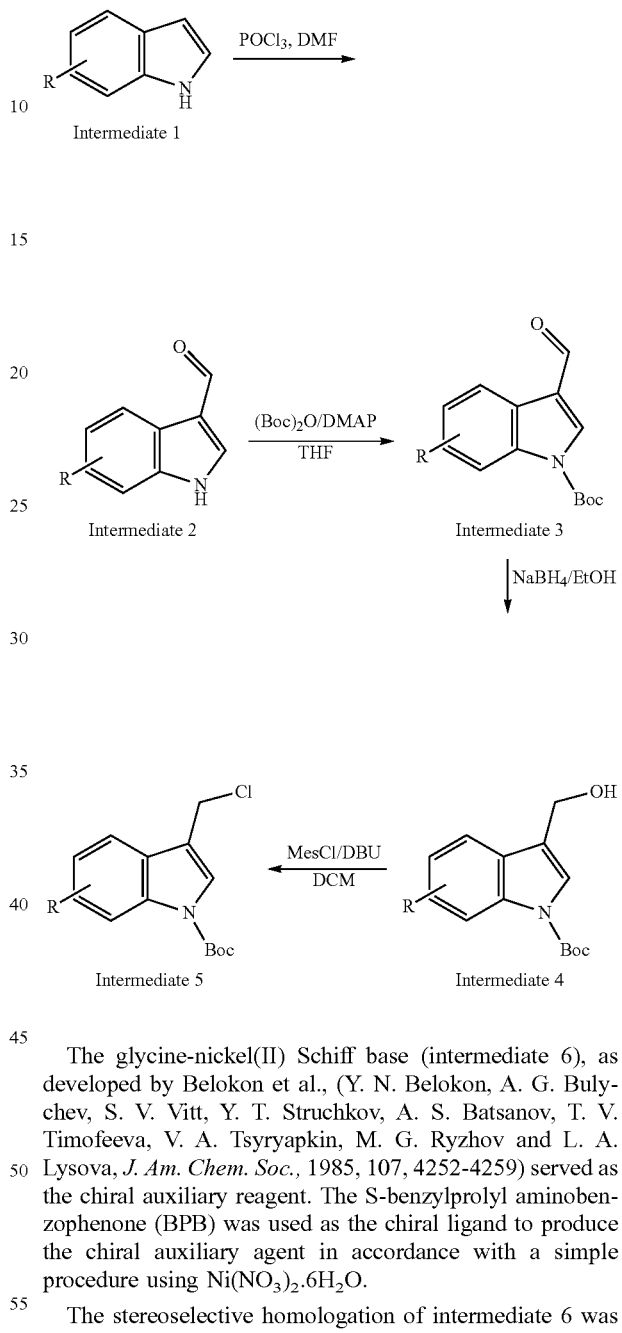

The glycine-nickel(II) Schiff base (intermediate 6), as developed by Belokon et al., (Y. N. Belokon, A. G. Bulychev, S. V. Vitt, Y. T. Struchkov, A. S. Batsanov, T. V. Timofeeva, V. A. Tsyryapkin, M. G. Ryzhov and L. A. Lysova, *J. Am. Chem. Soc.*, 1985, 107, 4252-4259) served as the chiral auxiliary reagent. The S-benzylprolyl aminobenzophenone (BPB) was used as the chiral ligand to produce the chiral auxiliary agent in accordance with a simple procedure using $Ni(NO_3)_2 \cdot 6H_2O$.

The stereoselective homologation of intermediate 6 was conducted via direct alkyl-halide alkylation with intermediate 5 at ambient temperature in very good yield. The resultant intermediate 7 then disassembled under acidic and microwave condition to yield the tryptophan derivatives as the HCl salt. Using this robust reaction sequence, L-tryptophan analogues can be obtained with >90% yield and >95% enantiomeric ratio. An optional N-Fmoc protection of the tryptophan analogues 1 provides intermediates for the Fmoc solid phase synthesis of the compounds of the invention (Scheme 4).

Scheme 4: Synthesis of L-tryptophan analogues 1

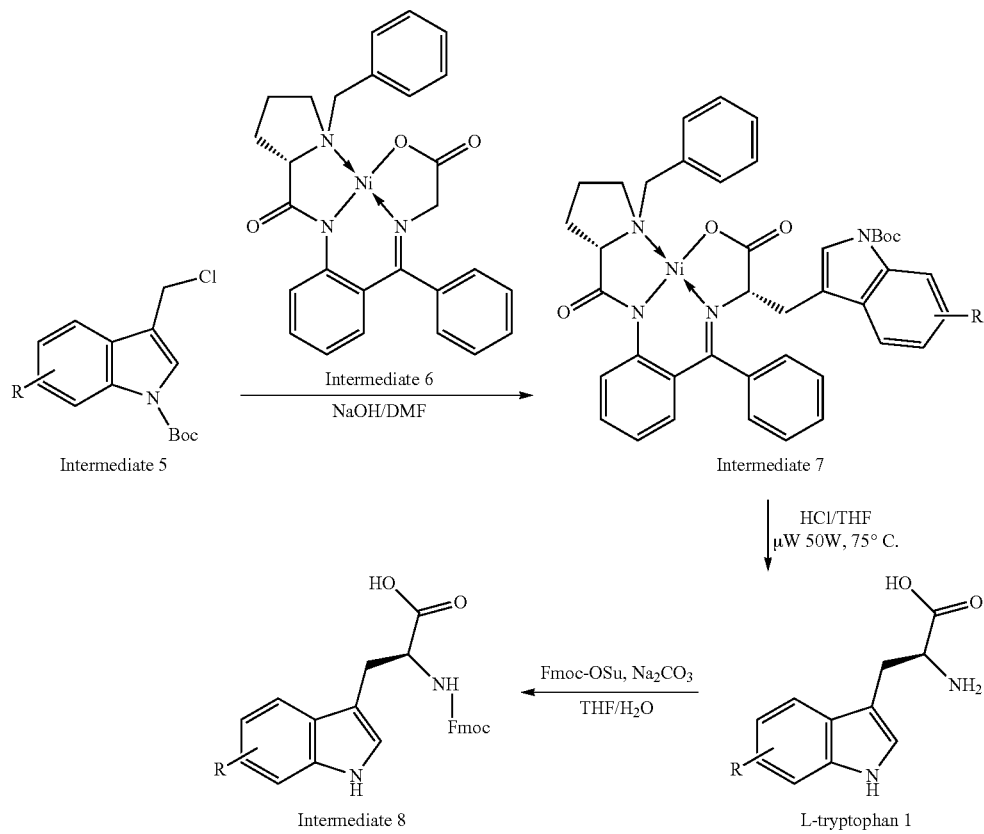

Materials and Methods $^{1}$H-Nuclear magnetic resonance (NMR) spectra were acquired at room temperature using a Bruker 400 Ultrashield operating at 400 MHz. Chemical shifts given in δ values are relative to an internal residual protic solvent CDCl$_{3}$($δ_{H}$=7.26 parts per million (ppm)), DMSO-d$_{6}$ ($δ_{H}$=2.50 ppm), deuterium oxide (D$_{2}$O) and (CD$_{3}$)$_{2}$CO ($δ_{H}$=2.05 ppm). The multiplicity of a signal is designated by one of the following abbreviations. s, singlet; d, doublet; t, triplet; q, quartet; br, broad; m, multiplet; dd, doublet of doublets, etc. All coupling constants (J) are given in Hertz. $^{13}$C-NMR spectra were recorded at room temperature using the same spectrometer operating at 100 MHz. Chemical shifts given in δ values are relative to an internal reference of CDCl$_{3}$ ($δ_{H}$=77.16 ppm) and (CD$_{3}$)$_{2}$CO ($δ_{H}$=29.84 ppm). $^{1}$H assignments were achieved using correlation spectroscopy (COSY). Mass spectra were recorded using Waters 2759 spectrometer by positive electrospray ionization. Lyophilisation from water was carried out on an Edwards Modulyo FD freeze drier. Melting points (m.p.) were determined in a glass capillary using a Gallenkamp 3A 3790 melting point apparatus and are uncorrected. Optical rotation was measured on a Bellingham & Stanley Ltd. ADP 220 polarimeter. [α]$_{D}$ values are reported in 10$^{-1}$ deg. cm$^{-2}$. g$^{-1}$, concentration (c) is in grams per 100 mL.

Analytical reverse-phase high performance liquid chromatography (RP-HPLC) was performed using a Waters 510 twin pump using an Onyx Monolithic C$_{18}$ column (100×4.6 mm) at a flow rate of 3.0 mL min$^{-1}$. Standard solvents used for both analytical and preparative HPLC were: 100% H$_{2}$O, 0.06% TFA (Solvent A) and 90% MeCN, 10% H$_{2}$O and 0.06% TFA (Solvent B). Eluent detection was monitored by ultraviolet (UV) absorbance using a Waters 486 Tunable Absorbance Detector at 214 nm. The linear elution gradient was either:

Method 1: 10 to 60% B over 12 min at 3.0 mL min$^{-1}$;
Method 2: 1 to 30% B over 8 min at 3.0 mL min$^{-1}$;
Method 3: 35 to 90% B over 12 min at 3.0 mL min$^{-1}$.

Purification by preparative RP-HPLC was performed using a Waters 2525 twins pumps and a Waters 2487 Detector using Onyx Monolithic-C$_{18}$ semi-preparative column (10×100 mm) at 9 mL min$^{-1}$ or Hichrom Kromasil-100C$_{8}$ semi-preparative column (10×100 mm) at 4 mL min$^{-1}$ or Phenomenex Luna C$_{18}$ (5 μm) column (21.2×250 mm) at 20 mL min$^{-1}$. The detector was set-up to record the absorbance of the effluent at 214 nm. Standard solvents used for both analytical and preparative HPLC were: 100% H$_{2}$O, 0.06% TFA (Solvent A) and 90% MeCN, 10% H$_{2}$O and 0.06% TFA (Solvent B). Purification by column chromatography was carried out using silica gel Acros Organic Kieselgel (0.035-0.070 mm). Ion exchange purification was carried out using Dowex (2×100 mm) resin in 2 cm column. H$_{2}$O and 0.005-0.5% NH$_{3}$ in H$_{2}$O were used as eluents.

Solid phase peptide synthesis was carried out in an Omnifit continuous flow glass column (150×10 mm) and all wash and deprotection steps were carried out using a Novasyn GEM manual peptide synthesiser. UV absorbance was measured at 344 nm using a LKB Biochrom Ultrospec II spectrometer and recorded using a LKB Bromma 2210 recorder.

Starting materials were either commercially available, from sources such as Sigma-Aldrich, or synthesised from commercially available materials using methods and techniques well-known to the skilled person.

Preparation of Intermediate 2

General Procedure

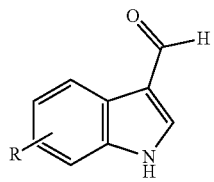

Phosphoryl chloride (1.5 equiv.) was added dropwise to anhydrous DMF (10 mL) at 0° C. and left to stir for 10 min. To this, a solution of 4-fluoroindole (1 equiv.) in anhydrous DMF (5 mL) was added dropwise and the resultant mixture was heated to 45° C. and left to stir for 2 h. The reaction mixture was cooled to room temperature and pH was adjusted to 9-10 with 1 M NaOH. The resultant suspension was then heated to 60° C. and left to cool to room temperature. Deionised water was added to the cooled mixture and the resultant precipitate was filtered and washed with excess deionised water. The precipitate was air dried overnight to yield the title compound.

4-Fluoro-1H-indole-3-carbaldehyde (Intermediate 2a)

Synthesis was carried out using the general procedure, using phosphoryl chloride (2.1 mL, 22.2 mmol), 4-fluoroindole (2.0 g, 14.8 mmol) and DMF (10 mL) to yield the title compound as beige solid (1.76 g, 77% yield); m.p. 170-172° C. (Lit. m.p. 182-187° C.); $R_f$=0.2 (hexane/EtOAc 2:1); $^1$H-NMR (400 MHz, (CD$_3$)$_2$CO): δ=7.02 (td, J=9.5, 3 Hz, 1H, H-6), 7.29 (td, J=8, 5 Hz, H-7), 7.45 (d, J=8 Hz, 1H, H-5), 8.23 (s, 1H, H-2), 10.21 (d, J=2 Hz, 1H, CHO) ppm; $^{13}$C-NMR (100 MHz, (CD$_3$)$_2$CO): δ=108.8 (d, J=20 Hz), 115.5 (d, J=20 Hz), 119.4 (d, J=5 Hz), 125.6 (d, J=8 Hz), 135.1, 141.5, 157.2, 159.6, 185.2 ppm; MS: m/z (+ESI) calcd. for C$_9$H$_7$FNO$^+$164.0506, found 163.7540 [MH$^+$].

4-Chloro-1H-indole-3-carbaldehyde (Intermediate 2b)

Synthesis was carried out using the general procedure described, using phosphoryl chloride (1.4 mL, 15.3 mmol), 4-chloroindole (2.0 g, 10.2 mmol) and DMF (10 mL) to yield the title compound as brown solid (1.97 g, 90% yield); m.p. 146-148° C. (Lit. m.p. 147-148° C.); $R_f$=0.2 (hexane/EtOAc 2:1); $^1$H-NMR (400 MHz, CDCl$_3$): δ=7.22 (t, J=8 Hz, 1H, H-6), 7.32 (dd, J=8, 1 Hz, H-7), 7.40 (dd, J=8, 1 Hz, 1H, H-5), 8.01 (d, J=2 Hz, H-2), 9.21 (br, 1H, NH), 10.75 (s, 1H, CHO) ppm; $^{13}$C-NMR (100 MHz, CDCl$_3$): δ=110.9, 119.7, 119.9, 123.6, 123.8, 124.2, 126.5, 130.9, 137.7, 162.3, 187.1 ppm; MS: m/z (+ESI) calcd. for C$_9$H$_7$ClNO$^+$ 180.6105, found 179.9873 [MH$^+$].

4-Bromo-1H-indole-3-carbaldehyde (Intermediate 2c)

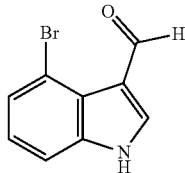 [SMILES: O=Cc1c[nH]c2cccc(Br)c12]

Synthesis was carried out using the general procedure, using phosphoryl chloride (1.4 mL, 15.3 mmol), 4-bromoindole (2.0 g, 10.2 mmol) and DMF (10 mL) to yield the title compound as white solid (1.97 g, 90% yield); m.p. 160-161° C. (Lit m.p. 168-170° C.); $R_f$=0.2 (hexane/EtOAc 2:1); $^1$H-NMR (400 MHz, CDCl$_3$): δ=7.15 (t, J=8 Hz, 1H, H-6), 7.45 (dd, J=8, 1 Hz, H-5), 7.50 (dd, J=8, 1 Hz, 1H, H-7), 8.11 (d, J=3 Hz, 1H, H-2), 9.17 (br, 1H, NH), 10.93 (s, 1H, CHO) ppm; $^{13}$C-NMR (100 MHz, CDCl$_3$): δ=111.7, 114.1, 119.9, 124.6, 125.7, 127.3, 131.5, 137.9, 187.1 ppm; MS: m/z (+ESI) calcd. for C$_9$H$_7$BrNO$^+$223.9706, found 223.9734 [MH$^+$].

4-(Trifluoromethyl)-1H-indole-3-carbaldehyde (Intermediate 2d)

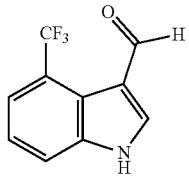 [SMILES: O=Cc1c[nH]c2cccc(C(F)(F)F)c12]

Synthesis was carried out using the general procedure, using phosphoryl chloride (0.76 mL, 8.1 mmol), 4-trifluoromethylindole (1.0 g, 5.4 mmol) and DMF (7 mL) to yield the title compound as brown solid (1.0 g, 87% yield); m.p. 178-180° C.; $R_f$=0.5 (hexane/EtOAc 1:1); $^1$H-NMR (400 MHz, acetone-d$_6$): δ=7.43 (dt, J=8, 1 Hz, H-7), 7.67 (d, J=8 Hz, 1H, H-6), 7.91 (d, J=8 Hz, 1H, H-5), 8.34 (s, 1H, H-2), 10.27, (d, J=1 Hz, 1H, CHO), 11.7 (br, 1H, NH) ppm; $^{13}$C-NMR (100 MHz, acetone-d$_6$): δ=118.3, 118.5, 120.7 (q, J=6 Hz), 121.3, 123.1, 124.8, 127.5, 134.9, 139.3, 185.8 (q, J=5 Hz) ppm; MS: m/z (+ESI) calcd. for C$_{10}$H$_7$F$_3$NO$^+$ 214.0474, found 213.8489 [MH$^+$].

4,5-Dichloro-1H-indole-3-carbaldehyde
(Intermediate 2e)

Synthesis was carried out using the general procedure, using phosphoryl chloride (0.62 mL, 4.1 mmol), 4,5-dichloroindole (0.5 g, 2.7 mmol) and DMF (7 mL) to yield the title compound as brown solid (1.0 g, 87% yield); m.p. 224-226° C. (Lit. m.p. 244-245° C.); $R_f$=0.5 (hexane/EtOAc 1:1); $^1$H-NMR (400 MHz, CDCl$_3$): δ=7.36 (d, J=9 Hz, H-6), 7.57 (d, J=8 Hz, H-7), 8.10 (s, 1H, CH-2), 8.35 (br, 1H, NH), 10.76 (s, 1H, CHO) ppm; $^{13}$C-NMR (100 MHz, CDCl$_3$): δ=92.4, 96.7, 100.3, 111.7, 124.4, 125.0, 162.7, 183.8.7 ppm; MS: m/z (+ESI) calcd. for C$_9$H$_6$Cl$_2$NO$^+$213.9821, found 213.7788 [MH$^+$].

Preparation of Intermediate 3

General Procedure

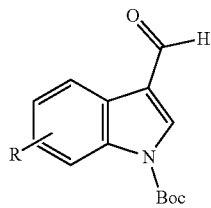

Boc$_2$O (1.5 equiv.) followed by DMAP (0.3 equiv.) was added to a 46 mM solution of intermediate 2 (1 equiv.) in anhydrous THF. The reaction mixture was stirred at room temperature under nitrogen atmosphere. When no starting material was detected by TLC, H$_2$O was added to the reaction mixture and the volatiles were evaporated under vacuo. The residual water phase was extracted with EtOAc. The pooled organic phase was washed with brine, dried over Na$_2$SO$_4$, filtered and concentrated under vacuo to yield the intermediate 3.

tert-Butyl 4-fluoro-3-formyl-1H-indole-1-carboxylate
(Intermediate 3a)

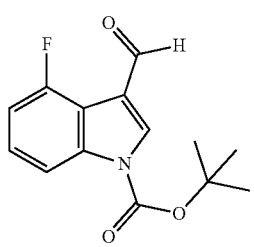 [SMILES: CC(C)(C)OC(=O)n1cc(C=O)c2c(F)cccc21]

Synthesis was carried out using the general procedure, using a 46 mM solution of intermediate 2a (1.76 g, 10.8 mmol), Boc$_2$O (3.5 g, 16.2 mmol) and DMAP (0.4 g 3.2 mmol) in anhydrous THF to yield the title compound as white powder (2.77 g, 99% yield); m.p. 98-100° C.; $R_f$=0.5 (hexane/EtOAc 2:1); $^1$H-NMR (400 MHz, CDCl$_3$): δ=1.69 (s, 9H, Boc), 7.07 (m, 1 Hz, 1H, H-7), 7.34 (dt, J=8, 5 Hz, 1H, H-6), 8.02 (d, J=8 Hz, 1H, H-5), 8.28 (s, 1H, H-2), 10.30 (d, J=2 Hz, 1H, CHO) ppm; $^{13}$C-NMR (100 MHz, CDCl$_3$): δ=28.4, 86.4, 110.3 (d, J=20 Hz), 112.1 (d, J=3.6 Hz), 116.0 (d, J=23 Hz), 120.1 (d, J=5.6 Hz), 126.7 (d, J=7.3 Hz), 132.1, 138.3 (d, J=8.6 Hz), 148.9, 156.8 (d, J=250 Hz), 186.2 (d, J=3.6 Hz) ppm.

tert-Butyl 4-chloro-3-formyl-1H-indole-1-carboxylate
(Intermediate 3b)

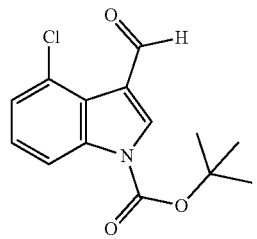 [SMILES: CC(C)(C)OC(=O)n1cc(C=O)c2c(Cl)cccc21]

Synthesis was carried out using the general procedure, using a 46 mM solution of intermediate 2b (2.17 g, 12.1 mmol), Boc$_2$O (4.0 g, 18.12 mmol) and DMAP (0.44 g 3.6 mmol) in anhydrous THF to yield the title compound as white powder (3.2 g, 94% yield); m.p. 110-112° C.; $R_f$=0.5 (hexane/EtOAc 2:1); $^1$H-NMR (400 MHz, CDCl$_3$): δ=1.68 (s, 9H, Boc), 7.31 (t, J=8, 1 Hz, 1H, H-5), 7.37 (dd, J=8, 1 Hz, 1H, H-6), 8.21 (dd, J=8, 1 Hz, 1H, H-7), 8.37 (s, 1H, H-2), 10.79 (s, 1H, CHO) ppm; $^{13}$C-NMR (100 MHz, CDCl$_3$): δ=28.1, 86.3, 114.5, 121.1, 125.2, 125.9, 126.2, 131.8, 137.3, 148.5, 187.2 ppm; MS: m/z (+ESI) calcd. for C$_{14}$H$_{15}$ClNO$_3$$^+$280.0735, found 280.0042 [MH$^+$].

tert-Butyl 4-bromo-3-formyl-1H-indole-1-carboxylate
(Intermediate 3c)

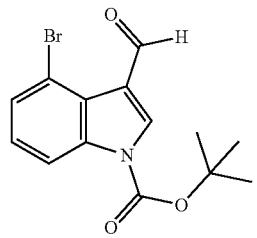 [SMILES: CC(C)(C)OC(=O)n1cc(C=O)c2c(Br)cccc21]

Synthesis was carried out using the general procedure, using a 46 mM solution of intermediate 2c (1.8 g, 8 mmol), Boc$_2$O (2.6 g, 12.1 mmol) and DMAP (0.3 g 2.4 mmol) in anhydrous THF to yield the title compound as white powder (2.4 g, 95% yield); m.p. 105-107° C. (Lit. m.p. 117-119° C.); $R_f$=0.5 (hexane/EtOAc 2:1); $^1$H-NMR (400 MHz, CDCl$_3$): δ=1.68 (s, 9H, Boc), 7.24 (t, J=8 Hz, 1H, H-6), 7.55 (dd, J=8, 1 Hz, 1H, H-6), 8.27 (dd, J=8, 1 Hz, 1H, H-5), 8.38 (s, 1H, H-2), 10.97 (s, 1H, CHO) ppm; $^{13}$C-NMR (100 MHz, CDCl$_3$): δ=28.2, 86.3, 106.7, 113.6, 115.0, 121.2, 126.1, 127.0, 128.6, 132.1, 137.4, 148.5, 149.8, 187.1 ppm; MS: m/z (+ESI) calcd. for C$_{14}$H$_{15}$BrNO$_3$$^+$325.1572, found 325.1815 [MH$^+$].

tert-Butyl 3-formyl-4-(trifluoromethyl)-1H-indole-1-carboxylate (Intermediate 3d)

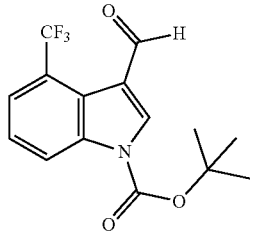 [SMILES: CC(C)(C)OC(=O)n1cc(C=O)c2c(C(F)(F)F)cccc21]

Synthesis was carried out using the general procedure, using a 46 mM solution of intermediate 2d (1.15 g, 5.4 mmol), Boc$_2$O (1.77 g, 8.1 mmol) and DMAP (0.2 g, 1.62 mmol) in anhydrous THF to yield the title compound as white powder (1.63 g, 96% yield); m.p. 70-72° C.; R$_f$=0.5 (hexane/EtOAc 2:1); $^1$H-NMR (400 MHz, CDCl$_3$): δ=1.69 (s, 9H, Boc), 7.47 (t, J=8, Hz, 1H, H-6), 7.71 (d, J=8 Hz, H-7), 8.46, (s, 1H, CH-2), 8.55 (d, J=9 Hz, 1H, H-5), 10.33 (s, 1H, CHO) ppm; $^{13}$C-NMR (100 MHz, CDCl$_3$): δ=28.1, 86.5, 119.9 (d, J=12 Hz), 121.7, 121.8 (d, J=6.5 Hz), 121.9 (d, J=6 Hz), 122.0 (d, J=4 Hz), 122.9 (d, J=2 Hz), 123.3, 124.7, 126.0, 137.2, 148.4, 187.4, 187.5 ppm.

tert-Butyl 4,5-dichloro-3-formyl-1H-indole-1-carboxylate (Intermediate 3e)

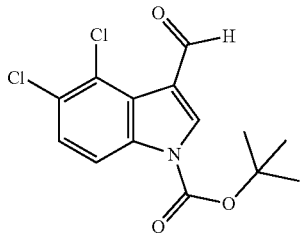 [SMILES: CC(C)(C)OC(=O)n1cc(C=O)c2c(Cl)c(Cl)ccc21]

Synthesis was carried out using the general procedure, using a 46 mM solution of intermediate 2e (0.54 g, 2.46 mmol), Boc$_2$O (0.81 g, 3.69 mmol) and DMAP (0.09 g, 0.74 mmol) in anhydrous THF to yield the title compound as white powder (0.75 g, 97% yield); m.p. 142-144° C.; R$_f$=0.5 (hexane/EtOAc 2:1); $^1$H-NMR (400 MHz, CDCl$_3$): δ=1.68 (s, 9H, Boc), 7.46 (d, J=9 Hz, 1H, H-7), 8.16 (d, J=9 Hz, H-6), 8.37 (s, 1H, H-2), 10.78 (s, 1H, CHO) ppm; $^{13}$C-NMR (100 MHz, CDCl$_3$): δ=28.1, 86.7, 115.3, 121.0, 124.4, 126.6, 126.9, 129.2, 132.6, 135.4, 154.4, 186.9 ppm; MS: m/z (+ESI) calcd. for C$_{14}$H$_{14}$C$_{12}$NO$_3$$^+$314.0345, found 313.5853 [MH$^+$].

Preparation of Intermediate 4

General Procedure

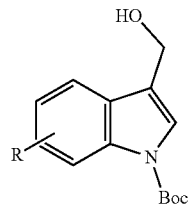

NaBH$_4$ (2 equiv.) was added to a stirring suspension of intermediate 3 (1 equiv.) in EtOH and the resultant mixture was stirred overnight. The volatile was evaporated under vacuo and the resultant oil was shaken with 1 M NaOH. The alkaline solution was extracted with Et$_2$O. The organic layers were combined, dried over Na$_2$SO$_4$, filtered and concentrated under vacuo. The crude was purified using column chromatography to yield the intermediate 4.

tert-Butyl 4-fluoro-3-(hydroxymethyl)-1H-indole-1-carboxylate (Intermediate 4a)

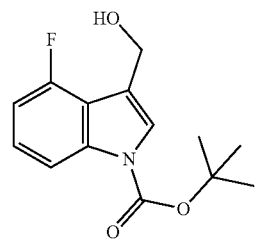 [SMILES: CC(C)(C)OC(=O)n1cc(CO)c2c(F)cccc21]

Synthesis was carried out using the general procedure, using NaBH$_4$ (0.72 g, 19 mmol) and intermediate 3a (2.5 g, 9.5 mmol) to yield the title compound as off-white powder (1.6 g, 63% yield); m.p. 67-68° C.; R$_f$=0.4 (hexane/EtOAc 2:1); 1H-NMR (400 MHz, CDCl$_3$): δ=1.66 (s, 9H, Boc), 2.01 (br, 1H, OH), 4.87 (s, 2H, CH2), 6.92 (td, J=9, 1 Hz, 1H, H-5), 7.24 (td, J=8, 5 Hz, H-6), 7.53 (s, 1H, H-7), 7.95 (d, J=8 Hz, 1H, H-2) ppm; $^{13}$C-NMR (100 MHz, CDCl$_3$): δ=28.5, 58.1 (d, J=2), 86.6, 108.6 (d, J=20 Hz), 111.9 (d, J=3.6 Hz), 117.8 (d, J=21 Hz), 119.2 (d, J=3.5 Hz), 124.1, 125.7 (d, J=8 Hz), 138.5 (d, J=10 Hz), 149.7, 156.6 (d, J=250 Hz) ppm.

tert-Butyl 4-chloro-3-(hydroxymethyl)-1H-indole-1-carboxylate (Intermediate 4b)

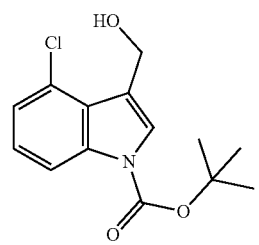 [SMILES: CC(C)(C)OC(=O)n1cc(CO)c2c(Cl)cccc21]

Synthesis was carried out using the general procedure, using $NaBH_4$ (0.87 g, 22.9 mmol) and intermediate 3b (3.2 g, 11.44 mmol) to yield the title compound as off-white powder (1.38 g, 43% yield); m.p. 98-112° C.; $R_f$=0.4 (hexane/EtOAc 2:1); $^1$H-NMR (400 MHz, $CDCl_3$): δ=1.66 (s, 9H, Boc), 2.19 (br, 1H, OH), 4.96 (s, 2H, $CH_2$), 7.21 (m, 1H, H-6), 7.22 (m, 1H, H-5), 7.61 (s, 1H, H-5), 8.11 (dd, J=7, 3 Hz, 1H, H-2) ppm; $^{13}$C-NMR (100 MHz, $CDCl_3$): δ=28.3, 57.7, 84.5, 114.3, 120.4, 123.6, 125.4, 125.6, 125.7, 126.6, 137.5, 149.3 ppm; MS: m/z (+ESI) calcd. for $C_{14}H_{16}ClNNaO_3^+$ 304.7252, found 304.9205 [MNa$^+$].

tert-Butyl 4-bromo-3-(hydroxymethyl)-1H-indole-1-carboxylate (Intermediate 4c)

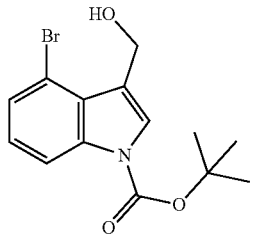

Synthesis was carried out using the general procedure, using $NaBH_4$ (0.56 g, 14.8 mmol) and intermediate 3c (2.4 g, 7.4 mmol) to yield the title compound as off-white solid (1.4 g, 60% yield); m.p. 97-99° C.; $R_f$=0.4 (hexane/EtOAc 2:1); $^1$H-NMR (400 MHz, $CDCl_3$): δ=1.66 (s, 9H, Boc), 4.97 (s, 2H, CH2), 7.16 (t, J=8 Hz, 1H, H-7), 7.40 (dd, J=8, 1 Hz, H-6), 7.65 (s, 1H, H-2), 8.19 (d, J=9 Hz, 1H, H-5) ppm; $^{13}$C-NMR (100 MHz, $CDCl_3$): δ=28.3, 57.3, 84.5, 113.6, 114.8, 120.8, 125.6, 126.1, 127.0, 128.0, 137.5, 149.2 ppm; MS: m/z (+ESI) calcd. for $C_{14}H_{16}BrKNO_3^+$ 365.9925, found 365.9877 [MK$^+$].

tert-Butyl 3-(hydroxymethyl)-4-(trifluoromethyl)-1H-indole-1-carboxylate (Intermediate 4d)

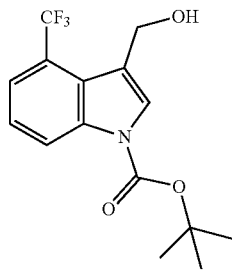 [SMILES: CC(C)(C)OC(=O)n1cc(CO)c2c(C(F)(F)F)cccc21]

Synthesis was carried out using the general procedure, using $NaBH_4$ (0.39 g, 10.41 mmol) and intermediate 3d (1.63 g, 5.2 mmol) to yield the title compound as off-white powder (0.529 g, 32% yield); m.p. 70-72° C.; $R_f$=0.4 (hexane/EtOAc 2:1); $^1$H-NMR (400 MHz, $CDCl_3$): δ=1.67 (s, 9H, Boc), 1.93 (br, 1H, OH), 4.92 (s, 2H, $CH_2$), 7.38 (t, J=8 Hz, 1H, H-6), 7.59 (d, J=8 Hz, H-7), 7.82 (s, 1H, H-2), 8.5 (d, J=8 Hz, 1H, H-5) ppm; $^{13}$C-NMR (100 MHz, $CDCl_3$): δ=28.3, 58.3 (d, J=7 Hz), 84.6, 119.4, 120.0, 120.7 (q, J=6 Hz), 121.3, 121.7, 123.3, 123.7, 126.0, 126.8, 137.4, 149.2 ppm.

tert-Butyl 4,5-dichloro-3-(hydroxymethyl)-1H-indole-1-carboxylate (Intermediate 4e)

Synthesis was carried out using the general procedure, using $NaBH_4$ (0.18 g, 4.76 mmol) and intermediate 3e (0.75 g, 2.38 mmol) to yield the title compound as off-white powder (0.57 g, 76% yield); m.p. 118-122° C.; $R_f$=0.4 (hexane/EtOAc 2:1); $^1$H-NMR (400 MHz, $CDCl_3$): δ=1.65 (s, 9H, Boc), 4.97 (d, J=1 Hz, 2H, $CH_2$), 7.35 (d, J=9 Hz, H-7), 7.63 (s, 1H, H-2), 8.0 (d, J=9 Hz, 1H, H-6) ppm; $^{13}$C-NMR (100 MHz, $CDCl_3$): δ=28.3, 57.6, 84.8, 114.9, 120.6, 123.8, 124.0, 126.1, 126.5, 127.2, 127.9, 135.6 ppm.

Preparation of Intermediates 5 and 7

General procedures

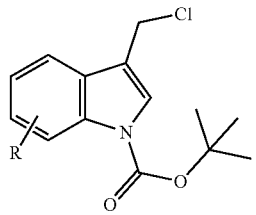

intermediate 5

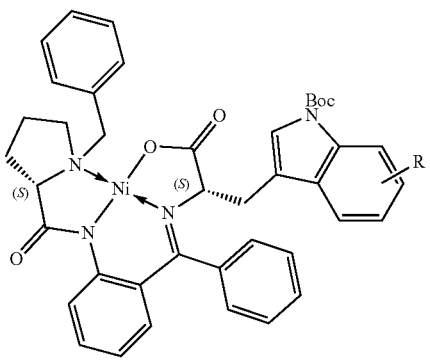

intermediate 7

To a solution of intermediate 4 (1 equiv.) in $CH_2Cl_2$ stirred at 0° C., DBU (2 equiv.) followed by methane sulfonyl chloride (1.5 eqiuv.) were added. The reaction mixture was brought to room temperature and refluxed for 2 h before quenching with saturated $NaHCO_3$. The aqueous layer was separated and back extracted with $CH_2Cl_2$. The organic layers were combined, dried over $Na_2SO_4$, filtered and concentrated under vacuo to afford intermediate 5 as unstable crude mixture, which was taken to the next step without purification.

Freshly ground NaOH (2 equiv.) was added to a stirred solution of intermediate 6 (1 equiv.) in anhydrous DMF at 40° C. To this, a solution of the crude intermediate 5 dissolved in DMF was added dropwise over 15 min and the resultant reaction mixture was left to stir for a further 40 min. Upon completion, water was added to the stirring mixture and the resultant red precipitate was filtered over a sintered funnel and washed with excess water. The red precipitate was dissolved in CH$_2$Cl$_2$ and washed with water followed by aqueous LiCl. The organic layer was dried over Na$_2$SO$_4$, filtered and concentrated under vacuo. The crude was purified using column chromatography (EtOAc/hexane/acetone 6:2:2) to yield the intermediate 7 as dark red solid.

Nickel(II)-(S)-BPB/(S)-2-Amino-3-(1-(tert-butoxycarbonyl)-4-fluoro-1H-indol-3-yl)Propanoic Acid Schiff Base Complex (Intermediate 7a)

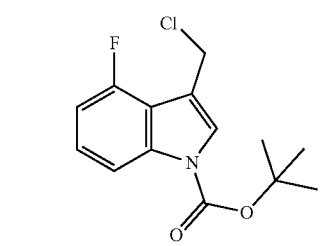

intermediate 5a

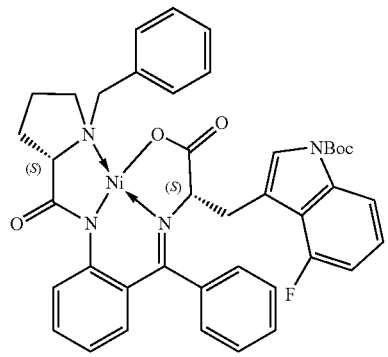

intermediate 7a

Synthesis was carried out using the general procedure, using intermediate 4a (0.5 g, 1.9 mmol), DBU (0.54 mL, 3.8 mmol) and methane sulfonyl chloride (0.22 mL, 2.85 mmol) to yield the unstable crude intermediate 5a which was taken to the next step without purification.

The crude mixture from above reaction was subjected to the synthetic procedure described under general procedure using DMF (20 mL), intermediate 6 (0.58 g, 1.17 mmol) and NaOH (0.09 g, 2.33 mmol) to yield the title compound as dark red solid (0.66 g, 66% yield); m.p. 136-138° C.; R$_f$=0.5 (EtOAc/hexane/acetone 6:2:2); [α]$_D^{24}$=+1307.7° (c=0.13, MeOH); $^1$H-NMR (400 MHz, CDCl$_3$): δ=1.48 (m, 1H, pro-CH), 1.63 (s, 2H, Bn-CH$_2$), 1.64 (s, 9H, Boc), 1.87 (dt, J=10, 6 Hz, 1H, pro-CH), 2.07 (m, 1H, pro-CH), 2.20 (m, 1H, pro-CH), 3.01 (m, 1H, pro-H), 3.13 (dd, J=10, 5 Hz, 1H, trp-CH$_A$CH$_B$), 3.16 (m, 1H, pro-CH), 3.24 (dd, J=15, 5 Hz, 1H, trp-CH$_A$CH$_B$), 4.19 (d, J=12.5 Hz, 1H, pro-α-H), 4.29 (t, J=5 Hz, 1H, trp-α-H), 6.67 (m, 2H, Ar Hs), 6.76 (dd, J=12, 8 Hz, 1H, Ar H), 7.07 (m, 1H, Ar H), 7.14 (m, 2H, Ar Hs), 7.23 (m, 1H, Ar H), 7.29 (m, 2H, Ar Hs), 7.40 (m, 2H, Ar Hs), 7.52 (m, 2H, Ar Hs), 7.95 (m, 2H, Ar Hs), 8.09 (d, J=8.5 Hz, 1H, Ar H), 8.29 (d, J=8.5 Hz, 1H, Ar H) ppm; $^{13}$C-NMR (100 MHz, CDCl$_3$): δ=15.4, 22.9, 27.8, 28.2, 30.3, 30.8, 57.0, 63.3, 65.9, 70.4, 72.2, 84.4, 108.7, 108.9, 110.8, 111.75 (d, J=4.5 Hz), 112.7 (d, J=2 Hz), 119.5, 119.7, 120.5, 123.2, 125.7 (d, J=8 Hz), 126.1, 126.4, 127.4, 127.8, 128.0 (d, J=4.5 Hz), 128.9, 129.0 (d, J=7.5 Hz), 129.7, 131.6, 132.4, 133.3, 133.7, 134.3, 143.0, 149.4, 155.6, 162.2, 172.1, 179.4 (d, J=128 Hz) ppm; MS: m/z (+ESI) calcd. for C$_{41}$H$_{41}$N$_4$NiO$_4^+$ 727.2425, found 727.2407 [MH$^+$ (−F)]; RP-HPLC Method 3, t$_R$ 7.34 min, de 92%.

Nickel(II)-(S)-BPB/(S)-2-Amino-3-(1-(tert-butoxycarbonyl)-4-chloro-1H-indol-3-yl)Propanoic Acid Schiff Base Complex (Intermediate 7b)

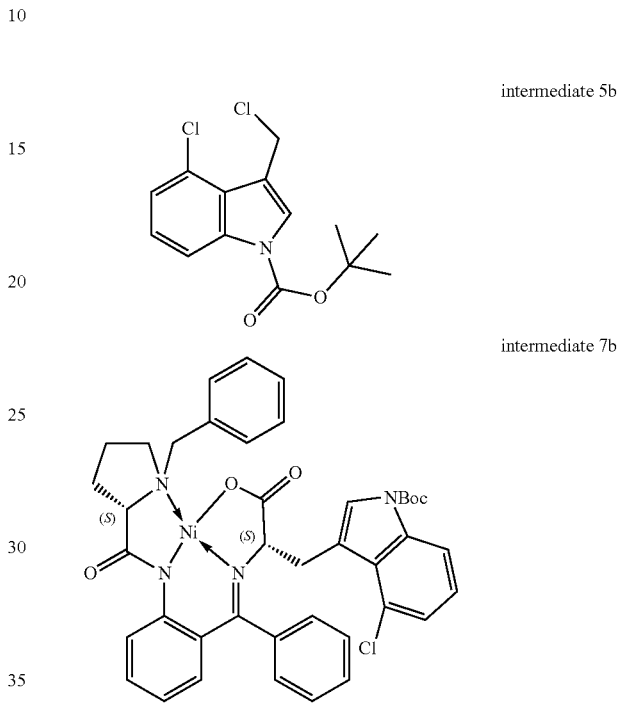

intermediate 5b intermediate 7b

Synthesis was carried out using the general procedure, using intermediate 4b (0.7 g, 2.49 mmol), DBU (0.7 mL, 5.0 mmol) and methane sulfonyl chloride (0.3 mL, 3.75 mmol) to yield the unstable crude intermediate 5b which was taken to the next step without purification.

The crude mixture from above reaction was subjected to the synthetic procedure described under general procedure using DMF (20 mL), intermediate 6 (1.24 g, 2.5 mmol) and NaOH (0.2 g, 5 mmol) to yield the title compound as dark red solid (1.0 g, 55% yield); m.p. 110-112° C.; R$_f$=0.5 (EtOAc/hexane/acetone, 6:2:2); [α]$_D^{24}$=+1265.5 (c=0.11, MeOH);

$^1$H-NMR (400 MHz, CDCl$_3$): δ=1.57 (s, 9H, Boc), 1.74 (s, 2H, Bn-CH$_2$), 2.05 (m, 2H, pro-CH$_2$), 2.46 (m, 2H, pro-CH$_2$), 3.36 (m, 2H, pro-CH$_2$), 3.71 (dd, J=14, 8 Hz, 1H, trp-CH$_A$H$_B$), 4.01 (dd, J=14, 6 Hz, 1H, trp-CH$_A$H$_B$), 4.35 (m, 1H, trp α-H), 4.38 (m, 1H, pro α-H), 6.35 (d, J=8 Hz, Ar H), 6.56 (dd, J=8, 2 Hz, 1H, Ar H), 6.63 (m, 1H, Ar H), 7.01 (t, J=8 Hz, 1H, Ar H), 7.05 (dd, J=7, 1 Hz, 1H, Ar H), 7.14 (m, 3H, Ar Hs), 7.24 (m, 1H, Ar H), 7.28-7.37 (m, 4H, Ar Hs), 7.45 (dt, J=8, 1 Hz, 1H, Ar H), 8.05 (m, 2H, Ar Hs), 8.10 (d, J=8 Hz, 1H, Ar H), 8.21 (dd, J=8, 1 Hz, 1H, Ar H) ppm; $^{13}$C-NMR (100 MHz, CDCl$_3$): δ=15.4, 24.0, 28.2, 31.0, 33.1, 57.3, 63.2, 66.0, 70.6, 72.2, 84.4, 114.0, 114.8, 120.7, 123.5, 124.0, 125.1, 126.5, 126.8, 127.2, 127.7, 127.8, 128.5, 128.8, 129.0, 129.6, 131.7, 132.4, 133.4, 133.6, 133.7, 137.1, 142.8, 149.0, 170.9, 172.5, 178.4, 180.3 ppm; MS: m/z (+ESI) calcd. for C$_{41}$H$_{40}$ClN$_4$NiO$_5^+$ 761.2035, found 761.1912 [MH$^+$]; RP-HPLC Method 3, t$_R$ 8.30 min, de 82%.

41
Nickel(II)-(S)-BPB/(S)-2-Amino-3-(1-(tert-butoxy-carbonyl)-4-bromo-1H-indol-3-yl)Propanoic Acid Schiff Base Complex (Intermediate 7c)

42
Nickel(II)-(S)-BPB/(S)-2-Amino-3-(1-(tert-butoxy-carbonyl)-4-trifluoro-1H-indol-3-yl)Propanoic Acid Schiff Base Complex (Intermediate 7d)

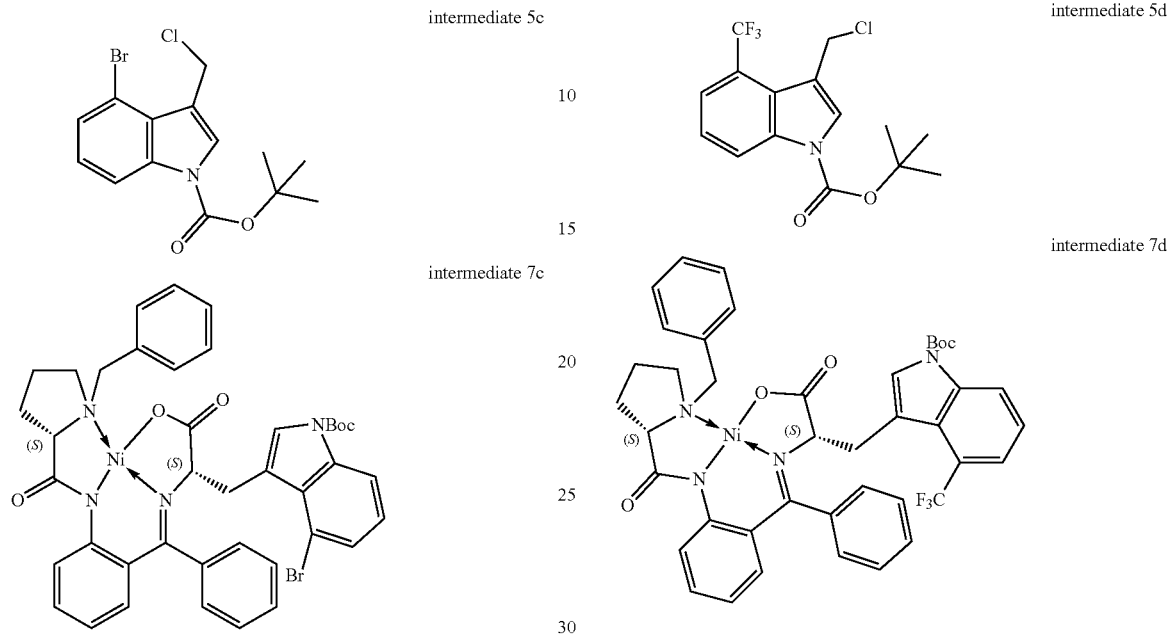

Synthesis was carried out using the general procedure, using intermediate 4c (1.0 g, 3.1 mmol), DBU (0.87 mL, 6.15 mmol) and methane sulfonyl chloride (0.36 mL, 4.65 mmol) to yield the unstable crude intermediate 5c which was taken to the next step without purification.

The crude mixture from above reaction was subjected to the synthetic procedure described under general procedure using DMF (25 mL), intermediate 6 (1.23 g, 2.5 mmol) and NaOH (0.2 g, 5 mmol) to yield the title compound as dark red solid (1.3 g, 64% yield); m.p. 98-100° C.; $R_f$=0.5 (EtOAc/hexane/acetone, 6:2:2); $[\alpha]_D^{24}$=+1109.3 (c=0.18, MeOH);

$^1$H-NMR (400 MHz, CDCl$_3$): δ=1.76 (s, 2H, Bn-CH$_2$), 2.16 (s, 9H, Boc), 2.58 (m, 2H, pro-CH$_2$), 3.44 (m, 2H, pro-CH$_2$), 3.52 (m, 2H, pro-CH$_2$), 3.84 (dd, J=15, 8 Hz, 1H, CH$_A$H$_B$), 4.11 (dd, J=14, 7 Hz, 1H, CH$_A$H$_B$), 4.40 (m, 1H, trp α-H), 4.44 (m, 1H, pro α-H), 6.13 (d, J=7 Hz, Ar H), 6.53 (dd, J=8, 2 Hz, 1H, Ar H), 6.61 (m, 1H, Ar H), 7.86 (t, J=7 Hz, 1H, Ar H), 7.05-7.16 (m, 3H, Ar Hs), 7.20-7.24 (m, 2H, Ar Hs), 7.36 (s, 1H, Ar H), 7.42 (dt, J=7, 1 Hz, 1H, Ar H), 8.06 (m, 2H, Ar Hs), 8.21 (d, J=8 Hz, 1H, Ar H), 8.21 (dd, J=8, 1 Hz, 1H, Ar H) ppm; $^{13}$C-NMR (100 MHz, CDCl$_3$): δ=24.1, 28.1, 31.0, 33.4, 57.3, 60.5, 63.2, 70.6, 72.0, 84.4, 114.3, 114.5, 115.4, 120.7, 123.5, 125.3, 126.4, 127.0, 127.4, 127.7, 127.8, 128.4, 128.5, 128.7, 129.0, 129.5, 131.6, 132.3, 133.4, 133.41, 133.7, 137.0, 142.7, 148.8, 170.7, 178.4, 180.3, 207.1 ppm; MS: m/z (+ESI) calcd. for $C_{41}H_{40}BrN_4NiO_5^+$805.1530, found 805.1481 [MH$^+$]; RP-HPLC Method 3, $t_R$ 8.13 min, de 96%.

Synthesis was carried out using the general procedure, using intermediate 4d (0.46 g, 1.47 mmol), DBU (0.41 mL, 2.94 mmol) and methane sulfonyl chloride (0.17 mL, 2.21 mmol) to yield the unstable crude intermediate 5d which was taken to the next step without purification.

The crude mixture from above reaction was subjected to the synthetic procedure described under general procedure using DMF (23 mL), intermediate 6 (0.59 g, 1.2 mmol) and NaOH (0.18 g, 4.6 mmol) to yield the title compound as dark red solid (0.40 g, 43% yield); m.p. 118-122° C.; $R_f$=0.5 (EtOAc/hexane/acetone, 6:2:2); $[\alpha]_D^{24}$=+1040.6 (c=0.1, MeOH);

$^1$H-NMR (400 MHz, CDCl$_3$): δ=1.54 (s, 9H, Boc), 1.60 (s, 2H, Bn-CH2), 2.10 (m, 1H, pro-CH), 2.27 (m, 1H, pro-CH), 2.59 (m, 1H, pro-CH), 2.79 (m, 1H, pro-CH), 3.50 (m, 2H, pro-CH$_2$), 3.54 (m, 1H, CH$_A$H$_B$), 3.67 (dd, J=15, 7 Hz, 1H, CH$_A$H$_B$), 3.84 (m, 1H, Trp α-H), 4.02 (m, 1H, pro α-H), 6.12 (d, J=8 Hz, 1H, Ar H), 6.55 (dd, J=8, 2 Hz, 1H, Ar H), 6.62 (m, 1H, Ar H), 6.85 (t, J=8 Hz, 1H, Ar H), 7.11 (m, 1H, Ar H), 7.18 (tt, J=8, 1 Hz, 1H, Ar H), 7.29-7.35 (m, 5H, Ar Hs), 7.44 (dt, J=9, 1 Hz, 2H, Ar Hs), 7.49 (d, J=8 Hz, 1H, Ar H), 8.09 (dd, J=8, 1 Hz, 2H, Ar Hs), 8.22 (dd, J=9, 1 Hz, 1H, Ar H), 8.46 (d, J=9 Hz, 1H, Ar H) ppm; $^{13}$C-NMR (100 MHz, CDCl$_3$): δ=24.2, 28.1, 31.1, 57.4, 63.1, 70.2, 70.7, 71.1, 84.6, 113.8, 119.2, 120.7, 123.4, 123.8, 126.2, 126.4, 127.6 (d, J=4 Hz), 127.7, 128.5, 128.7, 129.0 (d, J=3 Hz), 129.5, 130.2, 131.6, 131.7, 132.3, 133.5 (d, J=5 Hz), 133.6, 134.1, 134.16, 134.2, 136.9, 142.8, 144.4, 148.8, 170.8, 178.7, 179.4, 180.6 ppm; MS: m/z (+ESI) calcd. for $C_{42}H_{40}F_3N_4NiO_5^+$795.2299, found 794.9938 [MH$^+$]; RP-HPLC Method 3, $t_R$ 8.83 min, de 93%.

Nickel(II)-(S)-BPB/(S)-2-Amino-3-(1-(tert-butoxycarbonyl)-4,5-dichloro-1H-indol-3-yl)Propanoic Acid Schiff Base Complex (Intermediate 7e)

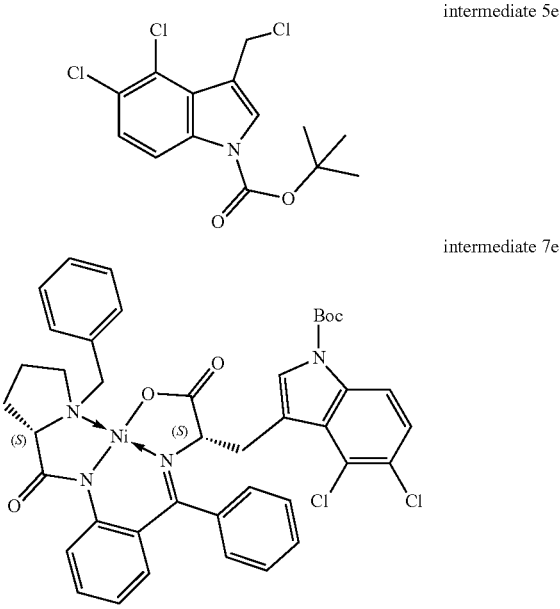

intermediate 5e intermediate 7e

Synthesis was carried out using the general procedure, using intermediate 4e (0.57 g, 1.8 mmol), DBU (0.51 mL, 3.62 mmol) and methane sulfonyl chloride (0.21 mL, 2.71 mmol) to yield the unstable crude intermediate 5e which was taken to the next step without purification.

The crude mixture from above reaction was subjected to the synthetic procedure described under general procedure using DMF (29 mL), intermediate 6 (0.72 g, 1.44 mmol) and NaOH (0.24 g, 5.8 mmol) to yield the title compound as dark red solid (0.63 g, 55% yield); m.p. 114-116° C.; $R_f$=0.5 (EtOAc/hexane/acetone, 6:2:2); $[\alpha]_D^{24}$=+970.4° (c=0.1, MeOH); $^1$H-NMR (400 MHz, CDCl$_3$): δ=1.56 (s, 9H, Boc), 1.66 (s, 2H, Bn-CH2), 2.09 (m, 1H, pro-CH), 2.21 (m, 1H, pro-CH), 2.57 (m, 1H, pro-CH), 2.70 (m, 1H, pro-CH), 3.47 (dd, J=11, 6 Hz, 2H, pro-CH$_2$), 3.54 (d, J=12 Hz, 1H, CH$_A$H$_B$), 3.61 (m, 1H, Trp α-H), 3.67 (m, 1H, CH$_A$H$_B$), 4.14 (dd, J=14, 7 Hz, 1H, pro α-H), 6.33 (d, J=8 Hz, 1H, Ar H), 6.57 (dd, J=8, 2 Hz, 1H, Ar H), 6.63 (m, 1H, Ar H), 7.02 (t, J=8 Hz, 1H, Ar H), 7.12 (m, 1H, Ar H), 7.17 (m, 1H, Ar H), 7.28-7.35 (m, 5H, Ar Hs), 7.38 (m, 2H, Ar Hs), 7.48 (dt, J=7, 1 Hz, 1H, Ar H), 8.07 (dd, J=8, 1 Hz, 2H, Ar Hs), 8.18 (dd, J=9, 1 Hz, 1H, Ar H) ppm; $^{13}$C-NMR (100 MHz, CDCl$_3$): δ=24.2, 25.7, 28.1, 31.0, 31.6, 33.7, 36.6, 57.3, 63.2, 68.1, 70.5, 71.8, 84.8, 114.5, 114.9, 120.8, 123.7, 124.5, 125.9, 126.5, 127.4, 127.5, 127.8, 127.82, 128.47, 128.5, 128.9, 129.0, 129.7, 131.7, 133.37, 133.4, 133.6, 135.2, 142.7, 148.7, 170.7, 178.1, 180.4 ppm; MS: m/z (+ESI) calcd. for $C_{41}H_{39}Cl_2N_4NiO_5^+$ 797.3789, found 796.9226 [MH$^+$]; RP-HPLC Method 3, $t_R$ 9.30 min, de 91%.

Preparation of L-Tryptophan 1

General Procedure

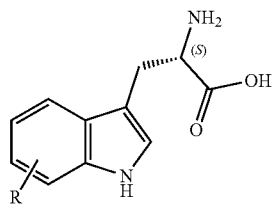

A 60 mM solution of intermediate 7 in 2:1 mixture of THF/1 M HCl was subjected to disassembly under microwave reaction condition. The disassembly was carried out in a sealed glass tube in a CEM microwave reactor at 50 W and 75° C. for 40 min until the red colour of the solution disappeared. The pressure was monitored and did not exceed 40 psi. The reaction mixture was cooled to room temperature and extracted with Et$_2$O and the aqueous layer was evaporated to dryness. A small fraction was purified using ion-exchange chromatography and the bulk of the crude was subjected to Fmoc-derivatisation.

(S)-2-Amino-3-(4-fluoro-1H-indol-3-yl)propanoic acid (L-tryptophan 1a)

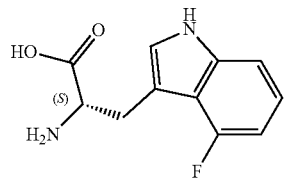

The disassembly of intermediate 7a (0.72 g, 0.97 mmol) was carried out using the general procedure, to yield the title compound as a crude mixture. A small fraction was purified using ion-exchange chromatography and the bulk of the crude was subjected to Fmoc-derivatisation; m.p. 224-226° C. (Lit. m.p. 230-233° C.); $[\alpha]_D^{24}$=-27.5° (c=0.4, MeOH) (Lit. $[\alpha]_D^{24}$=-28.7° (c=0.9, H$_2$O)); $^1$H-NMR (400 MHz, D$_2$O): δ=3.27 (dd, J=15, 8 Hz, 1H, CH$_A$CH$_B$), 3.42 (dd, J=15, 5 Hz, 1H, CH$_A$CH$_B$), 4.03 (dd, J=8, 5 Hz, 1H, α-H), 7.04 (dt, J=9, 3 Hz 1H, CH-6), 7.34 (s, 1H, CH-2), 7.40 (dd, J=10, 3 Hz, 1H, CH-7), 7.89 (dd, J=9, 5 Hz, 1H, CH-5) ppm; $^{13}$C-NMR (100 MHz, D$_2$O): δ=26.3, 55.0, 103.1 (d, J=25 Hz), 107.7 (d, J=5 Hz), 110.3 (d, J=27 Hz), 112.7 (d, J=11 Hz), 126.7, 126.9 (d, J=9 Hz), 132.9, 157.5 (d, J=232 Hz), 174.4 ppm; MS: m/z (+ESI) calcd. for $C_{11}H_{12}N_2O_2Na^+$ 227.0791, found 227.0923 [MNa$^+$ (-F)]; RP-HPLC Method 2, $t_R$ 4.73 min.

(S)-2-Amino-3-(4-chloro-1H-indol-3-yl)propanoic acid (L-tryptophan 1b)

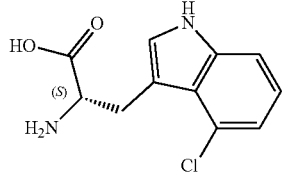

The disassembly of intermediate 7b (0.3 g, 0.4 mmol) was carried out using the general procedure, to yield the title compound as a crude mixture. A small fraction was purified using ion-exchange chromatography and the bulk of the crude was subjected to Fmoc-derivatisation; m.p. 224-226° C.; $[\alpha]_D^{24}$=−40.2° (c=0.15, MeOH); $^1$H-NMR (400 MHz, acetone-$d_6$): δ=3.13 (dd, J=10, 15 Hz, 1H, CH$_A$CH$_B$), 3.78 (dd, J=16, 4 Hz, 1H, CH$_A$CH$_B$), 4.12 (dd, J=16, 4 Hz, 1H, α-H), 7.02 (dd, J=8, 1 Hz, 1H, Ar H), 7.06 (t, J=8 Hz, 1H, Ar H), 7.36 (s, 1H, Ar H), 7.38 (dd, J=8, 1 Hz, 1H, Ar), 10.42 (br, 1H, COOH) ppm; $^{13}$C-NMR (100 MHz, acetone-$d_6$): δ=27.2, 54.7, 107.4, 110.9, 119.9, 122.4, 123.6, 124.8, 127.3, 138.3 ppm; MS: m/z (+ESI) calcd. for $C_{11}H_{12}ClN_2O_2^+$239.0582, found 238.3884 [MH$^+$]; RP-HPLC Method 2, $t_R$ 5.73 min.

(S)-2-Amino-3-(4-bromo-1H-indol-3-yl)propanoic acid (L-tryptophan 1c)

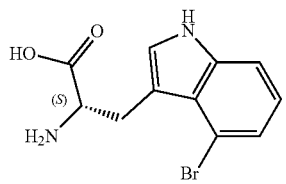

The disassembly of intermediate 7c (1.04 g, 1.29 mmol) was carried out using the general procedure, to yield the title compound as a crude mixture. A small fraction was purified using ion-exchange chromatography; m.p. 262-263° C.; $[\alpha]_D^{24}$=−19.4° (c=0.12, MeOH); $^1$H-NMR (400 MHz, D$_2$O): δ=3.26 (dd, J=16, 8 Hz, 1H, CH$_A$CH$_B$), 3.43 (dd, J=15, 5 Hz, 1H, CH$_A$CH$_B$), 4.03 (dd, J=8, 5 Hz, 1H, α-H), 7.31 (s, 1H, CH-2), 7.36 (dd, J=9, 2 Hz, 1H, CH-6), 7.43 (d, J=9 Hz, 1H, CH-7), 7.89 (d, J=2 Hz, 1H, CH-5) ppm; $^{13}$C-NMR (100 MHz, D$_2$O): δ=26.6, 54.8, 107.3, 112.0, 113.6, 120.8, 124.7, 126.2, 128.4, 135.1 ppm; MS: m/z (+ESI) calcd. for $C_{11}H_{12}BrN_2O_2^+$283.0077, found 238.3902 [MH$^+$]; RP-HPLC Method 2, $t_R$ 6.59 min.

(S)-2-Amino-3-(4-(trifluoromethyl)-1H-indol-3-yl)propanoic acid (L-tryptophan 1d)

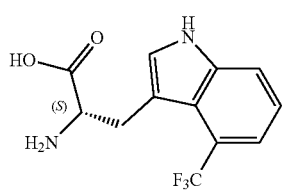

The disassembly of intermediate 7d (0.4 g, 0.5 mmol) was carried out using the general procedure, to yield the title compound as a crude mixture. A small fraction was purified using ion-exchange chromatography; m.p. 230-232° C.; $[\alpha]_D^{24}$=−24.4° (c=0.25, MeOH);
$^1$H-NMR (400 MHz, D$_2$O): δ=3.27 (dd, J=16, 9 Hz, 1H, CH$_A$CH$_B$), 3.62 (dd, J=15, 5 Hz, 1H, CH$_A$CH$_B$), 4.23 (m, 1H, α-H), 7.32 (t, J=8 Hz, 1H, CH-6), 7.47 (s, 1H, CH-2), 7.56 (d, J=8 Hz, 1H, CH-7), 7.89 (d, J=8 Hz, 1H, CH-5) ppm; $^{13}$C-NMR (100 MHz, D$_2$O): δ=27.2, 53.8, 106.2, 116.7, 118.3 (d, J=6 Hz), 119.7 (d, J=33 Hz), 121.0, 123.7, 126.4, 128.4, 137.6, 172.4 ppm; MS: m/z (+ESI) calcd. for $C_{12}H_{12}F_3N_2O_2^+$273.0845, found 272.4302 [MH$^+$]; RP-HPLC Method 2, $t_R$ 7.21 min.

(S)-2-Amino-3-(4,5-dichloro-1H-indol-3-yl)propanoic acid (L-tryptophan 1e)

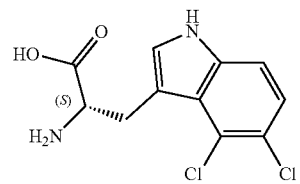

The disassembly of intermediate 7e (0.63 g, 0.79 mmol) was carried out using the general procedure, to yield the title compound as a crude mixture. A small fraction was purified using ion-exchange chromatography; m.p. 233-235° C.; $[\alpha]_D^{24}$=−42.5° (c=0.15, MeOH);
$^1$H-NMR (400 MHz, D$_2$O): δ=3.23 (dd, J=15, 9 Hz, 1H, CH$_A$CH$_B$), 3.81 (dd, J=15, 6 Hz, 1H, CH$_A$CH$_B$), 4.37 (dd, J=9, 6 Hz, 1H, α-H), 7.28 (d, J=9 Hz, 1H, Ar H), 7.31 (s, 1H, Ar H), 7.36 (d, J=9 Hz, 1H, Ar) ppm; $^{13}$C-NMR (100 MHz, D$_2$O): δ=27.1, 54.7, 107.3, 111.9, 122.4, 123.1, 123.5, 128.2, 136.2, 171.8 ppm; MS: m/z (+ESI) calcd. for $C_{11}H_{11}Cl_2N_2O_2^+$273.0192, found 273.1859 [MH$^+$]; RP-HPLC Method 1, $t_R$ 9.71 min.

Preparation of Intermediate 8

General Procedure

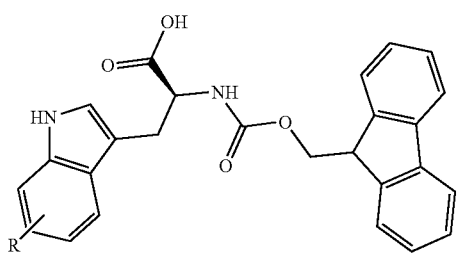

The crude mixture of L-tryptophan 1 (1 equiv.) was dissolved in aqueous solution of sodium carbonate (3 equiv.). To this, a solution of Fmoc succinimide (1 equiv.), dissolved in anhydrous THF, was added dropwise over 20 min and the resultant reaction mixture was stirred at room temperature for 24 h. The reaction mixture was concentrated under vacuo. The crude mixture was dissolved in water and extracted with EtO$_2$. The aqueous phase was acidified to pH 2 with 1 M aqueous HCl and extracted with EtOAc, dried over MgSO₄ and concentrated under vacuo to afford the product as brown solid.

(S)-2-((((9H-Fluoren-9-yl)methoxy)carbonyl)amino)-3-(4-fluoro-1H-indol-3-yl)propanoic acid (Intermediate 8a)

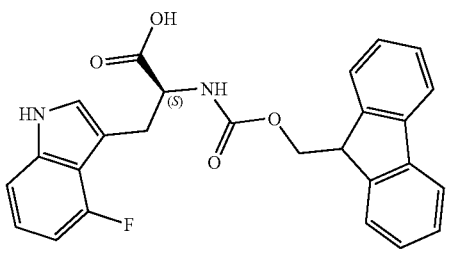

Synthesis was carried out using the general procedure, using crude L-tryptophan 1a (0.19 g, 0.85 mmol) in 5 mL of sodium carbonate (0.27 g, 2.55 mmol) and Fmoc succinimide (0.29 g, 0.85 mmol) dissolved in anhydrous THF (10 mL) to yield the title compound as brown solid (0.2 g, 53% yield); m.p. 68-70° C.; $R_f$=0.3 (1% AcOH in CHCl₃/MeOH, 9:1); ¹H-NMR (400 MHz, CDCl₃): δ=3.23 (dd, J=15, 8 Hz, 1H, CH$_A$H$_B$), 3.39 (m, 1H, CH$_A$H$_B$), 4.15 (m, 2H, Fmoc CH₂), 4.29 (t, J=9 Hz, 1H, Fmoc CH), 4.53 (m, 1H, α-H), 6.58 (d, 7 Hz, 1H, NH), 6.84 (t, J=9 Hz, 1H, Ar H), 7.23 (m, 2H, Ar Hs), 7.31-7.36 (m, 5H, Ar Hs), 7.58 (dd, J=16, 7.5 Hz, 2H, Ar Hs), 7.80 (d, J=8 Hz, 2H, Ar Hs), 10.14 (br, 1H, CO₂H) ppm; ¹³C-NMR (100 MHz, CDCl₃): δ=27.4, 47.1, 47.0, 55.5, 59.5, 66.2, 96.9, 103.1 (d, J=23 Hz), 108.9, 109.1, 119.7, 125.2 (d, J=7 Hz), 125.7, 126.9, 127.4, 133.0 (d, J=14 Hz), 141.0 (d, J=4 Hz), 144.1 (d, J=3 Hz), 148.0, 151.7, 153.0, 157.4 (d, J=232 Hz) ppm; MS: m/z (+ESI) calcd. for C₂₆H₂₂FN₂O₄⁺445.1558, found 445.1790 [MH⁺].

(S)-2-((((9H-Fluoren-9-yl)methoxy)carbonyl)amino)-3-(4-chloro-1H-indol-3-yl)propanoic acid (Intermediate 8b)

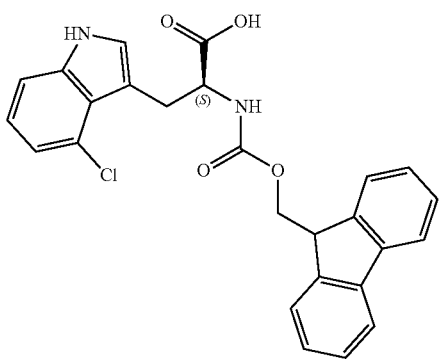

Synthesis was carried out using the general procedure, using L-tryptophan 1b (0.36 g, 1.26 mmol) in 10 mL of sodium carbonate (0.4 g, 3.78 mmol) and Fmoc succinimide (0.42 g, 1.26 mmol) dissolved in anhydrous THF (10 mL) to yield the title compound as brown solid (0.45 g, 46% yield); m.p. 102-104° C.; $R_f$=0.3 (1% AcOH in CHCl₃/MeOH, 9:1); $[α]_D^{24}$=−10.3° (c=0.55, MeOH); ¹H-NMR (400 MHz, acetone-d₆): δ=3.25 (dd, J=15, 8 Hz, 1H, CH$_A$H$_B$), 3.39 (dd, J=14, 5 Hz, 1H, CH$_A$H$_B$), 4.19 (t, J=9 Hz, 1H, Fmoc CH), 4.28 (m, 2H, Fmoc CH₂), 4.60 (m, 1H, α-H), 6.69 (d, J=9 Hz, 1H, NH), 7.09 (dd, J=9, 2 Hz, 1H, Ar H), 7.28 (m, 2H, Ar Hs), 7.32 (s, 1H, Ar H), 7.36-7.41 (m, 3H, Ar Hs), 7.64 (dd, J=8, 4 Hz, 2H, Ar Hs), 7.68 (d, J=2 Hz, 1H, Ar Hs), 7.83 (d, J=8 Hz, 2H, Ar Hs), 10.29 (br, 1H, CO₂H) ppm; ¹³C-NMR (100 MHz, acetone-d₆): δ=28.1, 48.0, 55.6, 67.2, 111.3, 113.6, 113.62, 118.8, 120.7, 122.3, 125.1, 126.1, 126.4, 128.0, 128.5, 129.9, 135.8, 136.0, 142.1, 142.1, 145.0, 145.05, 156.9, 173.6 ppm; MS: m/z (+ESI) calcd. for C₂₆H₂₂ClN₂O₄⁺461.1263, found 461.1317 [MH⁺].

(S)-2-((((9H-Fluoren-9-yl)methoxy)carbonyl)amino)-3-(4-bromo-1H-indol-3-yl)propanoic acid (Intermediate 8c)

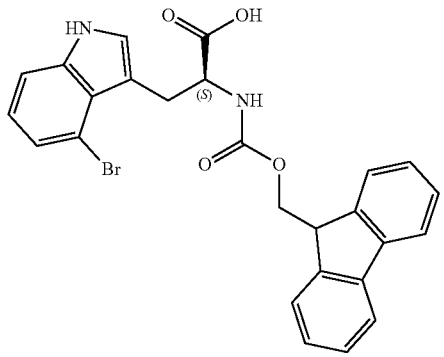

Synthesis was carried out using the general procedure, using L-tryptophan 1c (0.36 g, 1.26 mmol) in 10 mL of sodium carbonate (0.4 g, 3.78 mmol) and Fmoc succinimide (0.42 g, 1.26 mmol) dissolved in anhydrous THF (10 mL) to yield the title compound as brown solid (0.19 g, 30% yield); m.p. 90-93° C.; $R_f$=0.3 (1% AcOH in CHCl₃/MeOH, 9:1); $[α]_D^{24}$=−22.3 (c=1.0, MeOH); ¹H-NMR (400 MHz, acetone-d₆): δ=3.25 (dd, J=14, 8 Hz, 1H, CH$_A$H$_B$), 3.40 (dd, J=14, 5 Hz, 1H, CH$_A$H$_B$), 4.19 (t, J=7 Hz, 1H, Fmoc CH), 4.28 (m, 2H, Fmoc CH₂), 4.61 (m, 1H, α-H), 7.21 (dd, J=14, 8 Hz, 1H, Ar H), 7.28 (m, 2H, Ar Hs), 7.32 (s, 1H, Ar H), 7.36-7.40 (m, 3H, Ar Hs), 7.64 (dd, J=8, 3 Hz, 2H, Ar Hs), 7.80-7.87 (m, 3H, Ar Hs), 10.35 (br, 1H, COOH) ppm; ¹³C-NMR (100 MHz, acetone-d₆): δ=26.1, 28.0, 47.9, 55.6, 67.2, 111.1, 112.7, 114.0, 120.7, 121.8, 124.8, 126.0, 126.1, 126.2, 127.9, 128.5, 130.5, 136.0, 142.0, 142.02, 145.95, 145.0, 156.9, 172.6, 173.6 ppm; MS: m/z (+ESI) calcd. for C₂₆H₂₂BrN₂O₄⁺505.3755, found 505.6674 [MH⁺]; RP-HPLC Method 1, $t_R$ 11.77 min.

(S)-2-((((9H-Fluoren-9-yl)methoxy)carbonyl)amino)-3-(4-(trifluoromethyl)-1H-indol-3-yl)propanoic acid (Intermediate 8d)

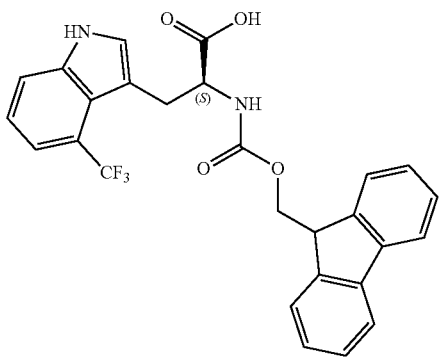

Synthesis was carried out using the general procedure, using L-tryptophan 1d (0.14 g, 0.5 mmol) in 10 mL of sodium carbonate (0.16 g, 1.5 mmol) and Fmoc succinimide (0.17 g, 0.5 mmol) dissolved in anhydrous THF (10 mL) to yield the title compound as brown solid (84 mg, 34% yield); m.p. 118-120° C.; $R_f$=0.3 (1% AcOH in CHCl$_3$/MeOH, 9:1); $[\alpha]_D^{24}$=−7.4 (c=0.18, MeOH); $^1$H-NMR (400 MHz, acetone-d$_6$): δ=3.21 (dd, J=15, 8 Hz, 1H, CH$_A$H$_B$), 3.36 (dd, J=15, 6 Hz, 1H, CH$_A$H$_B$), 4.15 (t, J=7 Hz, 1H, Fmoc CH), 4.26 (m, 2H, Fmoc CH$_2$), 4.58 (m, 1H, α-H), 6.63 (d, J=8 Hz, NH), 6.89 (td, J=9, 3 Hz, 1H, Ar H), 7.09 (dd, J=10, 2 Hz, 1H, Ar H), 7.22 (s, 1H, C-2H), 7.25 (m, 2H, Ar Hs), 7.35 (t, J=8 Hz, 2H, Ar Hs), 7.60 (m, 3H, Ar Hs), 7.80 (d, J=8 Hz, 2H, Ar Hs), 10.14 (br, 1H, NH) ppm; $^{13}$C-NMR (100 MHz, acetone-d$_6$): δ=47.9, 55.6, 67.2, 98.2 (d, J=27 Hz), 108.1 (d, J=25 Hz), 111.5, 120.2 (d, J=10 Hz), 120.8, 125.0 (d, J=4 Hz), 125.4, 126.2, 127.9, 128.5, 137.4 (d, J=13 Hz), 142.0, 145.0 (d, J=5 Hz), 156.9, 160.6 (d, J=233 Hz), 173.7 ppm; MS: m/z (+ESI) calcd. for C$_{27}$H$_{22}$F$_3$N$_2$O$_4$$^+$495.1526, found 495.2201 [MH$^+$].

(S)-2-((((9H-Fluoren-9-yl)methoxy)carbonyl)amino)-3-(4,5-dichloro-1H-indol-3-yl)propanoic acid (Intermediate 8e)

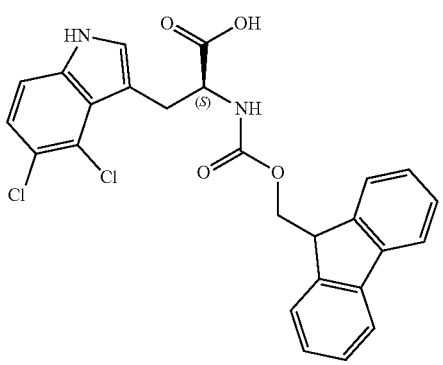

Synthesis was carried out using the general procedure, using L-tryptophan 1e (0.21 g, 0.77 mmol) in 10 mL of sodium carbonate (0.24 g, 2.3 mmol) and Fmoc succinimide (0.26 g, 0.77 mmol) dissolved in anhydrous THF (10 mL) to yield the title compound as brown solid (0.1 g, 26% yield); m.p. 130-132° C.; $R_f$=0.3 (1% AcOH in CHCl$_3$/MeOH, 9:1); $[\alpha]_D^{25}$=−44.8° (c=0.9, MeOH); $^1$H-NMR (400 MHz, acetone-d$_6$): δ=3.29 (dd, J=15, 10 Hz, 1H, CH$_A$H$_B$), 3.78 (dd, J=15, 5 Hz, 1H, CH$_A$H$_B$), 4.15 (t, J=7 Hz, 1H, Fmoc CH), 4.23 (m, 2H, Fmoc CH$_2$), 4.70 (m, 1H, α-H), 6.82 (d, J=9 Hz, 1H, NH), 7.21-7.31 (m, 3H, Ar Hs), 7.37-7.43 (m, 4 h, Ar Hs)), 7.64 (dd, J=8, 4 Hz, 2H, Ar Hs), 7.84 (d, J=8 Hz, 2H, Ar Hs), 10.58 (br, 1H, NH) ppm; $^{13}$C-NMR (100 MHz, acetone-d$_6$): δ=48.0, 67.1, 112.2, 112.6, 120.8, 123.7, 123.73, 123.9, 126.2, 127.9, 128.2, 128.5, 137.5, 142.0, 145.0, 163.0, 183.7, 187.1, 194.1 ppm; MS: m/z (+ESI) calcd. for C$_{26}$H$_{21}$Cl$_2$N$_2$O$_4$$^+$495.0873, found 495.1631 [MH$^+$]; RP-HPLC Method 2, t$_R$ 6.40 min.

Preparation of Intermediate 9c (Z)-2-((((9H-fluoren-9-yl)methoxy)carbonyl)amino)but-2-enoic acid (Intermediate 9c)

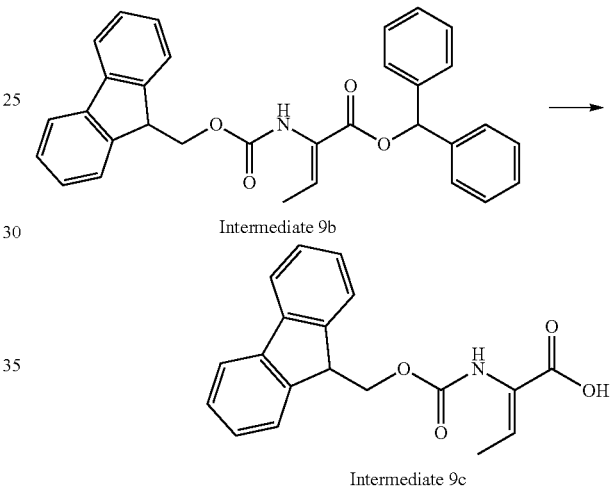

Intermediate 9b (1.50 g, 3.07 mmol) was dissolved in 40 mL DCM/TFA/anisole (20/16/4) and stirred at room temperature for 2 h. The solution was then evaporated in vacuo to dryness and the residual material was extensively triturated with diethyl ether to afford the intermediate 9c as a white solid (0.864 g, 87%); m.p. 226.6-227.5° C.; $R_f$=0.17 (EtOAc/hexane/AcOH, 10:10:0.1); $^1$H-NMR (400 MHz, DMSO-d$_6$): δ=1.74 (d, J=7 Hz, 3H, CH$_3$), 4.25 (m, 1H, Fmoc-CH), 4.38 (d, J=7 Hz, 2H, Fmoc-CH$_2$), 6.75 (q, J=14, 7 Hz, 1H, CH), 7.29 (m, 3H, ArHs), 7.37 (m, 2H, ArHs), 7.67 (m, 2H, ArHs), 7.79 (d, J=7 Hz, 2H, ArHs) ppm; $^{13}$C-NMR (100 MHz, DMSO-d$_6$): δ=13.7, 47.1, 120.6, 125.7, 127.2, 127.5, 128.1, 128.8, 129.1, 129.5, 129.7, 141.2, 144.2; MS: m/z (+ESI) calcd. for C$_{19}$H$_{18}$NO$_4$$^+$ 324.1230, found 324.1237 [MH$^+$].

Preparation of the Compounds of the Invention

Preparation of Linear Precursors

For the Fmoc/tBu solid-phase peptide synthesis (SPPS) of the compounds, 2-chlorotrityl chloride polystyrene resin was used as the solid support to furnish the linear peptide acid precursor. Intermediate 9c- and 9d-containing linear precursors were cleaved and cyclised in solution. Intermediate 9a containing linear precursors were subjected to on resin oxidative elimination before the linear peptides were cleaved and cyclised in solution as depicted in Scheme 5.

Scheme 5: Fmoc/tBu-SPPS and solution-phase macrocyclisation of the compounds of the invention
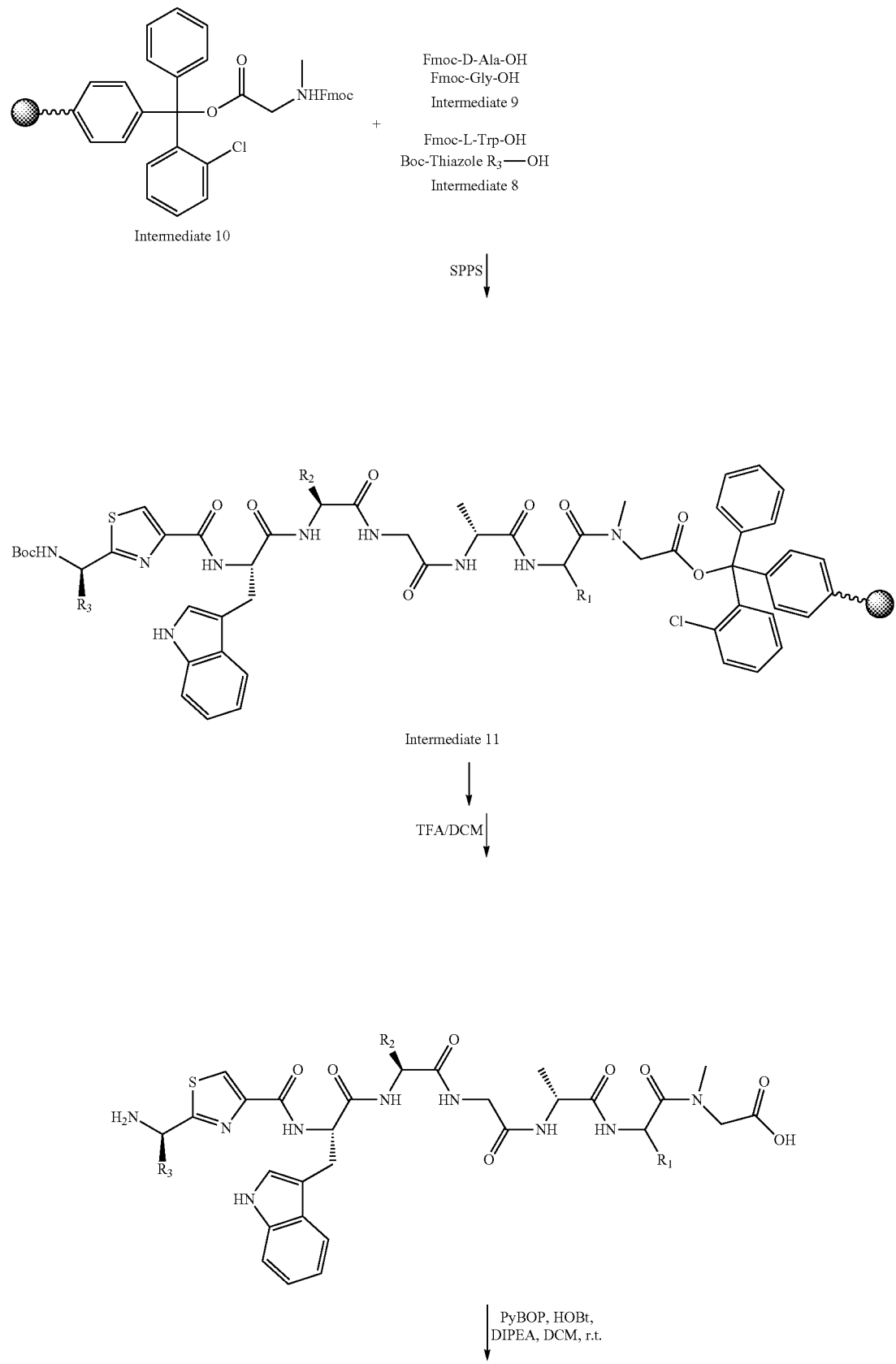

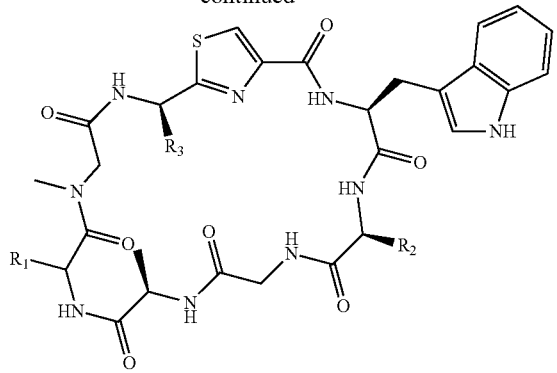

Argyrin

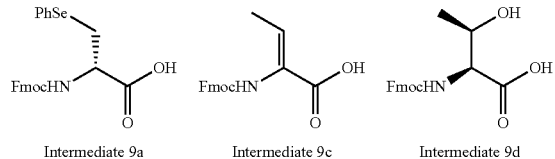

Intermediate 9a    Intermediate 9c    Intermediate 9d

Preparation of Intermediate 10

2-Chlorotrityl polystyrene 2-[N-(fluoren-9-yl-methoxycarbonyl)methylamino] acetate (Intermediate 10)

2-Chlorotrityl resin (1.0 g, 1.2 mmol loading) was placed in a round bottom flask and swollen with DCM for 1.5 h. Fmoc-Sar-OH (0.37 g, 1.2 mmol) and DIPEA (0.42 mL, 2.4 mmol) were dissolved in 2 mL DCM and added to the flask containing the resin. After stirring for 2-3 h, methanol (10 mL) was added to the resin mixture and stirred for a further 10 min. Subsequently, the resin was filtered, washed successively with DMF, DCM and hexane, and dried in vacuo to yield the resin product. (1.37 g, 100% yield). Fmoc-substitution was determined to be 0.787 mmol g$^{-1}$ (66%).

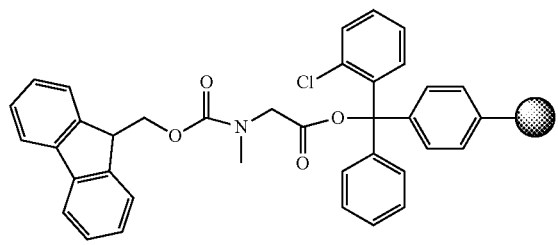 [SMILES: Cc1ccc(C(OC(=O)CN(C)C(=O)OCC2c3ccccc3-c3ccccc32)(c2ccccc2)c2ccccc2Cl)cc1]

General Procedure for the Preparation of Intermediate 11

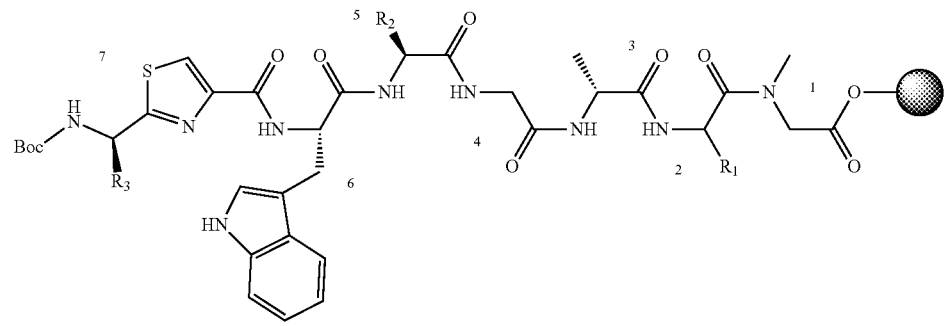

The resin product (Intermediate 10) (1 equiv.) was placed in an Omnifit™ continuous flow glass column (150×10 mm) and swollen with a mixture of DMF/DCM 1:1 for 15 h. The resin was washed under continuous flow of DMF (2.8 mL min$^{-1}$, 6 min). Fmoc deprotection was carried out under continuous flow of 20% v/v piperidine in DMF (2.8 mL min$^{-1}$, 6 min) and washed with DMF ((2.8 mL min$^{-1}$, 6 min). Washing and deprotection steps were carried out using a NOVA SYN® GEM peptide manual synthesiser and the reaction was monitored post column at 344 nM. Sequential acylation reactions were carried out for 4-12 h at ambient temperature in the reaction column using appropriately Na-protected amino acid (4 equiv.), carboxyl-activating reagent HATU (3.9 equiv.) and DIPEA (8 equiv.) dissolved in 0.6-1.0 mL of DMF. Each acylation reaction was followed by wash and deprotection step as described above. After the desired sequence Boc-$R_3$-Thz$^7$-Trp$^6$-$R_2^5$-Gly$^4$-$R_1^3$-Ph(Se)$^2$—OH was assembled, the resin was washed with DMF (15 min, 2.5 mL min$^{-1}$), filtered and washed successively with DMF, DCM and hexane, and dried in vacuo.

General Procedure for On-Resin Oxidative Elimination of Intermediate 10a

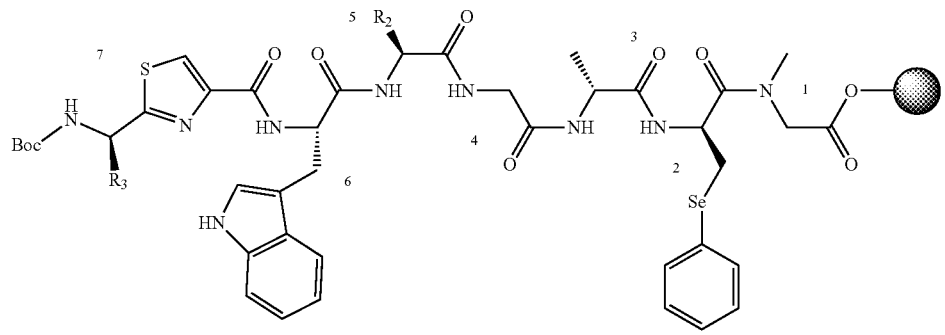

Intermediate 11a-I

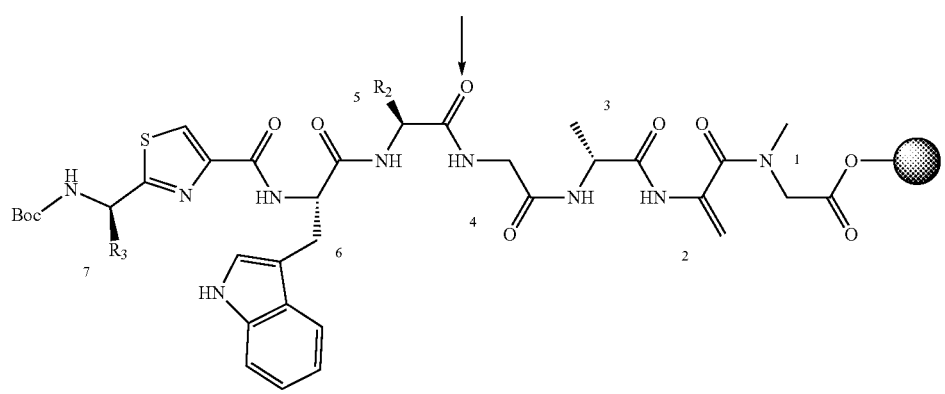

Intermediate 12a-I

The resin bound intermediate 11b-1 (1 equiv.) was placed in an Omnifit™ continuous flow glass column (150×10 mm) and swollen with DMF/DCM 1:1 mixture for 15 h. The resin was washed with DMF (5 mL) and a solution of NaIO$_4$ (2 equiv.) dissolved in DMF/H$_2$O 1:1 (1 mL) added to the column and stirred intermittently at ambient temperature until the reaction completed as determined by RP-HPLC. The resin was washed successively with DMF (5 mL), H$_2$O (20 mL) and DMF (15 mL), filtered, washed successively with DCM and hexane, and dried under vacuo to afford intermediate 12b-1.

General Procedure for Acidolytic Cleavage of Intermediate 12

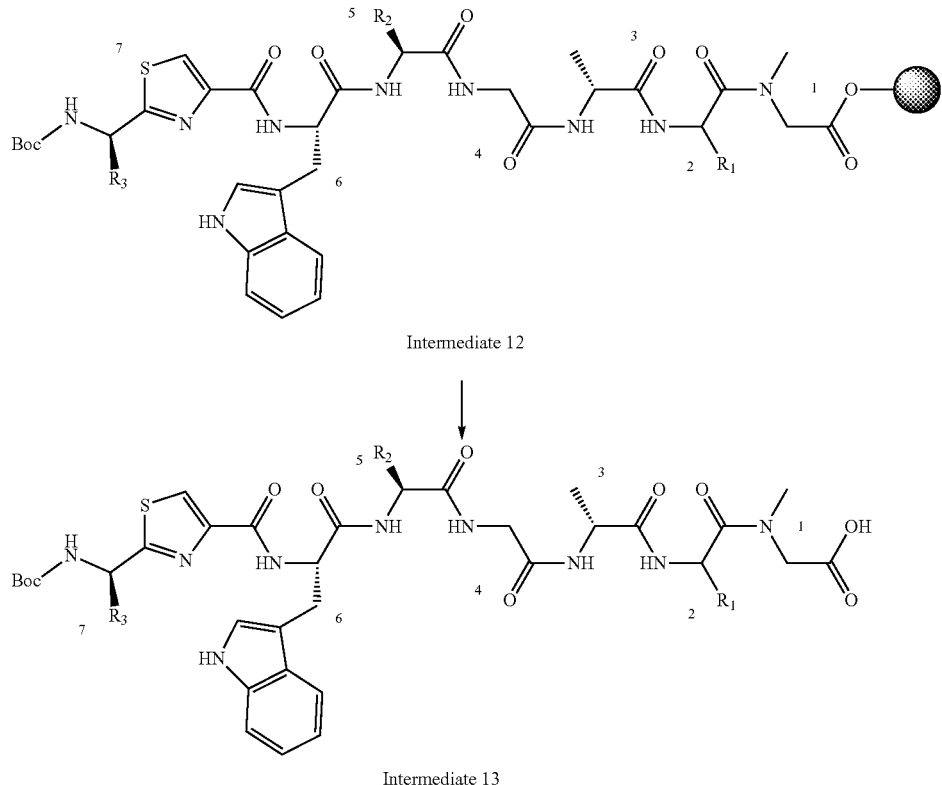

Intermediate 12

↓

Intermediate 13

The peptidyl resin was suspended in a mixture of TFA/DCM, 1:1 (10 mL) for 2 h. The resin was filtered, washed with DCM and the filtrate was concentrated under vacuo. The residual material was triturated with diethyl ether to afford the crude peptide which was analysed using RP-HPLC. The crude intermediate 13 was subjected to cyclisation without purification.

H-D-Ser(OMe)-Thz-Trp-Trp(4-Br)-Gly-D-Ala-Dha-Sar-OH (Intermediate 13b)

Crude yield: 40.9 mg, 89%; ES-MS m/z calcd. for $C_{40}H_{46}BrN_{10}O_9S^+$ 923.2327, found 923.2436 [MH$^+$]; RP-HPLC Method 1, $t_R$ 6.58 min.

H-D-Ala-Thz-Trp-Trp(4-Cl)-Gly-D-Ala-Dha-Sar-OH (Intermediate 13c)

Crude yield: 71.6 mg, 86%; ES-MS m/z calcd. for $C_{39}H_{44}ClN_{10}O_8S^+$ 847.2724, found 847.3101 [MH$^+$]; RP-HPLC Method 1, $t_R$ 6.10 min.

H-D-Ala-Thz-Trp-Trp(4-Br)-Gly-D-Ala-Dha-Sar-OH (Intermediate 13d)

Crude yield: 79.2 mg, 89%; ES-MS m/z calcd. for $C_{39}H_{44}BrN_{10}O_8S^+$ 891.2242, found 890.9951 [MH$^+$]; RP-HPLC Method 1, $t_R$ 6.37 min.

H-D-Ala-Thz-Trp-Trp(4-F)-Gly-D-Ala-Dha-Sar-OH (Intermediate 13e)

Crude yield: 66.4 mg, 80%; ES-MS m/z calcd. for $C_{39}H_{44}FN_{10}O_8S^+$ 831.3043, found 831.3075 [MH$^+$]; RP-HPLC Method 1, $t_R$ 5.77 min.

H-D-Ala-Thz-Trp-Trp(4-CF$_3$)-Gly-D-Ala-Dha-Sar-OH (Intermediate 13f)

Crude yield: 66.0 mg, 75%; ES-MS m/z calcd. for $C_{40}H_{44}F_3N_{10}O_8S^+$ 881.3011, found 880.9564 [MH$^+$]; RP-HPLC Method 1, $t_R$ 7.11 min.

H-D-Ala-Thz-Trp-Trp-(4,5-Cl)-Gly-D-Ala-Dha-Sar-OH (Intermediate 13 h)

Crude yield: 62.6 mg, 71%; ES-MS m/z calcd. for $C_{39}H_{43}Cl_2N_{10}O_8S^+$ 882.7945, found 882.9157 [MH$^+$]; RP-HPLC Method 1, $t_R$ 7.03 min.

H-D-Ser-Thz-Trp-Trp(4-Cl)-Gly-D-Ala-Dha-Sar-OH (Intermediate 13i)

Crude yield: 73.3 mg, 85%; ES-MS m/z calcd. for $C_{39}H_{44}ClN_{10}O_9S^+$ 863.2696, found 862.9593 [MH$^+$]; RP-HPLC Method 1, $t_R$ 5.99 min.

H-D-Ala-Thz-Trp-Trp(4-Cl)-Gly-D-Ala-Thr-Sar-OH (Intermediate 13m)

Crude yield: 76.4 mg, 87%; ES-MS m/z calcd. for $C_{40}H_{48}ClN_{10}O_9S^+$ 879.3009, found 878.9748 [MH$^+$]; RP-HPLC Method 1, $t_R$ 5.12 min.

H-D-Ala-Thz-Trp-Trp(4-Cl)-Gly-D-Ala-Dhb-Sar-OH (Intermediate 13n)

Crude yield: 19.0 mg, 44%; ES-MS m/z calcd. for $C_{40}H_{46}ClN_{10}O_8S^+$ 861.2904, found 861.6 [MH$^+$]; RP-HPLC Method 1, $t_R$ 6.50 min.

H-D-Ala-Thz-Trp-Trp(4-Br)-Gly-D-Ala-Dhb-Sar-OH (Intermediate 13o)

Crude yield: 39 mg, 84%; ES-MS m/z calcd. for $C_{40}H_{45}BrN_{10}NaO_8S^+$ 927.2218, found 927.2190 [MNa$^+$]; RP-HPLC Method 1, $t_R$ 6.58 min.

H-D-Ser(OMe)-Thz-Trp-Trp(4-Br)-Gly-D-Ala-Dhb-Sar-OH (Intermediate 13p)

Crude yield: 162 mg; ES-MS m/z calcd. for $C_{41}H_{47}BrN_{10}NaO_9S^+$ 957.2324, found 957.2304 [MNa$^+$]; RP-HPLC Method 1, $t_R$ 6.60 min.

H-D-Ala-Thz-Trp-Trp(4-Br)-Gly-D-Ala-Dhp-Sar-OH (Intermediate 13q)

Crude yield: 50 mg, 82%; ES-MS m/z calcd. for $C_{45}H_{48}BrN_{10}O_8S^+$ 967.2561, found 967.2553 [MH$^+$]; RP-HPLC Method 1, $t_R$ 7.59 min.

H-D-Ala-Thz-Trp-Trp(4-Br)-Gly-D-Ala-Dhv-Sar-OH (Intermediate 13r)

Crude yield: 44 mg, 80%; ES-MS m/z calcd. for $C_{47}H_{48}BrN_{10}O_8S^+$ 919.2561, found 919.2546 [MH$^+$]; RP-HPLC Method 1, $t_R$ 6.93 min.

H-D-Ala-Thz-Trp-Trp(4-Br)-Gly-D-Ala-Dhl-Sar-OH (Intermediate 13s)

Crude yield: 48 mg, 81%; ES-MS m/z calcd. for $C_{42}H_{50}BrN_{10}O_8S^+$ 933.2717, found 933.2725 [MH$^+$]; RP-HPLC Method 1, $t_R$ 7.58 min.

Macrocyclisation of the Compounds of the Invention
General Procedure for the Head-to-Tail Cyclisation

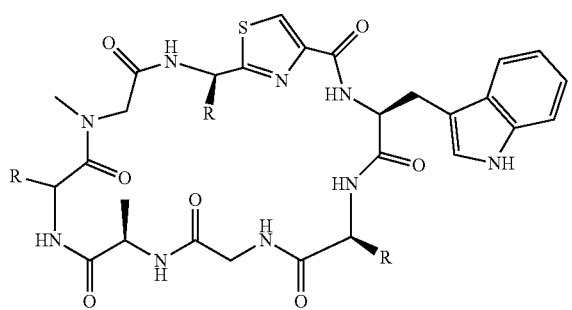

PyBOP (2 equiv.), HOBt (2 equiv.) and DIPEA (9 equiv.) were added successively to a 0.5 mM solution of crude linear peptide (1 equiv.) in DCM. The reaction mixture was stirred for 96 h or until completion is determined by RP-HPLC. The crude mixture was concentrated under vacuo and purified using semi-preparative RP-HPLC.

Cyclo(D-Ala-D-Thiazole-L-Trp-L-Trp-Gly-D-Ala-Dha-Sar) (Argyrin E)—Reference Example

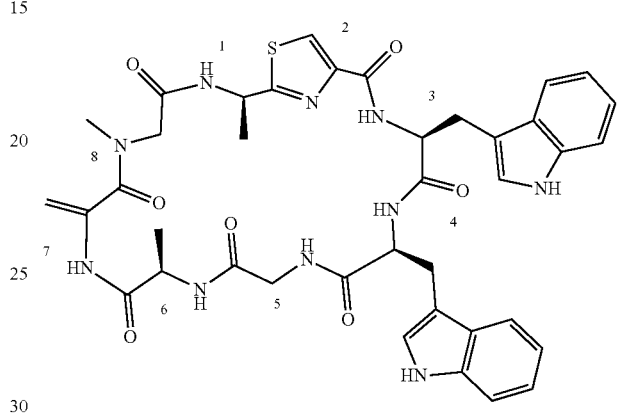

Synthesis was carried out using the general procedure for head-to-tail cyclisation employing PyBOP (0.1 g, 0.2 mmol), HOBt (0.03 g, 0.2 mmol) and DIPEA (156.5 μL, 0.9 mmol) in a 0.5 mM solution of crude linear peptide (Intermediate 13k) (0.13 g, 0.1 mmol). The crude mixture was concentrated under vacuo and purified using semi-preparative RP-HPLC (Onyx monolithic-C18 semi-preparative column (100×10 mm) at 9 mL min$^{-1}$) and freeze dried to afford the title peptide as white powder (5.5 mg, 7% yield); $[\alpha]_D^{22}$=+107.8° (c=0.51, MeOH);

$^1$H-NMR (400 MHz, DMSO-d$_6$): δ=1.65 (d, J=7 Hz, 3H, 6-CH$_3$), 2.33 (d, J=7 Hz, 3H, 1-CH$_3$), 3.90 (s, 3H, 8-CH$_3$), 3.93 (m, 2H, 4-CH$_2$), 4.00 (m, 1H, 3-CH$_A$H$_B$), 4.15 (m, 1H, 8-CH$_A$H$_B$), 4.20 (m, 1H, 5-CH$_A$H$_B$), 4.24 (m, 1H, 3-CH$_A$H$_B$), 4.56 (m, 1H, 8-CH$_A$H$_B$), 4.61 (m, 1H, 5-CH$_A$H$_B$), 4.67 (m, 1H, 4-α-CH), 5.01 (m, 1H, 6-α-CH), 5.06 (m, 1H, 3-α-CH), 5.12 (m, 2H, 7-CH2), 5.56 (m, 1H, 1-α-CH), 6.18 (m, 1H, Ar H), 7.72 (t, J=7 Hz, 1H, Ar H), 7.80 (m, 2H, Ar Hs), 7.88 (t, J=7 Hz, 1H, Ar H), 7.98 (dd, J=12, 1 Hz, 2H, Ar Hs), 8.06 (d, J=8 Hz, 1H, Ar H), 8.15 (d, J=8 Hz, 1H, Ar H), 8.36 (d, J=8 Hz, 1H, Ar H), 8.55 (d, J=8 Hz, 1H, Ar H), 8.78 (s, 1H, 2-CH), 8.90 (d, J=8 Hz, 1H, 6-NH), 9.05 (d, J=9 Hz, 1H, 1-NH), 9.19 (s, 1H, 3-NH), 9.34 (d, J=9 Hz, 1H, 4-NH), 9.48 (s, 1H, 5-NH), 9.97 (s, 1H, 7-NH), 11.53 (s, 1H, indole-NH), 11.7 (s, 1H, indole-NH) ppm; MS: m/z (+ESI) calcd. for $C_{39}H_{42}N_{10}O_7S^+$ 795.2992, found 795.3044 [MH$^+$]; RP-HPLC Method 1, $t_R$ 7.38 min.

Cyclo[D-Ala-Thz-Trp-Trp(4-MeO)-Gly-D-Ala-Dha-Sar] (Argyrin A)—Reference Example

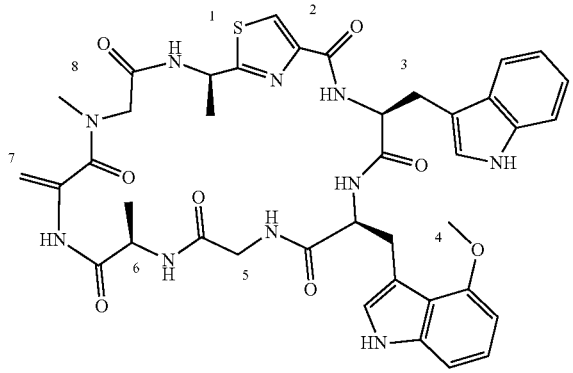 [SMILES: C=C1NC(=O)[C@@H](C)NC(=O)CNC(=O)[C@H](Cc2c[nH]c3cccc(OC)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (41.6 mg, 0.08 mmol), HOBt (12.2 mg, 0.08 mmol) and DIPEA (55.5 μL, 0.32 mmol) in a 0.5 mM solution of crude linear peptide (Intermediate 13l) (33.5 g, 0.04 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (3.61 mg, 11% yield); $[\alpha]_D^{22}$=+74.6° (c=0.24, MeOH);
$^1$H-NMR (400 MHz, DMSO-d$_6$): δ=0.90 (d, J=7 Hz, 3H, 6-CH$_3$), 1.58 (d, J=7 Hz, 3H, 1-CH$_3$), 3.14 (s, 3H, 8-CH$_3$), 3.20 (m, 1H, 3-CH$_A$H$_B$), 3.23 (m, 1H, 8-CH$_A$H$_B$), 3.26 (m, 2H, 4-CH2), 3.38 (d, J=7 Hz, 1H, 5-CH$_A$H$_B$), 3.41 (m, 1H, 3-CH$_A$H$_B$), 3.86 (m, 2H, 8-CH$_A$H$_B$, 5—CH$_A$H$_B$), 3.92 (s, 3H, 4-OCH$_3$), 4.28 (dt, J=7, 3 Hz, 1H, 4-α-CH), 4.37 (m, 1H, 6-α-CH), 4.80 (td, J=11, 4 Hz, 1H, 3-α-CH), 4.95 (s, 1H, 7-CH$_A$H$_B$), 5.19 (s, 1H, 7-CH$_A$H$_B$), 5.44 (m, 1H, 1-α-CH), 6.53 (d, J=8 Hz, 1H, Ar H), 7.00 (t, J=8 Hz, 2H, Ar Hs), 7.01 (d, J=2 Hz, 2H, Ar Hs), 7.05 (m, 2H, Ar Hs), 7.22 (s, 1H, Ar H), 7.31 (d, J=8 Hz, 1H, Ar H), 7.78 (d, J=8 Hz, 1H, Ar H), 8.02 (s, 1H, 2-CH), 8.17 (d, J=9 Hz, 1H, 6-NH), 8.31 (d, J=9 Hz, 1H, 1-NH), 8.48 (s, 1H, 4-NH), 8.59 (m, 2H, 3-NH and 5-NH), 9.25 (s, 1H, 7-NH), 10.77 (s, 1H, indole-NH), 10.91 (s, 1H, indole-NH) ppm; MS: m/z (+ESI) calcd. for C$_{40}$H$_{44}$N$_{10}$O$_8$S$^+$825.3098, found 825.3117 [MH$^+$]. RP-HPLC Method 1, t$_R$ 6.52 min.

Cyclo[D-Ser(OMe)-Thz-Trp-Trp(4-Br)-Gly-D-Ala-Dha-Sar] (Compound 1)

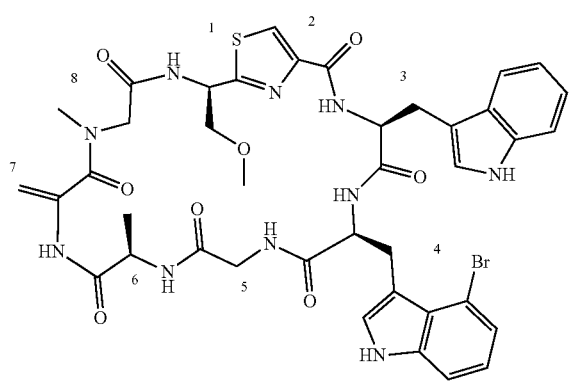 [SMILES: C=C1NC(=O)[C@@H](C)NC(=O)CNC(=O)[C@H](Cc2c[nH]c3cccc(Br)c23)NC(=O)[C@H](Cc2c[nH]c3ccccc23)NC(=O)c2csc(n2)[C@@H](COC)NC(=O)CN(C)C1=O]

Synthesis was carried out using the general procedure for head-to-tail cyclisation employing PyBOP (46 mg, 0.09 mmol), HOBt (13.6 mg, 0.09 mmol) and DIPEA (31.0 μL, 0.18 mmol) in a 0.5 mM solution of crude linear peptide (Intermediate 13b) (41 mg, 0.04 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as off-white powder (2.5 mg, 6% yield); $[\alpha]_D^{22}$=+80.0° (c=0.30, MeOH);
$^1$H-NMR (400 MHz, DMSO-d$_6$): δ=0.85 (d, J=7 Hz, 3H, 6-CH$_3$), 2.87 (m, 1H, 3-CH$_A$H$_B$), 3.15 (s, 3H, 8-CH$_3$), 3.20 (m, 1H, 3-CH$_A$H$_B$), 3.24 (m, 1H, 8-CH$_A$H$_B$), 3.27 (m, 1H, 3-CH$_A$H$_B$), 3.40 (s, 3H, 1-CH$_3$), 3.51 (dd, J=14, 3 Hz, 1H, 8-CH$_A$H$_B$), 3.64 (m, 2H, 3 and 4-CH$_A$H$_B$), 3.75 (dd, J=9, 7 Hz, 1H, 1-CH$_A$H$_B$), 3.86 (d, J=17 Hz, 1H, 5-CH$_A$H$_B$), 3.93 (dd, J=17, 7 Hz, 1H, 5-CH$_A$H$_B$), 4.33-4.42 (m, 3H, 1 and 6-α-CH and 1-CH$_A$H$_B$), 4.84 (m, 3-α-CH), 4.95 (s, 1H, 7-CH$_A$H$_B$), 5.18 (s, 1H, 7-CH$_A$H$_B$), 5.46 (m, 1H, 4-α-CH), 6.93-7.08 (m, 3H, Ar Hs), 7.25 (s, 2H, Ar H), 7.31 (d, J=8 Hz, 1H, Ar H), 7.43 (dd, J=8 Hz, 1H, Ar H), 7.85 (d, J=8 Hz, 1H, Ar H), 8.04 (s, 1H, 2-CH), 8.20 (d, J=9 Hz, 1H, 3-NH), 8.34 (d, J=9 Hz, 1H, 4-NH), 8.56 (d, J=9 Hz, 1H, 1-NH), 8.60 (m, 1H, 5-NH), 8.65 (m, 1H, 1-NH), 9.22 (s, 1H, 7-NH), 10.76 (d, J=2 Hz, 1H, indole-NH), 11.31 (d, J=2 Hz, 1H, indole-NH) ppm; MS: m/z (+ESI) calcd. for C$_{40}$H$_{44}$BrN$_{10}$O$_8$S$^+$903.2242, found 903.2218 [MH$^+$]; RP-HPLC Method 1, t$_R$ 9.12 min.

Cyclo[D-Ala-Thz-Trp-Trp(4-Cl)-Gly-D-Ala-Dha-Sar] (Compound 2)

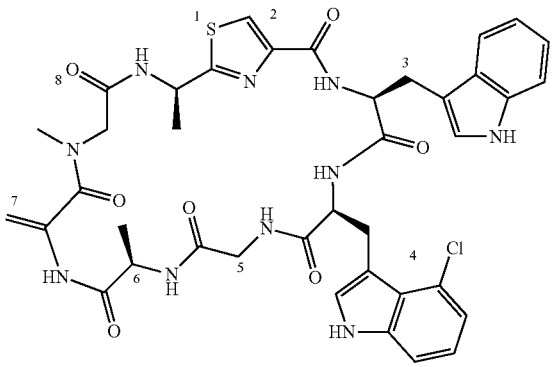 [SMILES: C=C1NC(=O)[C@@H](C)NC(=O)CNC(=O)[C@H](Cc2c[nH]c3cccc(Cl)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (0.098 g, 0.2 mmol), HOBt (0.03 g, 0.2 mmol) and DIPEA (66.2 μL, 0.4 mmol) in a 0.5 mM solution of crude linear peptide (Intermediate 13c) (0.08 g, 0.1 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (3.51 mg, 5% yield); $[\alpha]_D^{22}$=+87.9° (c=0.16, MeOH);
$^1$H-NMR (400 MHz, DMSO-d$_6$): δ=0.91 (d, J=7 Hz, 3H, 6-CH$_3$), 1.58 (d, J=7 Hz, 3H, 1-CH$_3$), 1.69 (m, m, 1H, 3-CH$_A$H$_B$), 1.77 (m, 1H, 8-CH$_A$H$_B$), 2.91 (m, 1H, 4-CH$_A$H$_B$), 3.05 (m, 1H, 5-CH$_A$H$_B$), 3.15 (s, 3H, 8-CH$_3$), 3.18 (m, 1H, 3-CH$_A$H$_B$), 3.25 (m, 2H, 8-CH$_A$H$_B$), 3.77 (m, 1H, 5-CH$_A$H$_B$), 3.89 (dd, J=17, 5 Hz, 1H, 4-CH$_A$H$_B$), 4.24 (m, 1H, 6-α-CH), 4.37 (dd, J=15, 8 Hz, 1H, 4-α-CH), 4.81

(m, 1H, 3-α-CH), 4.95 (s, 1H, 7-CH$_A$H$_B$), 5.20 (s, 1H, 7-CH$_A$H$_B$), 5.42 (m, 1H, 1-α-CH), 6.98 (t, J=8 Hz, 1H, Ar H), 7.07 (t, J=8 Hz, 1H, Ar H), 7.12 (m, 1H, Ar H), 7.21 (m, 1H, Ar H), 7.34 (m, 2H, Ar Hs), 7.41 (d, J=9 Hz, 1H, Ar H), 7.67 (m, 1H, Ar H), 7.79 (d, J=8 Hz, 1H, Ar H), 8.04 (s, 1H, 2-CH), 8.12 (d, J=9 Hz, 1H, 6-NH), 8.30 (d, J=9 Hz, 1H, 1-NH), 8.45 (s, 1H, 4-NH), 8.58 (d, J=8 Hz, 1H, 3-NH), 8.77 (t, J=6 Hz, 1H, 5-NH), 9.27 (s, 1H, 7-NH), 10.79 (s, 1H, indole-NH), 11.18 (s, 1H, indole-NH) ppm; MS: m/z (+ESI) calcd. for C$_{39}$H$_{42}$ClN$_{10}$O$_7$S$^+$829.2642, found 829.2551 [MH$^+$]; RP-HPLC Method 1, $t_R$ 7.81 min.

Cyclo[D-Ala-Thz-Trp-Trp(4-Br)-Gly-D-Ala-Dha-Sar] (Compound 3)

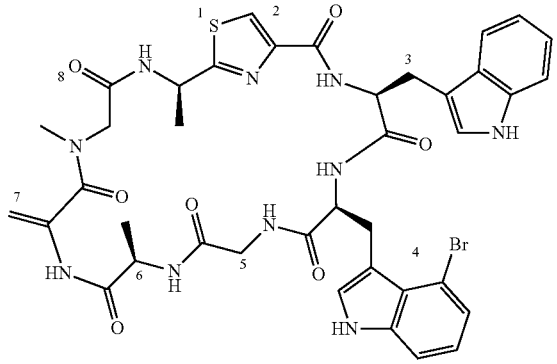 [SMILES: C=C1NC(=O)[C@@H](C)NC(=O)CNC(=O)[C@H](Cc2c[nH]c3cccc(Br)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (104 mg, 0.2 mmol), HOBt (30.6 mg, 0.2 mmol) and DIPEA (139 μL, 0.8 mmol) in a 0.5 mM solution of crude linear (Intermediate 13d) peptide (89 mg, 0.1 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (5.75 mg, 7% yield); [α]$_D^{22}$=+20.4° (c=0.18, MeOH);

$^1$H-NMR (400 MHz, DMSO-d$_6$): δ=1.11 (d, J=7 Hz, 3H, 6-CH$_3$), 1.58 (d, J=7 Hz, 3H, 1-CH$_3$), 3.32 (s, 3H, 8-CH$_3$), 3.42 (d, J=7 Hz, 1H, 3-CH$_A$H$_B$), 3.43 (d, J=7 Hz, 1H, 8-CH$_A$H$_B$), 3.49 (d, J=7 Hz, 1H, 4-CH$_A$H$_B$), 3.53 (m, 2H, 5-CH$_A$H$_B$ and 4-CH$_A$H$_B$), 3.58 (d, J=6 Hz, 1H, 3-CH$_A$H$_B$), 3.62 (m, 1H, 8-CH$_A$H$_B$), 3.67 (m, 1H, 5-CH$_A$H$_B$), 4.45 (m, 2H, 4 and 6-α-CH), 4.97 (s, 1H, 7-CH$_A$H$_B$), 5.10 (m, 1H, 3-α-CH), 5.27 (s, 1H, 7-CH$_A$H$_B$), 5.53 (m, 1H, 1-α-CH), 7.06 (m, 2H, Ar Hs), 7.13 (dt, J=8, 1 Hz, 1H, Ar H), 7.16 (d, J=2 Hz, 1H, Ar H), 7.28 (dd, J=8, 1 Hz, 2H, Ar Hs), 7.32 (m, 1H, Ar H), 7.36 (d, J=8 Hz, 1H, Ar H), 7.50 (dd, J=8 Hz, 1H, Ar H), 7.70 (m, 2H, 4- and 5-NH), 7.84 (d, J=8 Hz, 1H, 6-NH), 8.02 (s, 1H, 2-CH), 8.58 (d, J=9 Hz, 1H, 1-NH), 8.91 (d, J=8 Hz, 1H, 3-NH), 9.21 (s, 1H, 7-NH), 10.44 (s, 1H, indole-NH), 10.58 (s, 1H, indole-NH) ppm; MS: m/z (+ESI) calcd. for C$_{39}$H$_{42}$BrN$_{10}$O$_7$S$^+$873.2137, found 873.2138 [MH$^+$]; RP-HPLC Method 1, $t_R$ 9.13 min.

Cyclo[D-Ala-Thz-Trp-Trp(4-F)-Gly-D-Ala-Dha-Sar] (Compound 4)

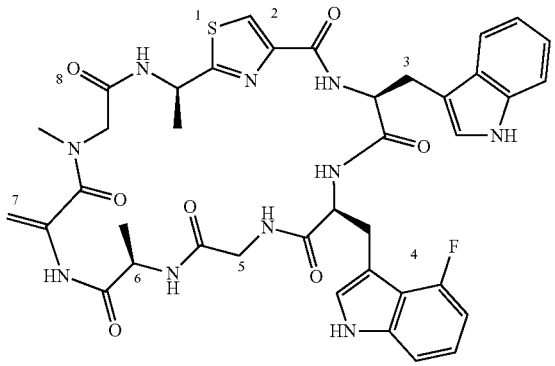 [SMILES: C=C1NC(=O)[C@@H](C)NC(=O)CNC(=O)[C@H](Cc2c[nH]c3cccc(F)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (88.5 mg, 0.17 mmol), HOBt (26 mg, 0.17 mmol) and DIPEA (119 μL, 0.68 mmol) in a 0.5 mM solution of crude linear peptide (Intermediate 13e) (70.9 mg, 0.09 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (0.91 mg, 2% yield); [α]$_D^{22}$=+32.0° (c=0.06, MeOH);

$^1$H-NMR (400 MHz, DMSO-d$_6$): δ=0.90 (d, J=7 Hz, 3H, 6-CH$_3$), 1.58 (d, J=7 Hz, 3H, 1-CH$_3$), 2.82 (d, J=4 Hz, 1H, 8-CH$_A$H$_B$), 2.89 (m, 1H, 4-CH$_A$H$_B$), 3.15 (s, 3H, 8-CH$_3$), 3.19 (m, 2H, 5-CH$_A$H$_B$), 3.25 (m, 1H, 4-CH$_A$H$_B$), 3.81 (m, 1H, 3-CH$_A$H$_B$), 3.88 (m, 2H, 3 and 8-CH$_A$H$_B$), 4.25 (dt, J=8, 3 Hz, 1H, 5-CH$_A$H$_B$), 4.37 (m, 2H, 4 and 6-α-CH), 4.48 (m, 1H, 3-α-CH), 4.95 (s, 1H, 7-CH$_A$H$_B$), 5.19 (s, 1H, 7-CH$_A$H$_B$), 5.43 (m, 1H, 1-α-CH), 6.92 (m, 1H, Ar H), 6.98 (dt, J=8, 1 Hz, 1H, Ar H), 7.16 (dt, J=8, 1 Hz, 1H, Ar H), 7.17 (dd, J=10, 2 Hz, 1H, Ar H), 7.21 (d, J=3 Hz, 1H, Ar H), 7.25 (d, J=3 Hz, 1H, Ar H), 7.31 (d, J=8 Hz, 1H, Ar H), 7.59 (dd, J=9, 6 Hz, 1H, Ar H), 7.79 (d, J=8 Hz, 1H, Ar H), 8.03 (s, 1H, 2-CH), 8.13 (d, J=9 Hz, 1H, 4-NH), 8.30 (d, J=9 Hz, 1H, 6-NH), 8.45 (d, J=3 Hz, 1H, 3-NH), 8.56 (d, J=9 Hz, 1H, 1-NH), 8.72 (t, J=6 Hz, 1H, 5-NH), 9.24 (s, 1H, 7-NH), 10.78 (d, J=2 Hz, 1H, indole-NH), 11.02 (d, J=2 Hz, 1H, indole-NH) ppm; MS: m/z (+ESI) calcd. for C$_{39}$H$_{42}$FN$_{10}$O$_7$S$^+$813.2937, found 813.3075 [MH$^+$]; RP-HPLC Method 1, $t_R$ 8.48 min.

Cyclo[D-Ala-Thz-Trp-Trp(4-CF$_3$)-Gly-D-Ala-Dha-Sar] (Compound 5)

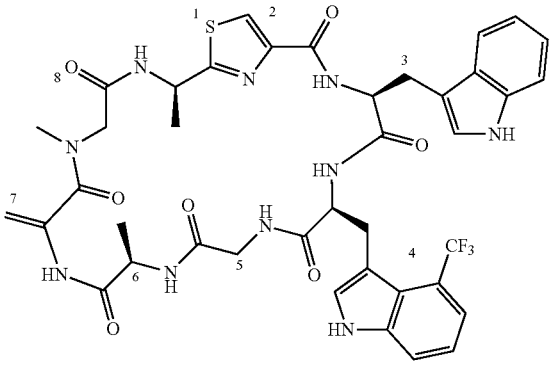 [SMILES: C=C1NC(=O)[C@@H](C)NC(=O)CNC(=O)[C@H](Cc2c[nH]c3cccc(C(F)(F)F)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (104 mg, 0.2 mmol), HOBt (30.6 mg, 0.2 mmol) and DIPEA (139 µL, 0.8 mmol) in a 0.5 mM solution of crude linear peptide (Intermediate 13o (86 mg, 0.1 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (5 mg, 6% yield); $[\alpha]_D^{22}$=+ 105.1° (c=0.59, MeOH);

$^1$H-NMR (400 MHz, DMSO-d$_6$): δ=0.92 (d, J=7 Hz, 3H, 6-CH$_3$), 1.58 (d, J=7 Hz, 3H, 1-CH$_3$), 3.14 (s, 3H, 8-CH$_3$), 3.21 (m, 2H, 3 and 8-CH$_A$H$_B$), 3.26 (m, 1H, 4-CH$_A$H$_B$), 3.35 (dd, J=16, 6 Hz, 1H, 5-CH$_A$H$_B$), 3.42 (dd, J=18, 5 Hz, 1H, 4-CH$_A$H$_B$), 3.49 (d, J=14 Hz, 1H, 3-CH$_A$H$_B$), 3.83 (d, J=17 Hz 1H, 8-CH$_A$H$_B$), 4.06 (dd, J=17, 7 Hz, 1H, 5-CH$_A$H$_B$), 4.32 (m, 1H, 6-α-CH), 4.39 (t, J=8 Hz, 1H, 4-α-CH), 4.86 (t, J=9 Hz, 1H, 3-α-CH), 4.94 (s, 1H, 7-CH$_A$H$_B$), 5.18 (s, 1H, 7-CH$_A$H$_B$), 5.43 (m, 1H, 1-α-CH), 6.97 (t, J=8 Hz, 1H, Ar H), 7.05 (t, J=8 Hz, 1H, Ar H), 7.21 (m, 1H, Ar H), 7.26-7.30 (m, 2H, Ar Hs), 7.49 (d, J=8 Hz, 1H, Ar H), 7.76 (d, J=8 Hz, 1H, Ar H), 7.82 (d, J=8 Hz, 1H, Ar H), 8.04 (s, 1H, 2-CH), 8.21 (d, J=9 Hz, 1H, 4-NH), 8.30 (d, J=9 Hz, 1H, 6-NH), 8.54 (d, J=9 Hz, 1H, 3-NH), 8.64 (t, J=5 Hz, 1H, 5-NH), 8.80 (s, 1H, 1-NH), 9.27 (s, 1H, 7-NH), 10.74 (s, 1H, indole-NH), 11.64 (s, 1H, indole-NH) ppm; MS: m/z (+ESI) calcd. for C$_{40}$H$_{42}$F$_3$N$_{10}$O$_7$S$^+$863.2905, found 862.9756 [MH$^+$]; RP-HPLC Method 1, t$_R$ 9.22 min.

Cyclo[D-Ala-Thz-Trp-Trp(4,5-Cl)-Gly-D-Ala-Dha-Sar] (Compound 6)

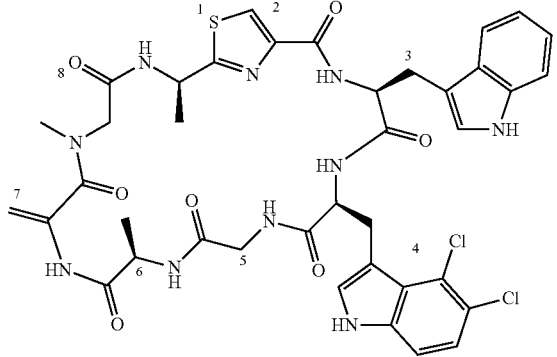 [SMILES: C=C1NC(=O)[C@@H](C)NC(=O)CNC(=O)[C@H](Cc2c[nH]c3ccc(Cl)c(Cl)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (78 mg, 0.15 mmol), HOBt (23 mg, 0.15 mmol) and DIPEA (104 µL, 0.58 mmol) in a 0.5 mM solution of crude linear peptide (Intermediate 13 h) (65 mg, 0.074 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as yellow powder (1.28 mg, 2% yield); $[\alpha]_D^{22}$=+71.3° (c=0.16, MeOH);

$^1$H-NMR (400 MHz, DMSO-d$_6$): δ=0.88 (d, J=7 Hz, 3H, 6-CH$_3$), 1.58 (d, J=7 Hz, 3H, 1-CH$_3$), 3.01 (m, 1H, 3-CH$_A$H$_B$), 3.10 (m, 1H, 8-CH$_A$H$_B$), 3.17 (s, 3H, 8-CH$_3$), 3.27 (m, 1H, 4-CH$_A$H$_B$), 3.49 (m, 1H, 5-CH$_A$H$_B$), 3.60 (dd, J=15, 5 Hz, 1H, 4-CH$_A$H$_B$), 3.67 (m, 1H, 3-CH$_A$H$_B$), 3.83 (m, 1H, 8-CH$_A$H$_B$), 3.94 (dd, J=16, 8 Hz, 1H, 5-CH$_A$H$_B$), 4.35 (m, 2H, 4 and 6-α-CH), 4.83 (t, J=9 Hz, 1H, 3-α-CH), 4.96 (s, 1H, 7-CH$_A$H$_B$), 5.18 (s, 1H, 7-CH$_A$H$_B$), 5.43 (m, 1H, 1-α-CH), 6.57 (s, 1H, Ar H), 7.00 (m, 1H, Ar H), 7.06 (t, J=8 Hz, 1H, Ar H), 7.14 (m, 1H, Ar H), 7.23 (m, 1H, Ar H), 7.28-7.31 (m, 3H, Ar Hs), 7.41 (d, J=8 Hz, 1H, Ar H), 7.86 (d, J=9 Hz, 1H, 4-NH), 8.03 (s, 1H, 2-CH), 8.19 (d, J=9 Hz, 1H, 6-NH), 8.30 (d, J=9 Hz, 1H, 3-NH), 8.65 (m, 1H, 1 and 5-NH), 9.20 (s, 1H, 7-NH), 10.77 (s, 1H, indole-NH), 11.47 (s, 1H, indole-NH) ppm; MS: m/z (+ESI) calcd. for C$_{39}$H$_{41}$Cl$_2$N$_{10}$O$_7$S$^+$863.2252, found 863.2236 [MH$^+$]; RP-HPLC Method 1, t$_R$ 9.86 min.

Cyclo[D-Ala-Thz-Trp-Trp(4-Cl)-Gly-D-Ala-Thr-Sar] (Compound 7)

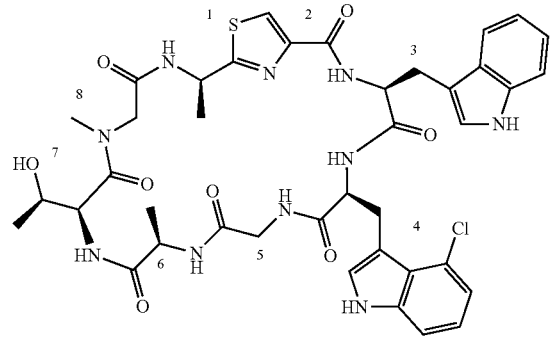 [SMILES: C[C@H]1NC(=O)CNC(=O)[C@H](Cc2c[nH]c3cccc(Cl)c23)NC(=O)[C@H](Cc2c[nH]c3ccccc23)NC(=O)c2csc(n2)[C@@H](C)NC(=O)CN(C)C(=O)[C@H]([C@@H](C)O)NC1=O]

Synthesis was carried out using the general procedure for head-to-tail cyclisation employing PyBOP (104 mg, 0.2 mmol), HOBt (30.6 mg, 0.2 mmol) and DIPEA (139 µL, 0.8 mmol) in a 0.5 mM solution of crude linear peptide (Intermediate 13m) (114 mg, 0.1 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (11.8 mg, 14% yield); $[\alpha]_D^{22}$=+62.2° (c=0.11, MeOH);

$^1$H-NMR (400 MHz, DMSO-d$_6$): δ=0.70 (d, J=7 Hz, 3H, 6-CH$_3$), 1.28 (d, J=7 Hz, 3H, 1-CH$_3$), 1.62 (d, J=7 Hz, 3H, 7-CH$_3$), 3.20 (dd, J=14, 9 Hz, 2H, 3 and 5-CH$_A$H$_B$), 3.30 (d, J=17, 6 Hz, 1H, 8-CH$_A$H$_B$), 3.43 (s, 3H, 8-CH$_3$), 3.52 (t, J=14 Hz, 1H, 4-CH$_A$H$_B$), 3.62 (m, 1H, 5-CH$_A$H$_B$), 3.66 (m, 1H, 4-CH$_A$H$_B$), 3.71 (dd, J=14, 5 Hz, 1H, 3-CH$_A$H$_B$), 3.79 (dd, J=17, 7 Hz, 1H, 8-CH$_A$H$_B$), 4.03 ((m, 1H, 4-α-CH), 4.18 (m, 1H, 6-α-CH), 4.35 (m, 1H, 7-CH), 4.6 (d, J=7 Hz, 1H, 7-α-CH), 4.85 (dt, J=4, 11 Hz, 1H, 3-α-CH), 5.38 (m, 1H, 1-α-CH), 6.98-7.06 (m, 2H, Ar Hs), 7.07-7.13 (m, 2H, Ar Hs), 7.17 (d, J=3 Hz, 1H, Ar H), 7.22 (d, J=3 Hz, 1H, Ar H), 7.26 (d, J=3 Hz, 1H, Ar H), 7.31 (d, J=8 Hz, 2H, Ar H), 7.39 (dd, J=6, 3 Hz, 1H, Ar H), 7.67 (d, J=9 Hz, 1H, 4-NH), 7.94 (d, J=8 Hz, 1H, 3-NH), 7.99 (s, 1H, 2-CH), 8.27 (d, J=9 Hz, 1H, 6-NH), 8.65 (s, 1H, 7-NH), 8.71 (d, J=10 Hz, 1H, 1-NH), 8.83 (t, J=6 Hz, 1H, 5-NH), 10.82 (d, J=2 Hz, 1H, indole-NH), 11.31 (d, J=2 Hz, 1H, indole-NH) ppm; MS: m/z (+ESI) calcd. for C$_{40}$H$_{46}$ClN$_{10}$O$_8$S$^+$861.2904, found 860.9862 [MH$^+$]; RP-HPLC Method 1, t$_R$ 8.60 min.

Cyclo[D-Ser-Thz-Trp-Trp(4-Cl)-Gly-D-Ala-Dha-Sar]
(Compound 8)

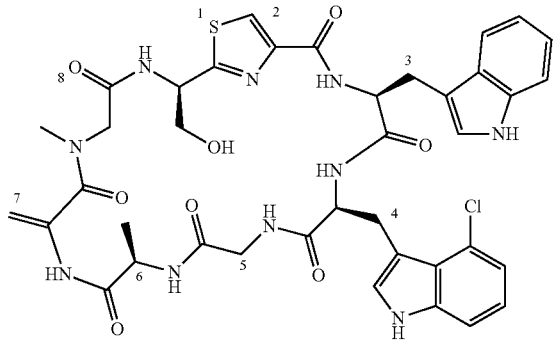 [SMILES: C=C1NC(=O)[C@@H](C)NC(=O)CNC(=O)[C@H](Cc2c[nH]c3cccc(Cl)c23)NC(=O)[C@H](Cc2c[nH]c3ccccc23)NC(=O)c2csc(n2)[C@@H](CO)NC(=O)CN(C)C1=O]

Synthesis was carried out using the general procedure for head-to-tail cyclisation employing PyBOP (104 mg, 0.2 mmol), HOBt (30.6 mg, 0.2 mmol) and DIPEA (139 µL, 0.8 mmol) in a 0.5 mM solution of crude linear peptide (Intermediate 13i) (86 mg, 0.1 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (2.98 mg, 4% yield); $[\alpha]_D^{22}$=+87.84° (c=0.64, MeOH);
$^1$H-NMR (400 MHz, DMSO-d$_6$): δ=0.84 (d, J=7 Hz, 3H, 6-CH$_3$), 3.05 (m, 1H, 3-CH$_A$H$_B$), 3.16 (s, 3H, 8-CH$_3$), 3.25 (m, 1H, 3-CH$_A$H$_B$), 3.28 (m, 1H, 8-CH$_A$H$_B$), 3.37 (m, 1H, 4-CH$_A$H$_B$), 3.40 (m, 1H, 5-CH$_A$H$_B$), 3.68 (m, 1H, 4-CH$_A$H$_B$), 3.77 (m, 2H, 1 and 3-CH$_A$H$_B$), 3.81 (d, J=5 Hz, 1H, 8-CH$_A$H$_B$), 3.86 (m, 1H, 5-CH$_A$H$_B$), 3.93 (dd, J=17, 7 Hz, 1H, 1-CH$_A$H$_B$), 4.34 (m, 2H, 4 and 6-α-CH), 4.84 (dt, J=10, 3 Hz, 1H, 3-α-CH), 4.95 (s, 1H, 7-CH$_A$H$_B$), 5.18 (s, 1H, 7-CH$_A$H$_B$), 5.27 (m, 1H, 1-α-CH), 6.99 (dt, J=8, 1 Hz, 1H, Ar H), 7.04-7.12 (m, 3H, Ar Hs), 7.24 (m, 2H, Ar H), 7.31 (d, J=8 Hz, 1H, Ar H), 7.38 (dd, J=7, 2 Hz, 1H, Ar H), 7.85 (d, J=5 Hz, 1H, Ar H), 8.01 (s, 1H, 2-CH), 8.11 (d, J=9 Hz, 1H, 4-NH), 8.21 (d, J=9 Hz, 1H, 6-NH), 8.27 (d, J=9 Hz, 1H, 1-NH), 8.58 (d, J=9 Hz, 1H, 3-NH), 8.65 (m, 1H, 5-NH), 9.20 (s, 1H, 7-NH), 10.76 (d, J=2 Hz, 1H, indole-NH), 11.30 (d, J=2 Hz, 1H, indole-NH) ppm; MS: m/z (+ESI) calcd. for C$_{39}$H$_{42}$ClN$_{10}$O$_8$S$^+$845.2591, found 844.9545 [MH$^+$]; RP-HPLC Method 1, t$_R$ 8.14 min.

Cyclo[D-Ala-Thz-Trp-Trp(4-Cl)-Gly-D-Ala-Dhb-Sar]
(Compound 9)

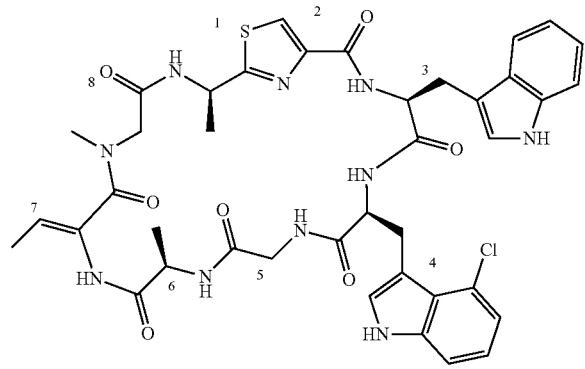 [SMILES: C/C=C1\NC(=O)[C@@H](C)NC(=O)CNC(=O)[C@H](Cc2c[nH]c3cccc(Cl)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (12 mg, 0.02 mmol), HOBt (3 mg, 0.02 mmol) and DIPEA (17.5 µL, 0.10 mmol) in a 0.5 mM solution of crude linear peptide (Intermediate 13n) (10 mg, 0.01 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (0.5 mg, 5% yield); $[\alpha]_D^{22}$=+181.82° (c=0.088, MeOH);
$^1$H-NMR (400 MHz, DMSO-d$_6$): δ=0.81 (d, J=7 Hz, 3H, 6-CH$_3$), 1.56 (d, J=7 Hz, 3H, 1-CH$_3$), 1.80 (d, J=7 Hz, 3H, 7-CH$_3$), 3.20 (s, 3H, 8-CH$_3$), 3.53-3.75 (m, 7H, 3-CH$_2$, 4-CH$_2$, 5-CH$_A$H$_B$, 8-CH$_2$), 4.25 (m, 1H, 6-α-CH), 4.33 (m, 2H, 3-α-CH, 5-CH$_A$H$_B$), 4.78 (m, 1H, 4-α-CH), 5.41 (m, 1H, 1-α-CH), 5.54 (q, J=11, 6 Hz, 1H, 7-CH), 6.99-7.11, 7.20-7.28 (m, 7H, Ar Hs), 7.36 (dd, J=7, 2 Hz, 1H, Ar H), 7.86 (d, J=7 Hz, 1H, Ar H), 7.96 (s, 1H, 2-CH), 8.04 (d, J=9 Hz, 1H, 1-NH), 8.18 (d, J=9 Hz, 1H, 6-NH), 8.46 (m, 1H, 3-NH), 8.58 (s, 1H, 7-NH), 8.73 (m, 2H, 4-NH, 5-NH), 10.75 (s, 1H, indole-NH), 11.27 (s, 1H, indole-NH) ppm; MS: m/z (+ESI) calcd. for C$_{40}$H$_{44}$ClN$_{10}$O$_7$S$^+$843.2798 and 845.2769, found 843.2839 and 845.2850 [MH$^+$]; and calcd. for C$_{40}$H$_{43}$ClN$_{10}$NaO$_7$S$^+$865.2623 and 867.2594, found 865.2650 and 867.2658 [MNa$^+$]; RP-HPLC Method 1, t$_R$ 9.55 min.

Cyclo[D-Ala-Thz-Trp-Trp(4-Br)-Gly-D-Ala-Dhb-Sar]
(Compound 10)

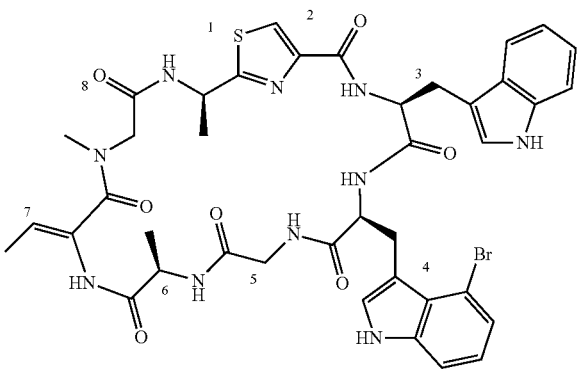 [SMILES: C/C=C1\NC(=O)[C@@H](C)NC(=O)CNC(=O)[C@H](Cc2c[nH]c3cccc(Br)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (26 mg, 0.05 mmol), HOBt (6.8 mg, 0.05 mmol) and DIPEA (38 µL, 0.225 mmol) in a 0.5 mM solution of crude linear peptide (Intermediate 13o) (22.6 mg, 0.025 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (7.76 mg, 35% yield); $[\alpha]_D^{22}$=+131.96 (c=0.97, MeOH);
$^1$H-NMR (400 MHz, DMSO-d$_6$): δ=0.79 (d, J=7 Hz, 3H, 6-CH$_3$), 1.54 (d, J=7 Hz, 3H, 1-CH$_3$), 1.78 (d, J=7 Hz, 3H, 7-CH$_3$), 3.19 (s, 3H, 8-CH$_3$), 3.25-3.79 (m, 7H, 3-CH$_2$, 4-CH$_2$, 5-CH$_A$H$_B$, 8-CH$_2$), 4.23 (m, 1H, 6-α-CH), 4.32 (m, 2H, 3-α-CH, 5-CH$_A$H$_B$), 4.77 (td, J=12, 3 Hz, 1H, 4-α-CH), 5.38 (m, 1H, 1-α-CH), 5.53 (q, J=14, 7 Hz, 1H, 7-CH), 6.92-7.03, 7.20-7.27 (m, 7H, Ar Hs), 7.38 (d, J=8 Hz, 1H, Ar H), 7.83 (d, J=7 Hz, 1H, Ar H), 7.95 (s, 1H, 2-CH), 8.01 (d, J=9 Hz, 1H, 1-NH), 8.15 (d, J=9 Hz, 1H, 6-NH), 8.46 (m, 1H, 3-NH), 8.55 (s, 1H, 7-NH), 8.69 (m, 2H, 4-NH, 5-NH), 10.73 (s, 1H, indole-NH), 11.25 (d, J=2 Hz, 1H, indole-NH) ppm; MS: m/z (+ESI) calcd. for $C_{40}H_{44}BrN_{10}O_7S^+$ 887.2293 and 889.2273, found 887.2287 and 889.2263 [MH$^+$]; RP-HPLC Method 1, $t_R$ 9.87 min.

Cyclo[D-Ser(OMe)-Thz-Trp-Trp(4-Br)-Gly-D-Ala-Dhb-Sar] (Compound 11)

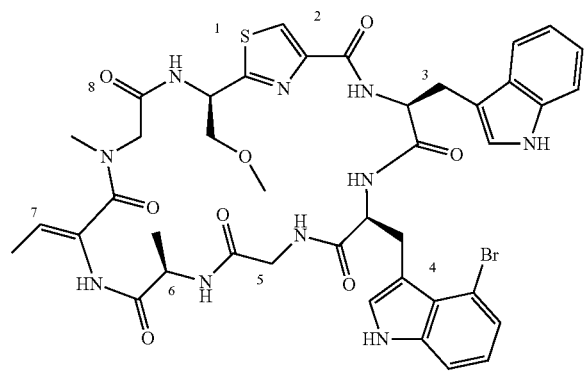 [SMILES: C/C=C1\NC(=O)[C@@H](C)NC(=O)CNC(=O)[C@H](Cc2c[nH]c3cccc(Br)c23)NC(=O)[C@H](Cc2c[nH]c3ccccc23)NC(=O)c2csc(n2)[C@@H](COC)NC(=O)CN(C)C1=O]

Synthesis was carried out using the general procedure for head-to-tail cyclisation employing PyBOP (22.3 mg, 0.04 mmol), HOBt (5.8 mg, 0.04 mmol) and DIPEA (32.8 µL, 0.193 mmol) in a 0.5 mM solution of crude linear peptide (Intermediate 13p) (43 mg, 0.02 mmol). The crude mixture was concentrated under vacuo and purified using semi-preparative RP-HPLC (Onyx Monolithic-C18 semi-preparative column (100×10 mm) at 9 mL min$^{-1}$) and freeze dried to afford the title peptide as white powder (3.69 mg, 19% yield); $[\alpha]_D^{22}$=+103.48 (c=0.1675, MeOH);
$^1$H-NMR (400 MHz, DMSO-d$_6$): δ=0.77 (d, J=7 Hz, 3H, 6-CH$_3$), 1.78 (d, J=7 Hz, 3H, 7-CH$_3$), 3.18 (s, 3H, 8-CH$_3$), 3.22-3.82 (m, 12H, 1-CH$_2$, 1-CH$_3$, 3-CH$_2$, 4-CH$_2$, 5-CH$_A$H$_B$, 8-CH$_2$), 4.26 (m, 1H, 6-α-CH), 4.36 (m, 1H, 5-CH$_A$H$_B$), 4.43 (m, 1H, 3-α-CH), 4.77 (m, 1H, 4-α-CH), 5.39 (m, 1H, 1-α-CH), 5.52 (q, J=14, 7 Hz, 1H, 7-CH), 6.94-7.05, 7.20-7.28 (m, 7H, Ar Hs), 7.40 (d, J=8 Hz, 1H, Ar H), 7.86 (d, J=7 Hz, 1H, Ar H), 7.98 (s, 1H, 2-CH), 8.08 (d, J=9 Hz, 1H, 1-NH), 8.18 (d, J=7 Hz, 1H, 6-NH), 8.51 (m, 1H, 3-NH), 8.60 (s, 1H, 7-NH), 8.65-8.74 (m, 2H, 4-NH, 5-NH), 10.74 (s, 1H, indole-NH), 11.28 (s, 1H, indole-NH) ppm; MS: m/z (+ESI) calcd. for $C_{40}H_{44}BrN_{10}O_7S^+$ 917.2399, found 917.2375 [MH$^+$]; RP-HPLC Method 1, $t_R$ 9.50 min.

Cyclo[D-Ala-Thz-Trp-Trp(4-Br)-Gly-D-Ala-Dhp-Sar] (Compound 12)

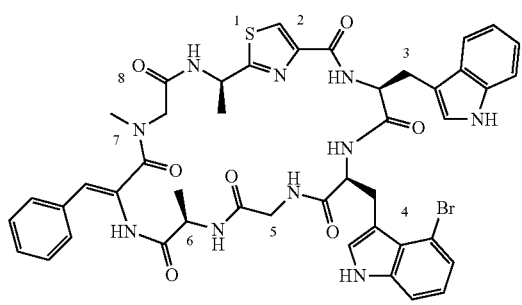 [SMILES: C[C@H]1NC(=O)CNC(=O)[C@H](Cc2c[nH]c3cccc(Br)c23)NC(=O)[C@H](Cc2c[nH]c3ccccc23)NC(=O)c2csc(n2)[C@@H](C)NC(=O)CN(C)C(=O)/C(=C/c2ccccc2)NC1=O]

Synthesis was carried out using the general procedure for head-to-tail cyclisation employing PyBOP (26 mg, 0.05 mmol), HOBt (6.8 mg, 0.05 mmol) and DIPEA (38 µL, 0.225 mmol) in a 0.5 mM solution of crude linear peptide (Intermediate 13q) (22.6 mg). The crude mixture was concentrated under vacuo and purified using preparative RP-HPLC (Onyx monolithic-C18 semi-preparative column (100×10 mm) at 9 mL min$^{-1}$) and freeze dried to afford the title peptide as a white powder (7.1 mg, 35% yield); $[\alpha]_D^{22}$=+144.1° (c=0.1, MeOH);
$^1$H-NMR (400 MHz, DMSO-d$_6$): δ=0.77 (d, J=7 Hz, 3H, 6-CH$_3$), 1.51 (d, J=7 Hz, 3H, 1-CH$_3$), 1.79 (d, J=7 Hz, 3H, 7-CH$_3$), 3.16 (s, 3H, 8-CH$_3$), 3.21-3.71 (m, 7H, 3-CH$_2$, 4-CH$_2$, 5-CH$_A$H$_B$, 8-CH$_2$), 4.22 (m, 1H, 6-α-CH), 4.31 (m, 2H, 3-α-CH, 5-CH$_A$H$_B$), 4.75 (td, J=12, 3 Hz, 1H, 4-α-CH), 5.31 (m, 1H, 1-α-CH), 5.86 (s, 1H, 7-CH), 6.92-7.03, 7.20-7.27 (m, 8H, Ar Hs), 7.38 (m, 3H, Ar H), 7.85 (m, 2H, Ar H), 7.97 (m, 2H, 2-CH), 8.11 (d, J=8 Hz, 1H, 1-NH), 8.18 (d, J=8 Hz, 1H, 6-NH), 8.44 (m, 1H, 3-NH), 8.51 (s, 1H, 7-NH), 8.68 (m, 2H, 4-NH, 5-NH), 10.79 (s, 1H, indole-NH), 11.01 (d, J=2 Hz, 1H, indole-NH) ppm; MS: m/z (+ESI) calcd. for $C_{45}H_{46}BrN_{10}O_7S^+$ 949.2450, found 949.2402 [MH$^+$]; RP-HPLC Method 1, $t_R$ 10.90 min.

Cyclo[D-Ala-Thz-Trp-Trp(4-Br)-Gly-D-Ala-Dhv-Sar] (Compound 13)

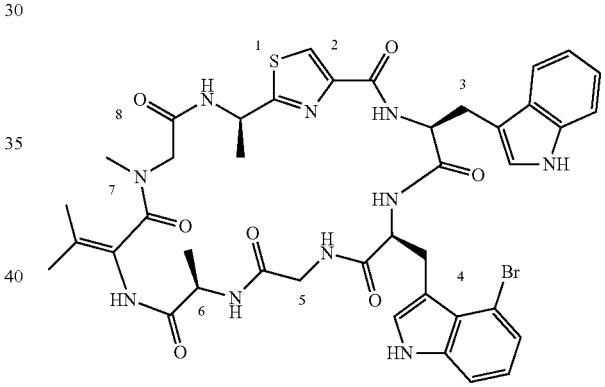

Synthesis was carried out using the general procedure for head-to-tail cyclisation employing PyBOP (26 mg, 0.05 mmol), HOBt (6.8 mg, 0.05 mmol) and DIPEA (38 µL, 0.225 mmol) in a 0.5 mM solution of crude linear peptide (Intermediate 13r) (22.6 mg). The crude mixture was concentrated under vacuo and purified using preparative RP-HPLC (Onyx monolithic-C18 semi-preparative column (100×10 mm) at 9 mL min$^{-1}$) and freeze dried to afford the title peptide as white powder (9.1 mg, 42%); $[\alpha]_D^{22}$=+134.2° (c=0.1, MeOH);
$^1$H-NMR (400 MHz, DMSO-d$_6$): δ=0.78 (d, J=7 Hz, 3H, 6-CH$_3$), 1.55 (d, J=7 Hz, 3H, 1-CH$_3$), 1.70 (s, 3H, 1-CH$_3$), 1.80 (s, 3H, 1-CH$_3$), 3.22 (s, 3H, 8-CH$_3$), 3.26-3.79 (m, 7H, 3-CH$_2$, 4-CH$_2$, 5-CH$_A$H$_B$, 8-CH$_2$), 4.24 (m, 1H, 6-α-CH), 4.33 (m, 2H, 3-α-CH, 5-CH$_A$H$_B$), 4.80 (td, J=12, 3 Hz, 1H, 4-α-CH), 5.41 (m, 1H, 1-α-CH), 6.92-7.03, 7.21-7.28 (m, 7H, Ar Hs), 7.39 (d, J=8 Hz, 1H, Ar H), 7.84 (d, J=7 Hz, 1H, Ar H), 7.96 (s, 1H, 2-CH), 8.11 (d, J=9 Hz, 1H, 1-NH), 8.19 (d, J=9 Hz, 1H, 6-NH), 8.56 (m, 1H, 3-NH), 8.65 (s, 1H, 7-NH), 8.79 (m, 2H, 4-NH, 5-NH), 10.80 (s, 1H, indole-NH), 11.19 (d, J=2 Hz, 1H, indole-NH) ppm; MS: m/z (+ESI) calcd. for $C_{41}H_{46}BrN_{10}O_7S^+$ 901.2450, found 901.2435 [MH$^+$]; RP-HPLC Method 1, $t_R$ 10.09 min.

Cyclo[D-Ala-Thz-Trp-Trp(4-Br)-Gly-D-Ala-Dhl-Sar] (Compound 14)

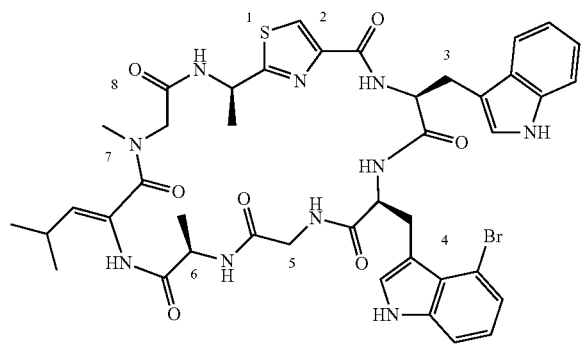 [SMILES: CC(C)/C=C1\NC(=O)[C@@H](C)NC(=O)CNC(=O)[C@H](Cc2c[nH]c3cccc(Br)c23)NC(=O)[C@H](Cc2c[nH]c3ccccc23)NC(=O)c2csc(n2)[C@@H](C)NC(=O)CN(C)C1=O]

Synthesis was carried out using the general procedure for head-to-tail cyclisation employing PyBOP (26 mg, 0.05 mmol), HOBt (6.8 mg, 0.05 mmol) and DIPEA (38 µL, 0.225 mmol) in a 0.5 mM solution of crude linear peptide (Intermediate 13s) (22.6 mg). The crude mixture was concentrated under vacuo and purified using preparative RP-HPLC (Onyx monolithic-C18 semi-preparative column (100×10 mm) at 9 mL min$^{-1}$) and freeze dried to afford the title peptide as white powder (6.3 mg, 35% yield); $[\alpha]_D^{22}$=+136.1° (c=0.1, MeOH)

$^1$H-NMR (400 MHz, DMSO-d$_6$): δ=0.84 (d, J=7 Hz, 3H, 6-CH$_3$), 1.04 (d, J=6 Hz, 3H, 7-CH$_3$), 1.15 (d, J=6 Hz, 3H, 7-CH$_3$), 1.58 (d, J=7 Hz, 3H, 1-CH$_3$), 2.34 (m, 1H, 7-CH), 3.30 (s, 3H, 8-CH$_3$), 3.25-3.80 (m, 7H, 3-CH$_2$, 4-CH$_2$, 5-CH$_A$H$_B$, 8-CH$_2$), 4.22 (m, 1H, 6-α-CH), 4.42 (m, 2H, 3-α-CH, 5-CH$_A$H$_B$), 4.78 (td, J=12, 3 Hz, 1H, 4-α-CH), 5.29 (m, 1H, 1-α-CH), 5.45 (q, J=14, 7 Hz, 1H, 7-CH), 6.97-7.09, 7.23-730 (m, 7H, Ar Hs), 7.40 (d, J=8 Hz, 1H, Ar H), 7.90 (d, J=7 Hz, 1H, Ar H), 7.96 (s, 1H, 2-CH), 8.06 (d, J=8 Hz, 1H, 1-NH), 8.19 (d, J=8 Hz, 1H, 6-NH), 8.41 (m, 1H, 3-NH), 8.50 (s, 1H, 7-NH), 8.61 (m, 2H, 4-NH, 5-NH), 10.78 (s, 1H, indole-NH), 11.28 (s, 1H, indole-NH) ppm; MS: m/z (+ESI) calcd. for $C_{42}H_{48}BrN_{10}O_7S^+$ 915.2606, found 915.2622 [MH$^+$]; RP-HPLC Method 1, $t_R$ 11.30 min.

Biological Data
Bacterial Susceptibility Assay Procedure

The bacterial susceptibility assay was carried out using a sensitive method that generates an overnight bacterial growth curve using periodic turbidometric measurements. The measurement is based on the fact that the bacterial culture becomes increasingly turbid as the number of cells in the solution increases. Light that passes through the bacterial culture is scattered by the bacteria, and therefore, turbidity is directly proportional to the number of bacteria in the solution. Bacteria contain numerous macromolecules that absorb light, for example proteins absorb light at 280 nm and DNA at 260 nm; however, at 610 nm the absorption is minimum and directly proportionate to the number of bacteria. The present study employed a Tecan microplate reader that measures the turbidity at 610 nm, and enables long-term kinetic studies inside the microplate reader under controlled temperature and without interruptive manipulations (such as transferring the plate between reader and incubator). This allows for the generation of data for an overnight growth study without any gaps.

The bacterial strains used in the antibacterial screening assay are *Pseudomonas aeruginosa* PAO1, *Burkholderia multivorans* ATCC17616, *B. cepasia* ATCC25416, *B. vietnamiensis* J2863, *Clostridium difficile* 630Δerm, *Streptococcus pyogene* and *Streptococcus agalactiae*. All strains were stored at −80° C. on arrival and have been maintained as frozen stocks ever since. *P. aeruginosa* culture was grown in Muller-Hinton (MH) media, aerobically, at 37° C. in a shaking incubator (200 rpm) overnight. *B. multivorans* culture was grown in MH media aerobically, at 30° C. in a shaking incubator (200 rpm) overnight. *Strep. pyogene* and *Strep. agalactiae* cultures were grown in brain heart infusion (BHI) media, aerobically, at 37° C. in a static incubator overnight. *C. difficile* culture was grown in supplemented brain heart infusion medium (BHIS), anaerobically, in an anaerobic workstation (Don Whitley, Yorkshire, UK) with the atmospheric condition of $CO_2:H_2:N_2$ (80:10:10 vol:vol:vol) at 37° C. overnight.

IC$_{50}$ Determination of *P. aeruginosa*

The IC$_{50}$ of the test compounds against bacterial strains *P. aeruginosa* PAO1 was determined in MH media. Overnight bacterial culture was diluted with fresh media to give an OD$_{610\ nm}$ of 0.05. To prepare the test compound dilution, a volume of 10 µL of a 10 mM solution of the test compound in DMSO was added to a volume of 990 µL of the freshly prepared bacterial sample. This sample was then serially diluted with freshly prepared OD$_{610\ nm}$ 0.05 bacterial culture containing 1% DMSO.

A volume of 200 µL of the prepared samples containing bacterial culture and the desired concentration of each compound were dispensed into a 96-well microtiter plate and incubated at 37° C. in a Tecan i-control 1.9.17.0 microplate reader. The OD was measured intermittently at 15 min over 15 h. The IC$_{50}$ was determined by measurement of OD$_{610\ nm}$ at 13 h. Each compound was evaluated in duplicate at concentration range of 0-100 µM and each experiment was repeated at least three times.

IC$_{50}$ Determination of Strep. *Pyogene* and Strep. *Agalactiae*

The IC$_{50}$ of test compounds against strains of Strep. *pyogene* and Strep. *agalactiae* were determined in BHI media at 37° C. following the protocol described under *P. aeruginosa*. The MIC$_{50}$ was determined by measurement of OD$_{610\ nm}$ at 13 h. Each compound was evaluated in duplicate at concentration range of 0-100 µM and each experiment was repeated at least three times.

IC$_{50}$ Determination of *Burkholderia cepasia* Organisms

The IC$_{50}$ of test compounds against bacterial strain *B. multivorans* ATCC17616, *B. cepasia* ATCC25416 and *B. vietnamiensis* J2863 was determined in MH media at 30° C., by following the protocol described under *P. aeruginosa*. The IC$_{50}$ was determined by measurement of OD$_{610\ nm}$ at 25 h. Each compound was evaluated in duplicate at concentration range of 0-25 µM and each experiment was repeated at least three times.

IC$_{50}$ Determination of *C. difficile*

The IC$_{50}$ of test compounds against bacterial strain *Clostridium difficile* 630Δerm was determined in BHIS media. A 1:10 dilution of overnight bacterial culture was performed with fresh media containing 1% DMSO. A volume of 2.5 µL of a 10 mM solution of the test compound in DMSO and 7.5 µL of DMSO were added to a volume of 990 µL of the freshly prepared bacterial sample. This sample was then serially diluted with freshly prepared 1% DMSO containing bacterial culture.

A volume of 200 µL of the prepared dilutions containing bacterial culture and the desired concentration of each compound were then dispensed into a 96-well microtiter plate and incubated anaerobically at 37° C. in a microplate reader. The OD was measured intermittently at 1 h intervals over 25 h, with 5 sec of shaking prior to each measurement. The $IC_{50}$ was determined by measurement of $OD_{610\ nm}$ at 13

It is noteworthy that isolates W4 and W23 showed high level of resistance to the carbapenem antibiotic, meropenem, while the isolate W14 showed high level of resistance to the monobactam antibiotic, aztreonam.

TABLE 3

The antibiotic sensitivity of *P. aeruginosa* clinical strains and PAO1 (wild-type strain).

| P. aeruginosa strains | MIC of antibiotic (µM) | | | | | | |
|---|---|---|---|---|---|---|---|
| | Amikacin | Gentamicin | Tobramycin | Meropenem | Aztreonam | Ciprofloxacin | Colistin |
| W4 | 24 | 8 | 9 | >45 | 18 | 1.5 | 3 |
| W14 | 41 | 8 | 25 | 9 | >92 | 18 | >8 |
| W23 | <14 | <4 | <4 | >45 | <9 | <1.5 | 2 |
| W46 | <14 | <4 | <4 | 14 | <9 | <1.5 | 2 |
| PAO1 | <14 | <4 | <4 | >45 | <9 | <1.5 | 3 | h. Each compound was evaluated in duplicate at concentration range of 0.5 nM-5 µM and each experiment was repeated at least three times.

Antimicrobial Activity of Compounds of the Invention
Activity Against *P. aeruginosa*

Compounds 2, 3 and 10 were evaluated for antipseudomonal activity and compared with Argyrin A. The $IC_{50}$ and the % growth inhibition at 100 µM are reported in Table 2.

The antibacterial assay revealed an increase in activity with compounds 2, 3 and 10 over Argyrin A. This finding indicates a surprising and unexpected trend in the activity profile of the halogenated compounds according to the invention.

In addition, substitution of Dha with dehydroaminobutyric acid (Dhb) residue shows marked difference in the antibacterial activity profile. Unexpectedly, the Dhb and 4-Br-tryptophan containing analogue, compound 10 showed three-fold increase in activity in comparison to the Dha containing compound 3.

In contrast, substitution of the Dha with either dehydrophenylalanine (compound 12) or dehydroleucine residue (compound 14) resulted in a dramatic loss in activity, whist replacement with a dehydrovaline residue (compound 13) did not result in a notable change in activity in comparison to the Dha containing compound 3.

TABLE 2

The $IC_{50}$ and % growth inhibition of argyrin A and compounds 2, 3, 10, 12, 13 and 14 against *P. aeruginosa* PAO1 in MH media at 13 h.

| Compounds | $IC_{50}$ (µM) | % Growth inhibition at 100 µM |
|---|---|---|
| Argyrin A | 19.8 ± 1.6 | 82.6 ± 7.4 |
| Compound 2 | 16.8 ± 2.9 | 87.0 ± 1.0 |
| Compound 3 | 13.2 ± 3.2 | 85.7 ± 0.6 |
| Compound 10 | 3.7 ± 1.0 | 90.6 ± 1.3 |
| Compound 12 | >100 | 20.1 ± 5.4 |
| Compound 13 | 12.2 ± 0.2 | 85.1 ± 3.4 |
| Compound 14 | >100 | 40.1 ± 6.8 |

Activity Against *P. aeruginosa*

The antibacterial activity of compounds 2 and 3 were tested against clinical isolates and one wild-type strain of *P. aeruginosa* displaying varying antibiotic sensitivity.

In this regard, four clinical isolates of *P. aeruginosa* were obtained from the University of Nottingham. The isolates showed varying level of antibiotic susceptibility, as shown in Table 3.

The antibacterial activity of compounds 2 and 3 were tested against these clinical isolates and one wild-type strain of *P. aeruginosa*.

Despite some of the isolates showing antibiotic resistance, when the antibacterial activity of compounds 2 and 3 were tested against these clinical isolates and one wild-type strain of *P. aeruginosa*, all of the above isolates were equally susceptible to compounds 2 and 3.

Figure 1B:
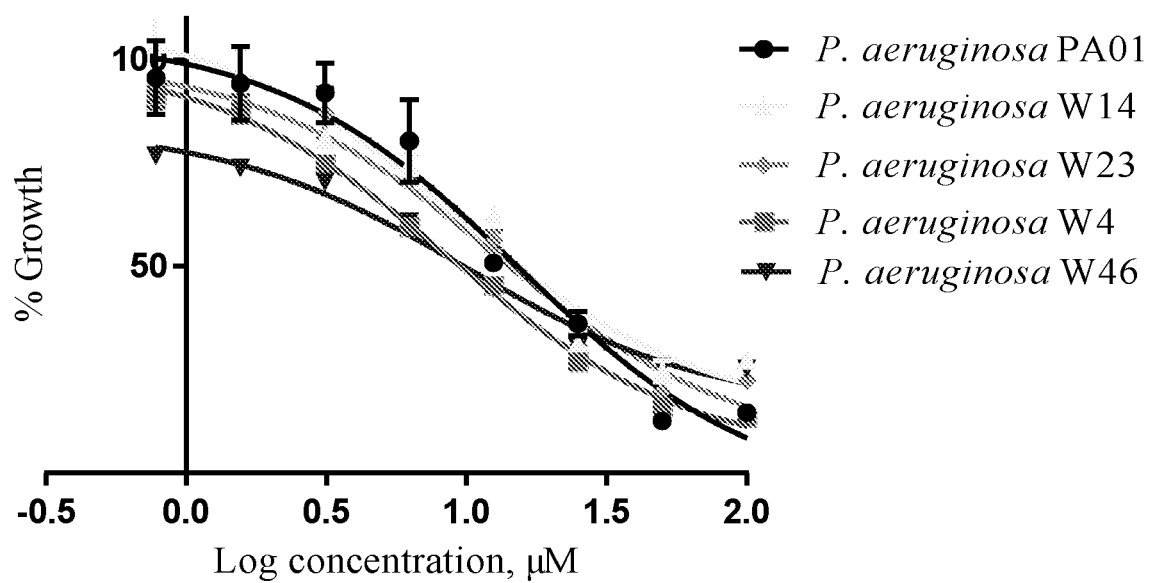

The results for Compound 2 are shown in FIG. 1A and the results for Compound 3 are shown in FIG. 1B. It can be seen that both compounds caused a significant decrease in growth for the *P. aeruginosa*.

Activity Against *Burkholderia multivorans*

The antimicrobial activity of compounds 2, 3 and 10 against *P. aeruginosa* and *Burkholderia multivorans* was investigated. Argyrin A was tested as a reference.

Figure 2A:
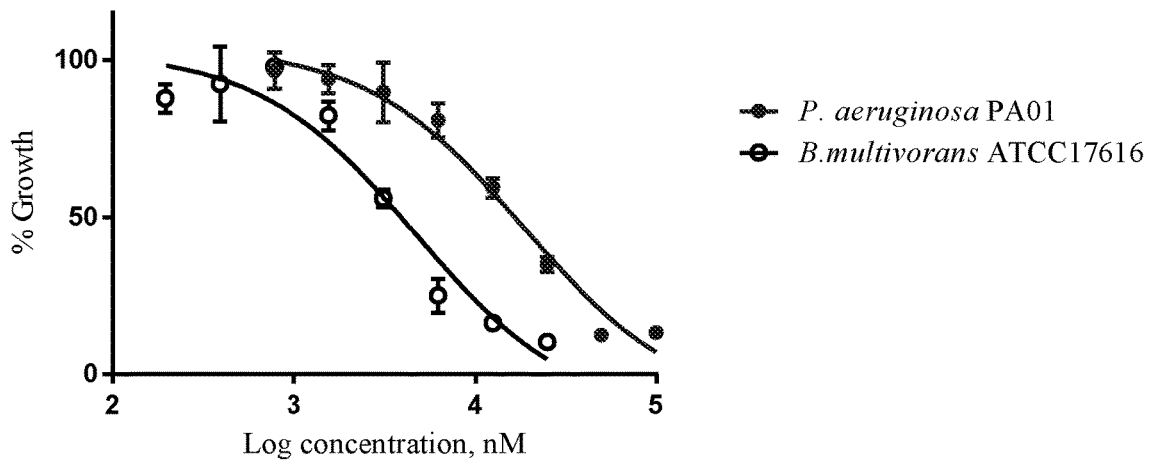
FIGS. 2a-c are graphs showing the effect of varying concentrations of compounds 2, 3 and 10 according to the invention on the growth of *B. multivorans* after 25 hours.
Figure 2B:
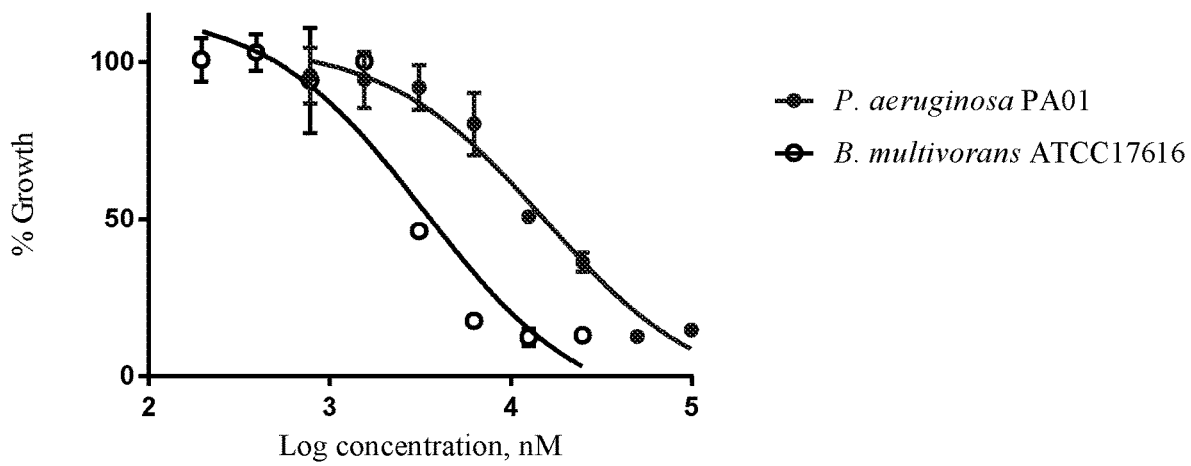
Figure 2C:
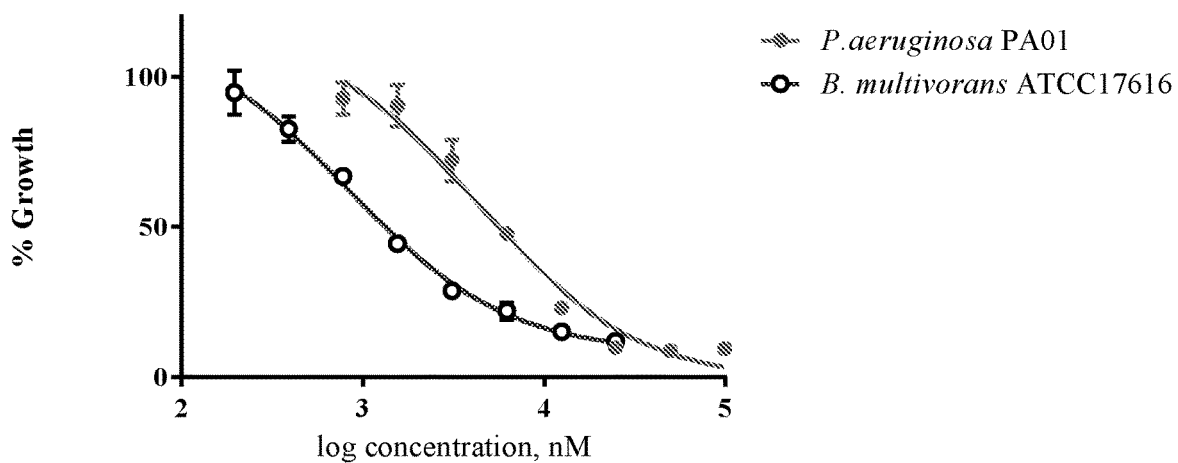

The results are shown in Table 4 and in FIGS. 2A-C. FIG. 2A shows the results for compound 2; FIG. 2B shows the results for compound 3; and FIG. 2C shows the results for compound 10.

TABLE 4

$IC_{50}$ values for argyrin A and compounds 2, 3 and 10 measured against *P. aeruginosa* at 13 h and *B. multivorans* at 25 h.

| Organisms | $IC_{50}$ (µM) | | | |
|---|---|---|---|---|
| | Compound 2 | Compound 3 | Compound 10 | Argyrin A |
| *P. aeruginosa* PAO1 | 16.8 ± 2.9 | 13.2 ± 3.2 | 3.7 ± 1.0 | 19.8 ± 1.6 |
| *B. multivorans* ATCC17616 | 2.9 ± 2.5 | 1.6 ± 1.4 | 0.84 ± 0.1 | 3.1 ± 1.7 |

The data presented in FIGS. 2A-C and Table 4 shows that compounds 2, 3 and 10 are effective against both *B. multivorans* and *P. aeruginosa*. The compounds of the invention were typically five-fold more potent against *B. multivorans* than against *P. aeruginosa*.

Unexpectedly, compound 10 is 4 to 5 times more potent than Argyrin A when tested against either *B. multivorans* or *P. aeruginosa*.

The activity ($IC_{50}$) of the dehydrophenylalanine containing compound 12, dehydrovaline containing compound 13 and dehydroleucine containing compound 14 against *B. multivorans* ATCC17616 are 1.1±0.2, 1.54±0.2 and 0.98±0.1 µM, respectively. In contrast to their substantial loss of activity against *P. aeruginosa* PAO1, replacement of the dehydroalanine residue in compound 3 with either dehydrophenylalanine (compound 12) or dehydroleucine (compound 14) unexpectedly resulted in marginal gain, 1.5-1.6-fold, in antimicrobial potency against *B. multivorans* ATCC17616, in comparison to the Dha containing compound 3. The corresponding dehydrovaline containing compound 13 showed similar potency to the Dha containing compound 3.

Compound 3 was tested to determine its antibacterial activity against *B. multivorans, B. cepasia* and *B. vietnamiensis.*

Figure 3:
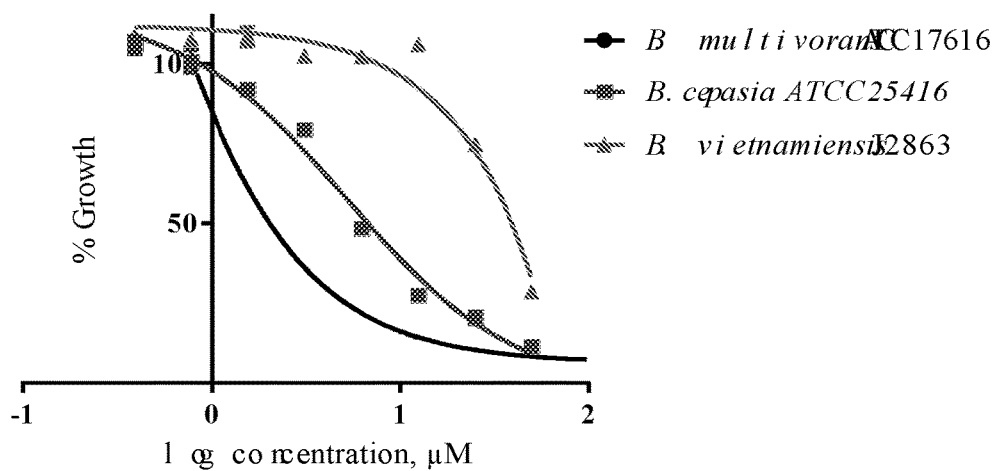
FIG. 3 is a graph showing the effect of varying concentrations of compound 3 according to the invention on the growth of *Burkholderia* in Lysogeny broth (LB broth) after 17 hours.

FIG. 3 shows the results for antibacterial activity of compound 3 against these three other Bcc organisms. It can be seen that compound 3 is highly active against each of these other Bcc organisms, with a significant decrease in growth in each case.

Activity of the Compounds Against *Clostridium difficile*

The compounds of the invention are also useful in the treatment of *C. difficile* infections. In particular, compounds 2, 3, 9 and 10 have been tested and shown to exhibit activity against *C. difficile*.

Figure 4A:
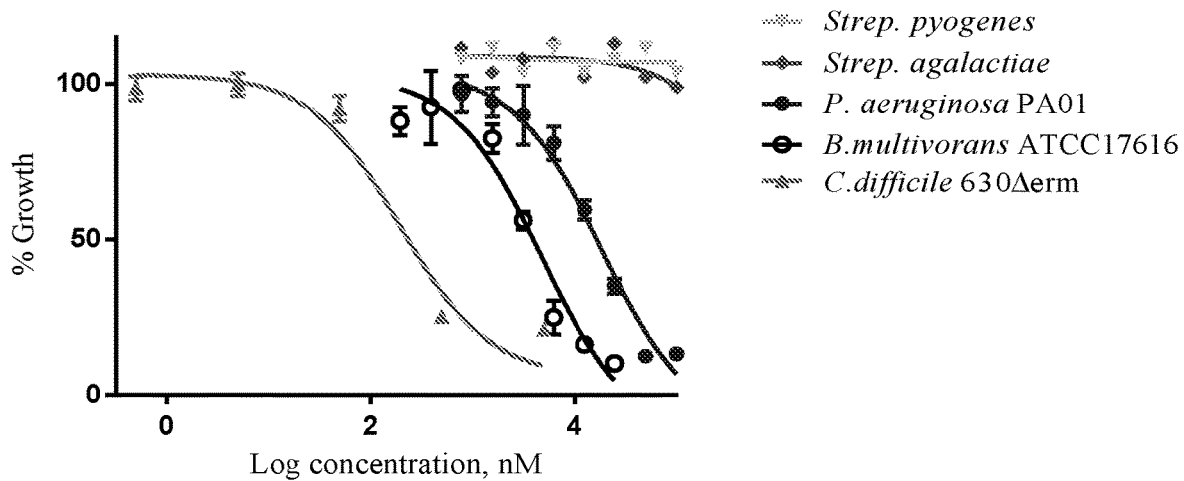
FIGS. 4a and 4b are graphs showing the effect of varying concentrations of compounds 2 and 3 according to the invention on the growth of four different organisms after 13 hours and on the growth of *B. multivorans* after 25 hours.
Figure 4B:
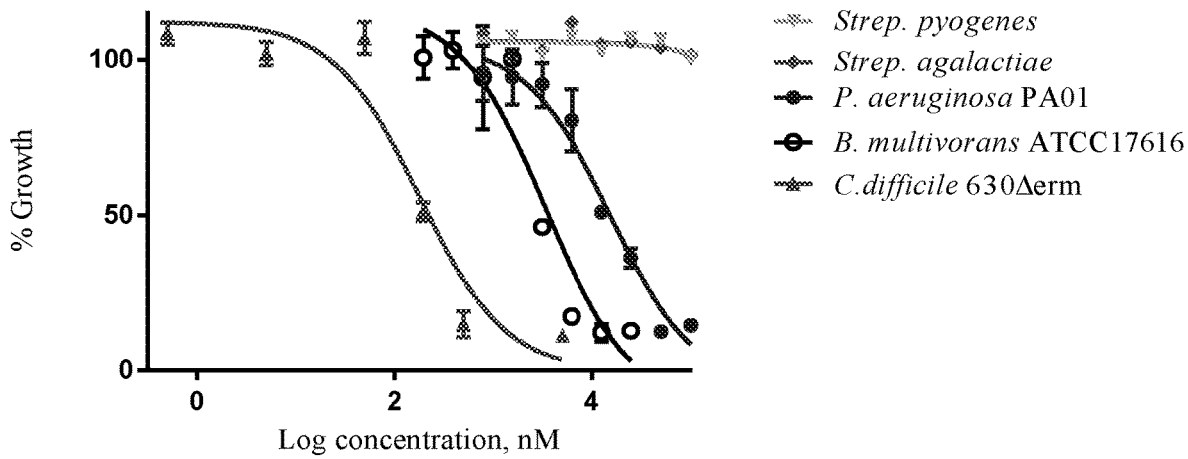

The activity profile of compounds 2 and 3 against *C. difficile* is presented in FIGS. 4A-B and Table 5. FIG. 4A shows the results for compound 2; FIG. 4B shows the results for compound 3.

The indicator strains, Strep. *pyogenes* and Strep. *agalactiae*, are representative of other Gram-positive bacteria, such as those associated with healthy gut flora.

It can be seen that compounds 2 and 3 are effective against *C. difficile* but do not adversely affect the growth of the indicator strains, Strep. *pyogenes* and Strep. *Agalactiae.*

Thus, the results show that the compounds of the invention are selective *C. difficile* agents.

It is further noteworthy that the preferred compounds are at least 100-fold more potent against *C. difficile* than *P. aeruginosa.*

Comparative in vitro bacterial susceptibility to compounds 3, 9 and 10, vancomycin and metronidazole was determined using methods according to the Clinical and Laboratory Standard Institute (CLSI) approved guidelines (M7-A10, M11-A7 or M45-A2) for anaerobic and aerobic organisms.

Tests were performed in triplicates and the MICs are summarized in Tables 6 and 7. In these results, minimum inhibitory concentration (MIC) is defined as the lowest concentration of test compound that resulted in complete inhibition of visible bacterial growth following incubation at 37° C. for 24-48 h.

Compound 10 shows both excellent potency and unprecedented selectivity for *C. difficile*. Approximately 90% of the 23 representatives of normal gut flora and therefore are surrogates of intestinal microbiota are insensitive to compound 10 at 64 µg/mL, whilst both *Clostridium difficile* and *Clostridium sordellii* are highly susceptible to the antimicrobial activity of compound 10 (Table 6).

For example, compound 10 is at least 256-fold more potent against *C. difficile* ATCC 43255 (MIC 0.25 µg/mL) compared to *Bacteroides fragilis* (MIC>64 µg/mL). In contrast, metronidazole is equally effective against *C. difficile* and *B. fragilis* (MIC 0.5 µg/mL).

Compound 3 also shows a similar spectrum of selectivity for *C. difficile* ATCC 43255 (MIC 1.0 µg/mL).

There is strong evidence that retention of the normal microflora, especially species of the *B. fragilis* group, would lower the risk of recurrent CDAD.

It is known that the presence of *Clostridium scindens* in the gut can help to keep *Clostridium difficile* at bay. In a separate study it was found that the growth of *Clostridium scindens* is unaffected by compound 10 at 80.0 µg/mL. This would not be the case if a broad-spectrum antibiotic, such as vancomycin or metronidazole, was to be used. The lack of activity against *Clostridium scindens* would, therefore, further help the gut to recover from *Clostridium difficile* infection.

The comparative in vitro antimicrobial results provide evidence that the compounds of the invention are narrow spectrum antimicrobials and can selectively inhibit *C. difficile* organisms in vivo. Therefore, the compounds of the invention can be used to treat CDAD in a patient without causing disturbances of the normal dynamics or integrity of gut microbiota by administering an effective amount of a compound of the invention.

TABLE 5

$IC_{50}$ values for compounds 2 and 3 measured at 13 h (*B. multivorans* at 25 h)

| Organisms | $IC_{50}$ (µM) | |
| --- | --- | --- |
| | Compound 2 | Compound 3 |
| *C. difficile* 630Δerm | 0.18 ± 0.03 | 0.13 ± 0.02 |
| *P. aeruginosa* PAO1 | 16.8 ± 2.9 | 13.2 ± 3.2 |
| *B. multivorans* ATCC17616 | 2.9 ± 2.5 | 1.6 ± 1.4 |
| Strep. pyogenes | >100 | >100 |
| Strep. agalactiae | >100 | >100 |

TABLE 6

Comparative in vitro activity of compounds 10 and 3, vancomycin and metronidazole against representative gut bacteria.

| | | MIC (µg/mL) | | | |
| --- | --- | --- | --- | --- | --- |
| Organism | Strain | Compound 10 | Compound 3 | Vancomycin | Metronidazole |
| *Clostridium perfringens* | NCTC 8237 | 64 | >64 | — | 1.0 |
| *Bacteroides fragilis* | ATCC 25285 | >64 | >64 | — | 0.5 |
| *Clostridium difficile* | ATCC 43255 | 0.25 | 1.0 | — | 0.5 |
| *Clostridium sordellii* | ATCC 9714 | 1.0 | 32 | — | 1.0 |
| *Clostridium ramosum* | DSM 1402 | >64 | >64 | — | 4.0 |
| *Clostridium innocuum* | DSM 1286 | >64 | >64 | — | 0.5 |
| *Propionibacterium acnes* | ATCC 6919 | >64 | >64 | — | >64 |
| *Bifidobacterium bifidum* | ATCC 11863 | >64 | >64 | — | 2.0 |
| *Bifidobacterium breve* | ATCC 15700 | >64 | >64 | — | 4.0 |

TABLE 6-continued

Comparative in vitro activity of compounds 10 and 3, vancomycin and metronidazole against representative gut bacteria.

| | | MIC (μg/mL) | | | |
|---|---|---|---|---|---|
| Organism | Strain | Compound 10 | Compound 3 | Vancomycin | Metronidazole |
| Actinomyces viscosus | DSM 43327 | 8 | 64 | — | 2.0 |
| Corynebacterium jeikeium | NCTC 11914 | >64 | >64 | 1.0 | — |
| Corynebacterium urealyticum | NCTC 12011 | >64 | >64 | 1.0 | — |
| Corynebacterium striatium | NCTC 764 | >64 | >64 | 0.5 | — |
| Lactobacillus rhamnosus | ATCC 53103 | >64 | >64 | >64 | — |
| Enterococcus faecalis | ATCC 29212 | >64 | >64 | 2.0 | — |
| Enterococcus faecium | NCTC 12204 | >64 | >64 | >64 | — |
| Staphylococcus aureus | ATCC 29213 | >64 | >64 | 1.0 | — |
| Pseudomonas aeruginosa | ATCC 27853 | >64 | >64 | — | — |
| Pseudomonas aeruginosa | NCTC 13437 | >64 | >64 | — | — |
| Escherichia coli | ATCC 25922 | >64 | >64 | — | — |
| Enterobacter cloacae | NCTC 13406 | >64 | >64 | — | — |
| Citrobacter koseri | Clinical | >64 | >64 | — | — |
| Proteus mirabilis | DSM 30116 | >64 | >64 | — | — |

Compound 10 shows unexpectedly high potency against *Clostridium sordellii* (MIC 1.0 μg/mL, Table 6). *Clostridium sordellii*, being part of the normal flora of the gut, as well as vagina, may gain entry to the uterus via the cervix during spontaneous or induced abortion and childbirth. Most significantly, faecal vaginal contamination during or after childbirth is the source of *C. sordellii* infection, which is the cause of systemic toxic shock syndrome and is often fatal.

Antimicrobial susceptibility to compounds 9 and 10 was determined against a selection of 21 uncharacterised clinical (isolates from North-West UK hospitals during 2010-2011) and 7 reference (clinically relevant and a CLSI reference) *C. difficile* strains, including hypervirulent and clinical samples from hospitalized patients. The method used was based on the broth micro-dilution method described in CLSI M11-A7. Specifically, compounds 9 and 10 were dissolved in sterile DMSO at 2.56 mg/mL. Stock solutions of these compounds were diluted 1:40 in supplemented *Brucella* broth to a concentration of 64 μg/mL. Serial 1:1 dilutions of test compounds in supplemented *Brucella* broth were then performed in round-bottom 96-well plates (Corning 3788). *C. difficile* strains were cultured from frozen bead stocks on pre-reduced Columbia blood agar plates, followed by 2 passages on *C. difficile* selective media. The inocula were prepared by suspending single colonies from a 24-48 h old F3 streak plate of the appropriate *C. difficile* strain in pre-reduced sterile phosphate-buffered saline (PBS) to a density equivalent to a 0.5 McFarland standard, which was then further diluted 1:15 in supplemented *Brucella* broth to yield a final inoculum of $2-8 \times 10^5$ CFU/mL in each well, following addition to the 96-well assay plates. The assay plates were then incubated anaerobically at 37° C. for 46-48 h and end-points were visually determined. In addition to MIC, the $MIC_{50}$ and $MIC_{90}$ are useful descriptors when multiple isolates of *C. difficile* are tested; $MIC_{90}$ is defined as the represents the MIC value at which >90% of the strains within a test population are inhibited, i.e. 90th percentile.

Compounds 9 and 10 are effective antimicrobial agents ($MIC_{90}$=0.50 μg/mL) against all 28 clinically relevant and reference *C. difficile* strains (Table 7). No resistant *C. difficile* strains are observed.

Although the $MIC_{50}$ and $MIC_{90}$ values of compound 10 (0.50 μg/mL) are identical to those of compound 9 and vancomycin, 43% of the *C. difficile* strains tested are susceptible to compound 10 at 0.25 μg/mL. In contrast, none of the *C. difficile* strains tested are susceptible to vancomycin at 0.25 μg/mL. Therefore, advantageously, the compounds of the present invention can be effective at lower dosages.

TABLE 7

Comparative in vitro activity of compound 10, compound 9 and vancomycin against 28 clinically relevant and reference *Clostridium difficile* strains.

| | | MIC (μg/mL) | | | | |
|---|---|---|---|---|---|---|
| | Strain | Compound 10 | Strain | Compound 9 | Strain | Vancomycin |
| 1 | Clin. 1 | 0.25 | Clin. 3 | 0.25 | Clin. 1 | 0.5 |
| 2 | Clin. 3 | 0.25 | Clin. 16 | 0.25 | Clin. 2 | 0.5 |
| 3 | Clin. 7 | 0.25 | 630 | 0.25 | Clin. 3 | 0.5 |
| 4 | Clin. 10 | 0.25 | BI1-FDX$^R$ | 0.25 | Clin. 5 | 0.5 |
| 5 | Clin. 12 | 0.25 | ATCC 43255 | 0.25 | Clin. 6 | 0.5 |
| 6 | Clin. 16 | 0.25 | ATCC 700057 | 0.25 | Clin. 7 | 0.5 |
| 7 | Clin. 20 | 0.25 | Clin. 1 | 0.5 | Clin. 8 | 0.5 |
| 8 | Clin. 24 | 0.25 | Clin. 2 | 0.5 | Clin. 9 | 0.5 |
| 9 | 630 | 0.25 | Clin. 5 | 0.5 | Clin. 10 | 0.5 |
| 10 | BI1-FDX$^R$ | 0.25 | Clin. 6 | 0.5 | Clin. 11 | 0.5 |
| 11 | ATCC 43255 | 0.25 | Clin. 7 | 0.5 | Clin. 12 | 0.5 |
| 12 | ATCC 700057 | 0.25 | Clin. 8 | 0.5 | Clin. 13 | 0.5 |
| 13 | Clin. 2 | 0.5 | Clin. 9 | 0.5 | Clin. 14 | 0.5 |
| 14 | Clin. 5 | 0.5 | Clin. 10 | 0.5 | Clin. 15 | 0.5 |
| 15 | Clin. 6 | 0.5 | Clin. 11 | 0.5 | Clin. 16 | 0.5 |

TABLE 7-continued

Comparative in vitro activity of compound 10, compound 9 and vancomycin against 28 clinically relevant and reference *Clostridium difficile* strains.

| | | | MIC (µg/mL) | | | |
|---|---|---|---|---|---|---|
| | Strain | Compound 10 | Strain | Compound 9 | Strain | Vancomycin |
| 16 | Clin. 8 | 0.5 | Clin. 12 | 0.5 | Clin. 18 | 0.5 |
| 17 | Clin. 9 | 0.5 | Clin. 13 | 0.5 | Clin. 20 | 0.5 |
| 18 | Clin. 11 | 0.5 | Clin. 14 | 0.5 | Clin. 21 | 0.5 |
| 19 | Clin. 13 | 0.5 | Clin. 15 | 0.5 | Clin. 22 | 0.5 |
| 20 | Clin. 14 | 0.5 | Clin. 18 | 0.5 | Clin. 23 | 0.5 |
| 21 | Clin. 15 | 0.5 | Clin. 20 | 0.5 | Clin. 24 | 0.5 |
| 22 | Clin. 18 | 0.5 | Clin. 21 | 0.5 | ATCC 9689 | 0.5 |
| 23 | Clin. 21 | 0.5 | Clin. 22 | 0.5 | 630 | 0.5 |
| 24 | Clin. 22 | 0.5 | Clin. 23 | 0.5 | ATCC 13366 | 0.5 |
| 25 | Clin. 23 | 0.5 | Clin. 24 | 0.5 | BI1-FDX$^R$ | 0.5 |
| 26 | ATCC 9689 | 0.5 | ATCC 9689 | 0.5 | ATCC BAA 1875 | 0.5 |
| 27 | ATCC BAA 1875 | 0.5 | ATCC BAA 1875 | 0.5 | ATCC 43255 | 0.5 |
| 28 | ATCC 13366 | 1 | ATCC 13366 | 1 | ATCC 700057 | 0.5 |
| MIC40 | | 0.25 | | 0.5 | | 0.5 |
| MIC50 | | 0.5 | | 0.5 | | 0.5 |
| MIC90 | | 0.5 | | 0.5 | | 0.5 |

*Clostridium difficile* ATCC 9689: Ribotype 001; Isolate used in Antimicrob. Agents Chemother., 2014, 58, 892. *C. difficile* 630 (ATCC BAA 1382): Ribotype 012; Genome-sequenced strain, multi-drug resistant, isolated from a patient in Zurich, Switzerland in 1982. In vivo hamster model available. *C. difficile* NCTC 13366 (aka R20291): Ribotype 027; Isolated from faeces of a symptomatic patient. Outbreak at Stoke Mandeville hospital, UK. In vivo hamster model available. *C. difficile* BI1-FDX$^R$: BI1 with elevated in vitro fidaxomicin MIC. *C. difficile* ATCC BAA1875: Ribotype 078; Isolated in Georgia, USA. In vivo hamster model available. *C. difficile* ATCC 43255: Ribotype 87; Isolated from an abdominal wound. In vivo mouse model available. *C. difficile* ATCC 700057: Ribotype 038; CLSI QC strain.

In Vivo Pharmacokinetics in Mice

Molecules that are poorly absorbed across the gut wall are preferred as they can attain high local concentrations within the intestine, permitting localized action against *C. difficile*. Compounds of the invention are poorly absorbed by the gut, resulting in high local concentrations in the lower intestine and making their antibacterial action against *C. difficile* very effective.

To demonstrate the poor gut absorption of the compounds of this invention, compound 3 was evaluated in oral dose pharmacokinetic study in mice (C57BL/6J, males, supplied by Charles River). In this study, a single oral dose of compound 3 in 0.5% w/v aqueous methylcellulose at 5 mg/kg was administered to nine mice in a 10 mL/kg dosing volume and housed in metabolism cages. Following administration of the compound, serial blood samples of 50 µL was taken from the lateral tail vein at each of 7 post-dosing time-points (0.25, 0.5, 1, 2, 4, 7 and 24 h). Whole blood samples were then diluted 1:1 with water and two 40 µL aliquots were pipetted into duplicate 96 well plate tubes. At the end of 24 h, all faecal samples were collected and pooled. A quantitative bioanalysis by LC-MS/MS of the blood and faecal levels of compound 3 was carried out to determine the oral absorbability and gastrointestinal metabolic stability of compound 3.

The results of this study show that systemic exposure is undetectable for compound 3 over 24 h. Therefore, orally administered compounds of the invention most likely reach high local concentration in the lower intestine, where its action against *C. difficile* can be most effective. At 24 h an average of 63% of compound 3 was recovered from the pooled mice faecal sample.

Using the above methods, following an oral administration of compound 10 at 5 mg/kg to C57BL/6J mice, up to 90% of compound 10 was recovered from 24-hour pooled faeces. A single 5 mg/kg oral dose of compound 10 in mice resulted in faecal concentrations of 92-125 µg/g (mean 112 µg/g), which is more than 200 times above the MIC (0.25-0.50 µg/mL) of compound 10 against *C. difficile*.

To evaluate the metabolic stability of orally administered compound 3, metabolite profiling of the faecal sample was performed. Quantification of LC-MS analysis of the pooled faecal sample shows that 85% of the mass of compounds detected, above those in the control sample, corresponds to compound 3.

In summary, the oral dose pharmacokinetics and metabolite profiling in mouse demonstrates that the compounds of present invention have no detectable systemic absorption. Since no major metabolites were detected, the compounds of the invention have good gastrointestinal metabolic stability.

Efficacy of the Compounds of the Invention against *C. difficile*-Associated Disease in a Hamster Model Comparative efficacy of orally administered compound 10 was determined using Golden Syrian hamsters following infection with the hypervirulent *C. difficile* BI1 (BI/NAP1, ribotype 027) (N. Razaq, S. Sambol, K. Nagaro, W. Zukowski, A. Cheknis, S. Johnson and D. N. Gerding, *J. infect. Dis.*, 2007, 196, 1813-181) The *C. difficile* BI1 is selected as the infective agent since it is the predominant strain in the USA, accounting for approximately one-third of clinical cases, and is the most commonly isolated ribotype in Europe. Disease progression in hamsters is more rapid and more lethal in this model than is typically observed in humans, making the hamster model of CDAD useful for evaluating the dose-response relationship of experimental therapies and used to support the progression of clinical drug candidates to human efficacy studies (N. Razaq, S. Sambol, K. Nagaro, W. Zukowski, A. Cheknis, S. Johnson and D. N. Gerding, *J. infect. Dis.*, 2007, 196, 1813-1819; E. L. Best, J. Freeman and M. H. Wilcox, *Gut Microbes*, 2012, 3, 145-167).

Three different doses, 0.2 mg/kg, 1.0 mg/kg and 2.5 mg/kg, of compound 10 were assessed, and compared against the vehicle (1% DMSO in 0.5% aqueous methylcellulose; the control group). The treatments were initiated 6 h after *C. difficile* infection and continued twice daily at 12 h intervals for 5 days post-infection. The study groups, 10 animals in each group, were followed for a total of 21 days after infection. Male Golden Syrian hamsters were supplied by Janvier and were specific pathogen free. Hamsters, pair housed in sterile individual ventilated cages, were allowed to acclimatise for at least 7 days prior to start of experiments (weight at the start of experiment 99-105 g).

*C. difficile* BI1 was cultured on to multiple brain heart infusion agar plates supplemented with 0.01% L-cysteine (BHIS) and cultured for 6 days under anaerobic conditions at 37° C. After 6 days, colonies were harvested into 70% ethanol to kill vegetative bacteria. The resultant spore suspensions were washed 3 times in PBS to remove toxin and were frozen in aliquots. The number of spores was determined to be approximately $8 \times 10^5$ spores/mL. Frozen stocks were diluted on the day of study. Hamsters were pre-conditioned with 30 mg/kg oral clindamycin 24 h before infection, and were infected with 1 mL of the inoculum by gastric administration. The inoculum contained approximately $6.5 \times 10^3$ spores/hamster.

Stock solutions of compound 10 at 2.0, 10.0 and 25.0 mg/mL were prepared in DMSO and then diluted 1:100 with 0.5% aqueous methylcellulose to produced dosing solutions of 0.02, 0.10 and 0.25 mg/mL. Fresh dosing solution was prepared each day and stored at 4° C. until required. Compound 10 was administered at 10 mL/kg to deliver doses of 0.2, 1.0 and 2.5 mg/kg respectively. Treatments were initiated 6 hours after infection and continued BD (bi-daily dosage) at 12 h intervals for 5 days post-infection. All study animals were observed for up to 21 days post-infection. The clinical condition of the animals was monitored and animals were euthanized by pentobarbitone overdose upon severe clinical deterioration (body temperature <32° C., and/or weight loss ≥20%, severe diarrhoea and/or prostrate and/or unable to reach food and water, and/or severely hunched with piloerection).

A robust hamster model of CDAD was established following infection with *C. difficile* BI1, and the survival data are shown in Table 8.

In the vehicle control group, 100% of hamsters succumbed to the disease by 32.5 h post-infection. Using non-optimised doses, treatment with compound 10 showed a significant dose dependent increase in survival time compared to the vehicle control.

TABLE 8

Kaplan-Meier mean survival times of hamsters (n = 10 in each group) following infection with *C. difficile* BI1.

| Treatment | Mean survival (h) |
|---|---|
| Vehicle | 32.50 |
| Compound 10, 0.2 mg/kg | 35.75 |
| Compound 10, 1.0 mg/kg | 154.63 |
| Compound 10, 2.5 mg/kg | 205.92 |

In the drug treatment groups, 100% of hamsters treated with compound 10 at 0.2 mg/kg succumbed to the disease within 36 hours post-infection. Hamsters treated with compound 10 at 1.0 mg/kg and 2.5 mg/kg twice daily survived an average of 155 h (6.5 days) and 206 h (8.5 days), respectively, with 10% of the animals reaching the end of the study at day-21 post-infection. This is a significant 4.7- and 6.3-fold increase, respectively, in survival time compared to vehicle control. At the dose of 2.5 mg/kg twice daily, compound 10 conferred significant protection with 100% survival at day 6 post-infection, followed by a gradual loss of animals between day 7 and 9 post-infection.

Efficacy of Compound 10 of the Invention Against *C. difficile*-Associated Disease in a Mouse Model Although the hamster model of CDAD is a highly durable and efficient model, it represents a fulminant and lethal course of disease, with death occurring within 1-2 days post-infection, and as such does not represent the usual progression and spectrum of CDAD in humans. The mouse model of CDAD is increasingly used to study the effectiveness of experimental antimicrobials and treatment modalities on the disease progression (for example, L. T. Erikstrup, M. Aarup, R. Hagemann-Madsen, F. Dagnaes-Hansen, B. Kristensen, K. E. P. Olsen and K. Fuursted, *BMJ Open Gastro*, 2015, 2, e000038), including the relapse/recurrence of infection, since the disease development and severity can be varied by the *C. difficile* strain used for the infection and by the size and nature (spores or vegetative cells) of the bacterial inoculum (X. Chen, K. Katchar, J. D. Goldsmith, N. Nanthakumar, A. Cheknis, D. N. Gerding and C. P. Kelly, *Gastroenterol.*, 2008, 135, 1984-1992; C. M. Theriot, C. C. Koumpouras, P. E. Carlson Jr., I. L. Bergin, D. M. Aronoff and V. B. Young, *Gut Microbes*, 2011, 2, 326-334; A. E. Reeves, C. M. Theriot, I. L. Bergin, G. B. Huffnagle, P. D. Schloss and V. B. Young, *Gut Microbes*, 2011, 2, 145-158).

The efficacy of orally administered compound 10, in comparison to vancomycin, fidaxomicin and SMT19969 (aka ridinilazole) was determined using C57BL/6 mice, pre-conditioned with cefoperazone followed by clindamycin, and following by infection with virulent *C. difficile* ATCC 43255 (aka VPI 10463; ribotype 087) (A. E. Reeves, C. M. Theriot, I. L. Bergin, G. B. Huffnagle, P. D. Schloss and V. B. Young, *Gut Microbes*, 2011, 2, 145-158).

Three different doses, 1.0 mg/kg, 2.5 mg/kg and 5.0 mg/kg, of compound 10 were assessed, and compared against the vehicle (1% DMSO in 0.5% aqueous methylcellulose; the control group), vancomycin (10 mg/kg), fidaxomicin (2.5 mg/kg) and SMT19969 (20 mg/kg). The treatments were initiated 5 h after *C. difficile* infection and continued twice daily at 12 h intervals for 5 days post-infection. The study groups, 10 animals in each group, were followed for a total of 21 days after infection. The C57BL/6 mice (6-week old males) were supplied by Envigo, specific pathogen free, typically housed in groups of 5 in sterile individual ventilated cages and allowed to acclimatise for at least 7 days prior to start of experiments (weight at the start of experiment was on average 25 g).

In the pre-conditioning phase, mice were pre-treated for 10 days with 0.05 mg/mL cefoperazone in sterile drinking water from days minus-12 to minus-2 relative to infection. The antibiotic water was changed every other day in order to minimise antibiotic deterioration. Forty-eight hours pre-infection, the antibiotic water was substituted by antibiotic-free water. Additionally, mice were pre-conditioned with 10 mg/kg clindamycin administered intraperitoneally 24 hours before infection.

*C. difficile* ATCC 43255 was inoculated onto brain heart infusion agar supplemented with 0.01% L-cysteine (BHIS) and cultured overnight under anaerobic conditions at 37° C. to afford single colonies. A single colony was then used to inoculate 20 mL of pre-reduced BHIS broth, which was cultured overnight under anaerobic conditions and without shaking. A 1:5 dilution of this was cultured in fresh pre-reduced media for 4 h under anaerobic conditions at 37° C. to ensure the growth was in the mid-phase logarithmic growth before use. The bacteria were washed three times in pre-reduced PBS to remove toxin and was finally re-suspended in 50 mL pre-reduced PBS to give approximately $4\times10^8$ CFU/mL. For infection, each mouse was given 0.1 mL of the above inoculum by gastric administration, i.e. approximately $4\times10^7$ CFU/mouse.

Stock solutions of compound 10 at 10, 25 and 50 mg/mL were prepared in DMSO and then diluted 1:100 with 0.5% aqueous methylcellulose to produced dosing solutions of 0.1, 0.25 and 0.5 mg/mL. Vancomycin (Vancocin 500 mg, Wockhardt UK Ltd., Batch number L630, Expiry August 2019) was prepared as per manufacturer instruction to give 50 mg/mL stock solution. This was further diluted 1:50 in water for injection to obtain 1 mg/mL dosing solution. Fidaxomicin (Dificlir 200 mg, Astellas, Lot 15K23/85, Expiry October 2018) stock solution of 10 mg/mL was prepared in DMSO and then diluted 1:40 with water for injection to produce dosing solution of 0.25 mg/mL. SMT19969 stock solution of 20 mg/mL was prepared in DMSO and then diluted 1:10 with 0.5% methylcellulose to produce dosing solution of 2 mg/mL. Fresh dosing solution was prepared each day and stored at 4° C. until required. Test articles were administered at 10 mL/kg, and treatments were initiated 5 hours after infection and continued BD at 12 h intervals for 5 days post-infection. All study animals were observed for up to 21 days post-infection. The clinical condition of the animals was monitored, and animals were euthanized by pentobarbitone overdose upon severe clinical deterioration or at the end of study. Following confirmation of death, the content from approximately 2 cm length of colon, caecum and small intestine was cultured for the presence of *C. difficile* spores.

Figure 5:
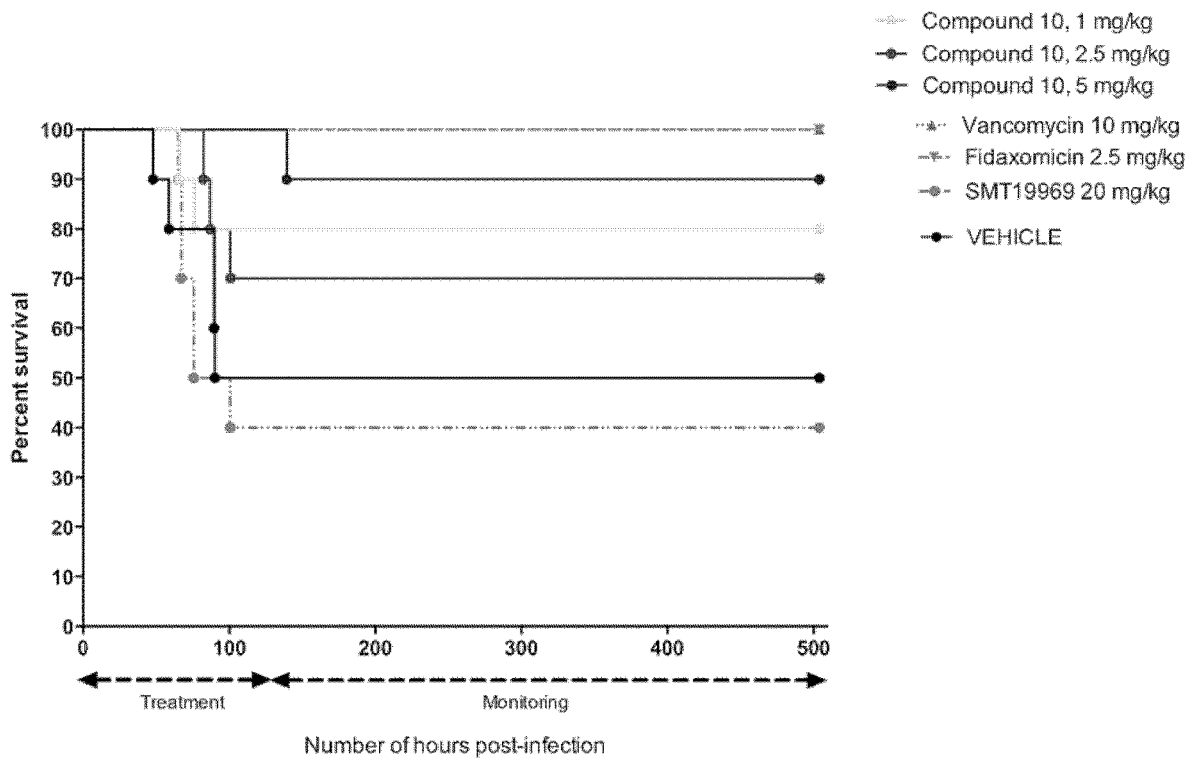
FIG. 5 is a graph showing the survival in hours following infection of mice with *C. difficile* ATCC 43255.

A robust mouse model of CDAD was established with 50% of mice in the vehicle control group succumbing to the disease by 90 hours post-infection (FIG. 5, Tables 9 and 10).

Figure 6:
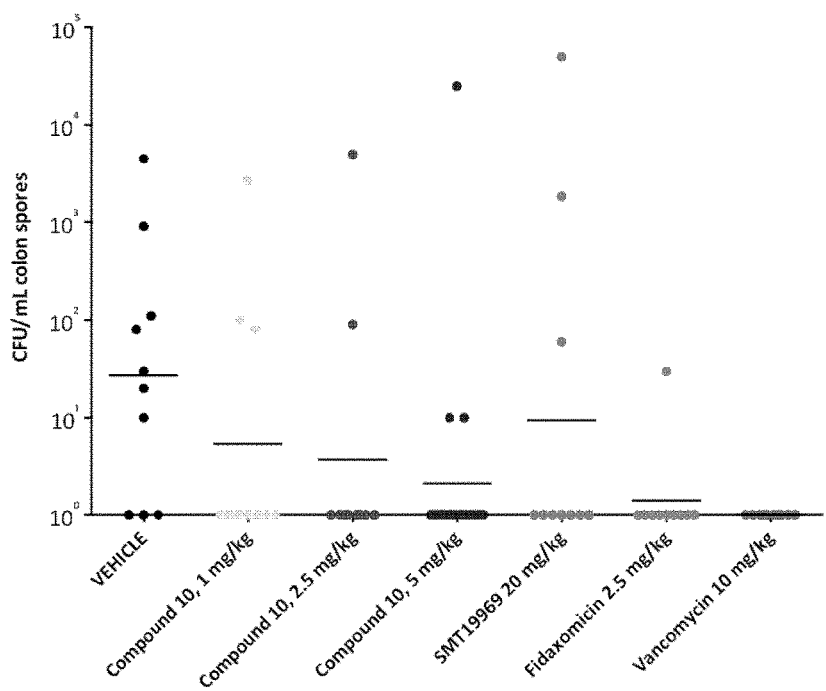
FIG. 6 is a scattergram of colon spore burden following infection with *C. difficile* ATCC 43255. The geometric mean burden of each treatment is indicated by the horizontal bar. NS=not significant.

The majority of mice treated with compound 10 at 1 mg/kg (80% survival), 2.5 mg/kg (70% survival) and 5 mg/kg (90% survival) reached the end of the study at day-21 post-infection. Survival of animals treated with compound 10 at 5 mg/kg BD for 5 days was significantly increased and statistically different to that of vehicle controls (Log-rank: P=0.0416, Generalised Wilcoxon (Peto-Prentice): P=0.034) (FIG. 5, Tables 9 and 10). Treatment with the compound 10 at 5 mg/kg also caused a significant reduction in *C. difficile* spore burden in the colon (FIG. 6) and caecum, in comparison to vehicle controls (colon: 1.11 $Log_{10}$ spore/mL reduction, p=0.0171; caecum: 1.73 $Log_{10}$ spore/mL reduction, p=0.026). All mice treated with the comparators, vancomycin and fidaxomicin survived to the end of the study at day-21 post-infection, both of which were statistically different to vehicle controls.

TABLE 9

Kaplan-Meier mean survival times of mice (n = 10 in each group) following infection with *C. difficile* ATCC 43255.

| Treatment | Mean survival (h) |
|---|---|
| Vehicle | 297.00 |
| Compound 10, 1 mg/kg | 504.00 |
| Compound 10, 2.5 mg/kg | 504.00 |
| Compound 10, 5 mg/kg | 504.00 |
| Vancomycin, 10 mg/kg | 504.00 |
| Fidaxomicin, 2.5 mg/kg | 504.00 |
| SMT19969, 20 mg/kg | 88.00 |

TABLE 10

Statistical analysis (Log Rank and Wilcoxon test) of survival times of animals treated with test articles compared to Vehicle controls following infection with *C. difficile* ATCC 43255.

| Comparison | Log Rank | Peto-Prentice |
|---|---|---|
| Compound 10, 1 mg/kg vs Vehicle | NS | NS |
| Compound 10, 2.5 mg/kg vs Vehicle | NS | NS |
| Compound 10, 5 mg/kg vs Vehicle | P = 0.0416 | P = 0.034 |
| Vancomycin, 10 mg/kg vs Vehicle | P = 0.0116 | P = 0.0125 |
| Fidaxomicin, 2.5 mg/kg vs Vehicle | P = 0.0116 | P = 0.0125 |
| SMT19969, 20 mg/kg vs Vehicle | NS | NS |

NS = not significant.

The invention claimed is:
1. A compound of formula (I):

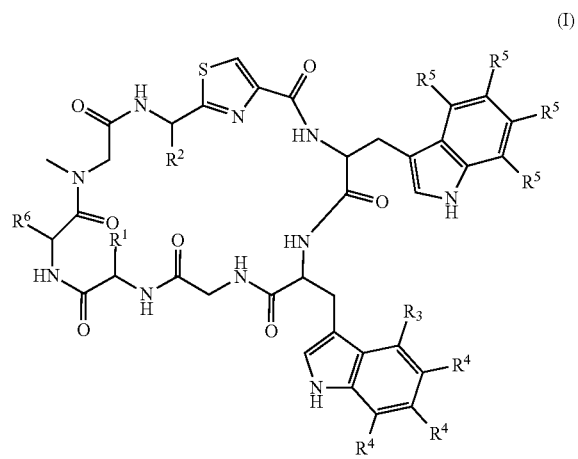

including tautomeric or stereochemically isomeric forms thereof, wherein:
$R^1$ and $R^2$ each independently represent hydrogen, $C_1$-$C_8$ alkyl optionally substituted by one or more $R^x$ groups, $C_3$-$C_8$ cycloalkyl optionally substituted by one or more $R^x$ groups, $C_2$-$C_8$ alkenyl optionally substituted by one or more $R^x$ groups, $C_6$-$C_{10}$ aryl optionally substituted by one or more $R^x$ groups, $C_4$-$C_{10}$ heterocyclyl optionally substituted by one or more $R^x$ groups, or $R^x$;
$R^3$ represents halogen;
each $R^4$ and each $R^5$ independently represent hydrogen, $C_1$-$C_8$ alkyl optionally substituted by one or more $R^x$ groups, $C_3$-$C_8$ cycloalkyl optionally substituted by one or more $R^x$ groups, $C_2$-$C_8$ alkenyl optionally substituted by one or more $R^x$ groups, $C_6$-$C_{10}$ aryl optionally substituted by one or more $R^x$ groups, $C_4$-$C_{10}$ heterocyclyl optionally substituted by one or more $R^x$ groups, or $R^x$;
$R^6$ represents =$CR^7R^8$, $C_2$-$C_8$ alkenyl optionally substituted by one or more $R^x$ groups, $C_6$-$C_{10}$ aryl optionally substituted by one or more $R^x$ groups, $C_4$-$C_{10}$ heterocyclyl optionally substituted by one or more $R^x$ groups, or $R^x$;
$R^7$ and $R^8$ independently represent hydrogen, $C_1$-$C_8$ alkyl optionally substituted by one or more $R^x$ groups, $C_3$-$C_8$ cycloalkyl optionally substituted by one or more $R^x$ groups, $C_2$-$C_8$ alkenyl optionally substituted by one or more $R^x$ groups, $C_6$-$C_{10}$ aryl optionally substituted by one or more $R^x$ groups, $C_4$-$C_{10}$ heterocyclyl optionally substituted by one or more $R^x$ groups, or $R^x$; each $R^x$ independently represents cyano, halogen, —B(OR$^Y$)$_2$, —C(O)R$^Y$, —C(O)OR$^Y$, —OC(O)R$^Y$, —C(O)NHR$^Y$, —NHC(O)R$^Y$, —NHC(O)NHR$^Y$, —NHC(O)OR$^Y$, —OC(O)NHR$^Y$, —OS(O)$_2$R$^Y$, —S(O)$_2$NHR$^Y$, —NHS(O)$_2$R$^Y$, —NR$^Y_2$ or —OR$^Y$; and each R$^Y$ independently represents hydrogen, C$_1$-C$_8$ alkyl, C$_6$-C$_{10}$ aryl, C$_4$-C$_{10}$ heterocyclyl or C$_2$-C$_8$ alkenyl;

or a N-oxide thereof or a pharmaceutically acceptable salt thereof or a pharmaceutically acceptable solvate thereof.

2. The compound according to claim 1, wherein R$^3$ represents bromo or chloro.

3. The compound according to claim 1, wherein R$^6$ represents =CR$^7$R$^8$.

4. The compound according to claim 1, wherein R$^7$ and R$^8$ independently represent hydrogen, C$_1$-C$_4$ alkyl or C$_2$-C$_4$ alkenyl.

5. The compound according to claim 4, wherein R$^7$ represents hydrogen and R$^8$ represents hydrogen, C$_1$-C$_4$ alkyl or C$_2$-C$_4$ alkenyl.

6. The compound according to claim 1, wherein R$^1$ and R$^2$ each independently represent hydrogen, C$_1$-C$_4$ alkyl optionally substituted by one or more R$^x$ groups, C$_2$-C$_4$ alkenyl optionally substituted by one or more R$^x$ groups, or R$^x$.

7. The compound according to claim 6, wherein R$^1$ and R$^2$ each independently represent hydrogen, C$_1$-C$_4$ alkyl optionally substituted by one or more R$^x$ groups or C$_2$-C$_4$ alkenyl optionally substituted by one or more R$^x$ groups.

8. The compound according to claim 7, wherein R$^1$ represents hydrogen, methyl or ethyl.

9. The compound according to claim 7, wherein R$^2$ represents C$_1$-C$_4$ alkyl optionally substituted by one or more R$^x$ groups, or C$_2$-C$_4$ alkenyl optionally substituted by one or more R$^x$ groups, wherein the R$^x$ group or groups are —OR$^Y$.

10. The compound according to claim 9, wherein R$^2$ represents methyl or hydroxymethyl or methoxymethyl.

11. The compound according to claim 1, wherein at least three R$^5$ groups are hydrogen and at least two R$^4$ groups are hydrogen.

12. The compound according to claim 11, wherein the compound is of formula (IA):

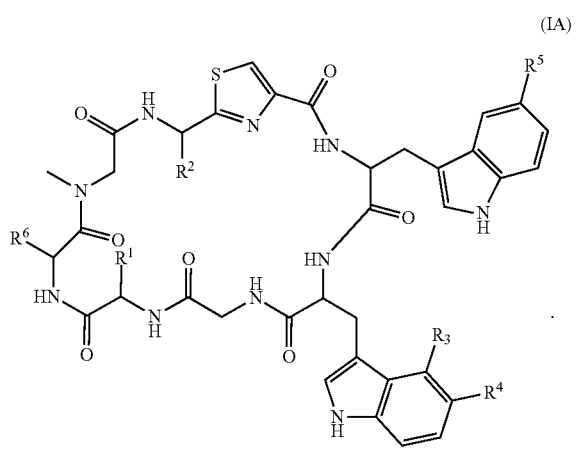

(IA)

13. The compound according to claim 12, wherein R$^4$ and R$^5$ each independently represent hydrogen, C$_1$-C$_4$ alkyl optionally substituted by one or more R$^x$ groups, C$_2$-C$_4$ alkenyl optionally substituted by one or more R$^x$ groups, or R$^x$.

14. The compound according to claim 13, wherein R$^4$ and R$^5$ each independently represent hydrogen or R$^x$.

15. The compound according to claim 1, wherein:

R$^1$ represents hydrogen or C$_1$-C$_4$ alkyl;

R$^2$ represents C$_1$-C$_4$ alkyl optionally substituted by one or more R$^x$ groups or C$_2$-C$_4$ alkenyl optionally substituted by one or more R$^x$ groups, wherein the R$^x$ group or groups are —OR$^Y$;

R$^3$ represents bromo or chloro or fluoro;

each R$^4$ independently represents hydrogen or methyl or —OMe or halogen;

each R$^5$ independently represents hydrogen or methyl or —OMe or halogen;

R$^6$ represents =CR$^7$R$^8$, where R$^7$ and R$^8$ independently represent hydrogen, C$_1$-C$_8$ alkyl optionally substituted by one or more R$^x$ groups, or C$_2$-C$_6$ alkenyl optionally substituted by one or more R$^x$ groups.

16. The compound according to claim 15, wherein:

R$^1$ represents hydrogen or C$_1$-C$_4$ alkyl;

R$^2$ represents C$_1$-C$_3$ alkyl optionally substituted by one R$^x$ group or C$_2$-C$_4$ alkenyl optionally substituted by one R$^x$ group, wherein the R$^x$ group is —OH or —OMe or —OEt;

R$^3$ represents bromo or chloro;

each R$^4$ independently represents hydrogen or methyl or —OMe or bromo or chloro;

each R$^5$ independently represents hydrogen or methyl or —OMe or halogen;

R$^6$ represents =CR$^7$R$^8$, where R$^7$ and R$^8$ independently represent hydrogen, or C$_1$-C$_4$ alkyl or C$_2$-C$_4$ alkenyl.

17. A pharmaceutical composition comprising the compound as defined in claim 1 and a pharmaceutically acceptable carrier or diluent.

18. The pharmaceutical composition according to claim 17, wherein the pharmaceutical composition is in the form of tablets, capsules, pills, powder packets, wafers, injectable solutions or suspensions.

19. A method for treating a subject having a bacterial infection, the method comprising: administering the compound of claim 1 to a subject in need thereof, thereby treating the bacterial infection in the subject, wherein the bacterial infection comprises infection by *Pseudomonas aeruginosa*, *Burkhoideria cepacia* and/or *Clostridium difficile*.

* * * * *